US006531494B1

(12) United States Patent
Khanna et al.

(10) Patent No.: US 6,531,494 B1
(45) Date of Patent: Mar. 11, 2003

(54) GEM-SUBSTITUTED $\alpha_v\beta_3$ ANTAGONISTS

(75) Inventors: Ish Kumar Khanna, Libertyville, IL (US); Yi Yu, Glenview, IL (US); Balekudru Devadas, Chesterfield, MO (US); Hwang-Fun Lu, Ballwin, MO (US); Nizal S Chandrakumar, Vernon Hills, IL (US); Renee M. Huff, Park Ridge, IL (US); Bipinchandra N. Desai, Vernon Hills, IL (US); Srinivasan Raj Nagarajan, Chesterfield, MO (US); Alan F. Gasiecki, Vernon Hills, IL (US); Thomas D. Penning, Elmhurst, IL (US); Mark A. Russell, Gurnee, IL (US); Mark L. Boys, Mt. Prospect, IL (US); Lori A. Schretzman, Gurnee, IL (US); Barbara B. Chen, Glenview, IL (US); Thomas Rogers, Ballwin, MO (US); John Adam Wendt, Libertyville, IL (US); Albert Khilevich, Buffalo Grove, IL (US); Yaping Wang, Naperville, IL (US)

(73) Assignee: Pharmacia Corporation, Peapack, NJ (US)

( * ) Notice: Subject to any disclaimer, the term of this patent is extended or adjusted under 35 U.S.C. 154(b) by 0 days.

(21) Appl. No.: 09/942,214

(22) Filed: Aug. 29, 2001

(51) Int. Cl.[7] .................... A61K 31/44; C07D 213/72
(52) U.S. Cl. .................... 514/352; 546/312; 546/194; 514/318
(58) Field of Search ................... 514/352, 318; 546/312, 194

(56) References Cited

U.S. PATENT DOCUMENTS

| 5,741,796 A | 4/1998 | Hartman et al. |
| 5,919,792 A | 7/1999 | Duggan et al. ............. 514/300 |
| 6,159,964 A | * 12/2000 | Ali et al. .................... 514/221 |

FOREIGN PATENT DOCUMENTS

| EP | 0478363 | 9/1991 | ......... C07D/211/22 |
| EP | 0 478 328 B1 | 1/1996 | |
| EP | 0 671 392 B1 | 2/2001 | |
| GB | 2 264 115 A | 8/1993 | |
| JP | 10287634 | 10/1998 | |
| WO | WO 93/21166 | 10/1993 | |
| WO | WO 95/32710 | 12/1995 | |
| WO | WO 96/41795 | 12/1996 | |
| WO | WO 97/12878 | 4/1997 | |
| WO | WO 97/24124 | 7/1997 | .......... A61K/31/55 |
| WO | WO 98/20871 | 5/1998 | |
| WO | WO 98/31359 | 7/1998 | |
| WO | WO 99/05107 | 2/1999 | ......... C07D/211/72 |
| WO | WO 99/15170 | 4/1999 | .......... A61K/31/44 |
| WO | WO 99/45927 | 9/1999 | |
| WO | WO 00/38665 | 7/2000 | |
| WO | WO 00/38715 | 7/2000 | |
| WO | WO 00/38719 | 7/2000 | |
| WO | WO 00/38786 | 7/2000 | |
| WO | WO 00/64888 | 11/2000 | |
| WO | WO 01/14337 A1 | 3/2001 | |
| WO | WO 01/14338 A1 | 3/2001 | |
| WO | WO 01/17959 | 3/2001 | |

* cited by examiner

*Primary Examiner*—Charanjit S. Aulakh
(74) *Attorney, Agent, or Firm*—Cynthia Kovacevic; Rachel Polster

(57) ABSTRACT

The present invention relates to a class of compounds represented by the Formula I.

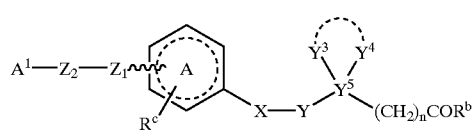

or a pharmaceutically acceptable salt thereof, pharmaceutical compositions comprising compounds of the Formula I, and methods of selectively inhibiting or antagonizing the $\alpha_v\beta_3$ and/or the $\alpha_v\beta_5$ integrin.

15 Claims, No Drawings

GEM-SUBSTITUTED $\alpha_v\beta_3$ ANTAGONISTS

The present application claims priority under Title 35, United States Code, §119 of United States Provisional application Serial No. 60/229,186 filed Aug. 30, 2000.

FIELD OF THE INVENTION

The present invention relates to pharmaceutical agents which are $\alpha_v\beta_3$ and/or $\alpha_v\beta_5$ integrin antagonists and as such are useful in pharmaceutical compositions and in methods for treating conditions mediated by $\alpha_v\beta_3$ and/or $\alpha_v\beta_5$ integrins.

BACKGROUND OF THE INVENTION

Integrins are a group of cell surface glycoproteins which mediate cell adhesion and therefore are useful mediators of cell adhesion interactions which occur during various biological processes. Integrins are heterodimers composed of noncovalently linked $\alpha$ and $\beta$ polypeptide subunits. Currently eleven different $\alpha$ subunits have been identified and six different $\beta$ subunits have been identified. The various $\alpha$ subunits can combine with various $\beta$ subunits to form distinct integrins.

The integrin identified as $\alpha_v\beta_3$ (also known as the vitronectin receptor) has been identified as an integrin which plays a role in various conditions or disease states including tumor metastasis, solid tumor growth (neoplasia), osteoporosis (Ross, et al., *J. Biol, Chem.*, 1987, 262, 7703), Paget's disease, humoral hypercalcemia of malignancy (Carron et al., *Cancer Res.* 1998, 58, 1930), osteopenia (Lark et al.,*J Bone Miner Res.* 2001, 16, 319), endometriosis (Healy et al., *Hum. Reproductive Update,* 1998, 4, 736), angiogenesis, including tumor angiogenesis (Cheresh, *Cancer Metastasis Rev.,* 1991, 10, 3–10 and Brooks, et al., *Cell,* 1994, 79, 1157), retinopathy including macular degeneration (Friedlander et al., *Proc. Natl. Acad. Sci USA* 1996, 93, 9764), arthritis, including rheumatoid arthritis (Badger et al., *Arthritis Rheum,* 2001, 44, 128), periodontal disease, psoriasis and smooth muscle cell migration (e.g. restenosis and artherosclerosis, (Brown et al., *Cardiovascular Res.,* 1994, 28, 1815). The compounds of the present invention are $\alpha_v\beta_3$ antagonists and can be used, alone or in combination with other therapeutic agents, in the treatment or modulation of various conditions or disease states described above. Additionally, it has been found that such agents would be useful as antivirals, antifungals and antimicrobials. Thus, compounds which selectively antagonize $\alpha_v\beta_3$ would be beneficial for treating such conditions.

The integrin $\alpha_v\beta_5$ plays a role in neovascularization. Antagonists of the $\alpha_v\beta_5$ integrin will inhibit neovascularization and will be useful for treating and preventing angiogenesis metastasis, tumor growth, macular degeneration and diabetic retionopathy. M. C. Friedlander, et al.,*Science,* 270, 1500–1502 (1995) disclose that a monoclonal antibody for $\alpha_v\beta_5$ inhibits VEFG-induced angogenesis in the rabbit cornea and the chick chorioallantoic membrane model. Therefore, it would be useful to antagonize both the $\alpha_v\beta_5$ and the $\alpha_v\beta_3$ receptor. Such "mixed $\alpha_v\beta_5/\alpha_v\beta_3$ antagonists" or "dual $\alpha_v\beta_3/\alpha_v\beta_5$ antagonists" would be useful for treating or preventing angiogenesis, tumor metastasis, tumor growth, diabetic retinopathy, macular degeneration, atherosclerosis and osteoporosis.

It has been shown that the $\alpha_v\beta_3$ integrin and other $\alpha_V$ containing integrins bind to a number of Arg-Gly-Asp (RGD) containing matrix macromolecules. Compounds containing the RGD sequence mimic extracellular matrix ligands so as to bind to cell surface receptors. However, it is also known that RGD peptides in general are non-selective for RGD dependent integrins. For example, most RGD peptides which bind to $\alpha_v\beta_3$ also bind to $\alpha_v\beta_5$, $\alpha_v\beta_1$ and $\alpha_{IIb}\beta_3$. Antagonism of platelet $\alpha_{IIb}\beta_3$ (also known as the fibrinogen receptor) is known to block platelet aggregation in humans. In order to avoid bleeding side-effects when treating the conditions or disease states associated with the integrin $\alpha_v\beta_3$, it would be beneficial to develop compounds which are selective antagonists of $\alpha_v\beta_3$ as opposed to $\alpha_{IIb}\beta_3$.

Further, it has not been established in the art that sparing $\alpha_v\beta_6$ integrin would be a beneficial property to be incorporated in the design of antagonists of $\alpha_v\beta_3$. Rather, $\alpha_v\beta_6$ has been identified as a target for antagonists because it is higly expressed in many carcinoma cell lines, and has been shown to enchance the proliferative capacity of a colon carcinoma cell line both in vivo and in vitro (Agrez et al., 1994,*J. Cell Biol.* 127, 547). Additionally, $\alpha_v\beta_6$ is expressed during the later stages of wound healing and remains expressed until the wound is closed (See Christofidou-Solomidou, et al., 1997 *American J. of Pathol.,* 151, 975), and therefore it is believed that $\alpha_v\beta_6$ plays a role in the remodeling of the vasculature during the later stages of angiogenesis. Accordingly, antagonists of $\alpha_v\beta_6$ are seen as useful in treating or preventing cancer by inhibiting tumor growth and metastasis (see, for example, U.S. Pat. No. 6,211,191).

Tumor cell invasion occurs by a three step process: 1) tumor cell attachment to extracellular matrix; 2) proteolytic dissolution of the matrix; and 3) movement of the cells through the dissolved barrier. This process can occur repeatedly and can result in metastases at sites distant from the original tumor.

Seftor et al. (*Proc. Natl. Acad. Sci. USA,* Vol. 89 (1992) 1557–1561) have shown that the $\alpha_v\beta_3$ integrin has a biological function in melanoma cell invasion. Montgomery et al., (*Proc. Natl. Acad. Sci. USA,* Vol. 91 (1994) 8856–60) have demonstrated that the integrin $\alpha_v\beta_3$ expressed on human melanoma cells promotes a survival signal, protecting the cells from apoptosis. Mediation of the tumor cell metastatic pathway by interference with the $\alpha_v\beta_3$ integrin cell adhesion receptor to impede tumor metastasis would be beneficial.

Brooks et al. (*Cell,* Vol. 79 (1994) 1157–1164) have demonstrated that antagonists of $\alpha_v\beta_3$ provide a therapeutic approach for the treatment of neoplasia (inhibition of solid tumor growth) since systemic administration of $\alpha_v\beta_3$ antagonists causes dramatic regression of various histologically distinct human tumors.

The adhesion receptor integrin $\alpha_v\beta_3$ was identified as a marker of angiogenic blood vessels in chick and man and therefore such receptor plays a critical role in angiogenesis or neovascularization. Angiogenesis is characterized by the invasion, migration and proliferation of smooth muscle and endothelial cells. Antagonists of $\alpha_v\beta_3$ inhibit this process by selectively promoting apoptosis of cells in neovasculature. The growth of new blood vessels, or angiogenesis, also contributes to pathological conditions such as diabetic retinopathy including macular degeneration (Adamis et al., *Amer. J. Ophthal.,* Vol. 118, (1994) 445–450) and rheumatoid arthritis (Peacock et al.,*J. Exp. Med.,* Vol. 175, (1992), 1135–1138). Therefore, $\alpha_v\beta_3$ antagonists would be useful therapeutic agents for treating such conditions associated with neovascularization (Brooks et al., *Science,* Vol. 264, (1994), 569–571).

It has been reported that the cell surface receptor $\alpha_v\beta_3$ is the major integrin on osteoclasts responsible for attachment to bone. Osteoclasts cause bone resorption and when such bone resorbing activity exceeds bone forming activity it results in osteoporosis (loss of bone), which leads to an increased number of bone fractures, incapacitation and increased mortality. Antagonists of $\alpha_v\beta_3$ have been shown to be potent inhibitors of osteoclastic activity both in vitro [Sato et al., *J. Cell. Biol.*, Vol. 111 (1990) 1713–1723] and in vivo [Fisher et al., *Endocrinology*, Vol. 132 (1993) 1411–1413]. Antagonism of $\alpha_v\beta_3$ leads to decreased bone resorption and therefore restores a normal balance of bone forming and resorbing activity. Thus it would be beneficial to provide antagonists of osteoclast $\alpha_v\beta_3$ which are effective inhibitors of bone resorption and therefore are useful in the treatment or prevention of osteoporosis.

The role of the $\alpha_v\beta_3$ integrin in smooth muscle cell migration also makes it a therapeutic target for prevention or inhibition of neointimal hyperplasia which is a leading cause of restenosis after vascular procedures (Choi et al., J. *Vasc. Surg.* Vol. 19(1) (1994) 125–34). Prevention or inhibition of neointimal hyperplasia by pharmaceutical agents to prevent or inhibit restenosis would be beneficial.

White (*Current Biology*, Vol. 3(9)(1993) 596–599) has reported that adenovirus uses $\alpha_v\beta_3$ for entering host cells. The integrin appears to be required for endocytosis of the virus particle and may be required for penetration of the viral genome into the host cell cytoplasm. Thus compounds which inhibit $\alpha_v\beta_3$ would find usefulness as antiviral agents.

SUMMARY OF THE INVENTION

The compounds of this invention are 1) $\alpha_v\beta_3$ integrin antagonists; or 2) $\alpha_v\beta_5$ integrin antagonists; or 3) mixed or dual $\alpha_v\beta_3/\alpha_v\beta_5$ antagonists. The present invention includes compounds which inhibit the respective integrins and also includes pharmaceutical compositions comprising such compounds. The present invention further provides for methods for treating or preventing conditions mediated by the $\alpha_v\beta_3$ and/or $\alpha_v\beta_5$ receptors in a mammal in need of such treatment comprising administering a therapeutically effective amount of the compounds of the present invention and pharmaceutical compositions of the present invention. Administration of such compounds and compositions of the present invention inhibits angiogenesis, tumor metastasis, tumor growth, osteoporosis, Paget's disease, humoral hypercalcemia of malignancy, retinopathy, macular degeneration, arthritis, periodontal disease, smooth muscle cell migration, including restenosis and artherosclerosis, and viral diseases.

The compounds of the present invention further show greater selectivity for the $\alpha_v\beta_3$ and/or $\alpha_v\beta_5$ integrin than for the $\alpha_v\beta_6$ integrin. It has been found that the selective antagonism of the $\alpha_v\beta_3$ integrin is desirable in that the $\alpha_v\beta_6$ integrin may play a role in normal physiological processes of tissue repair and cellular turnover that routinely occur in the skin and pulmonary tissue, and the inhibition of this function can be deleterious. Therefore, compounds of the present invention which selectively inihibit the $\alpha_v\beta_3$ integrin as opposed to the $\alpha_v\beta_6$ integrin have reduced side-effects associated with inhibtion of the $\alpha_v\beta_6$ integrin.

The present invention relates to a class of compounds represented by the Formula I.

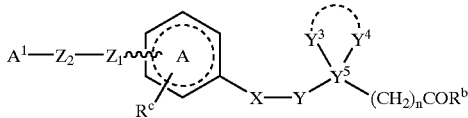

or a pharmaceutically acceptable salt thereof, wherein

is a 4–8 membered monocyclic or a 7–12 membered bicyclic ring, optionally saturated or unsaturated, optionally substituted with one or more substituent selected from the group consisting of alkyl, haloalkyl, aryl, heteroaryl, halogen, alkoxyalkyl, aminoalkyl, hydroxy, nitro, alkoxy, hydroxyalkyl, thioalkyl, amino, alkylamino, arylamino, alkylsulfonamide, acyl, acylamino, alkylsulfone, sulfonamide, alkylsulfoxide, allyl, alkenyl, methylenedioxy, ethylenedioxy, alkynyl, carboxamide, cyano, and —$(CH_2)_n$ COR wherein n is 0–2 and R is hydroxy, alkoxy, alkyl or amino;

$A^1$ is a 5–9 membered monocyclic or 7–12 membered bicyclic heterocycle of the formula

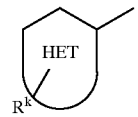

containing at least one nitrogen atom and optionally 1 to 3 additional heteroatoms, selected from the group consisting of O, N, S, CO, or $SO_2$ optionally saturated or unsaturated; optionally substituted by one or more $R^k$ selected from the group consisting of hydroxy, alkyl, cycloalkyl, alkoxy, alkoxyalkyl, thioalkyl, cyano, amino, alkylamino, halogen, acylamino, sulfonamide and —COR wherein R is hydroxy, alkoxy, alkyl or amino; or $A^1$ is

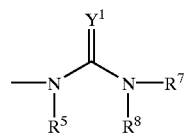

wherein $Y^1$ is selected from the group consisting of N—$R^2$, O, and S;

$R^2$ is selected from the group consisting of H; alkyl; cycloalkyl; aryl; hydroxy; alkoxy; cyano; alkenyl; alkynyl; amido; alkylcarbonyl; arylcarbonyl; alkoxycarbonyl; aryloxycarbonyl; haloalkylcarbonyl; haloalkoxycarbonyl; alkylthiocarbonyl; arylthiocarbonyl; acyloxymethoxycarbonyl;

$R^2$ taken together with $R^7$ forms a 4–12 membered dinitrogen containing heterocycle optionally substituted with one or more substituent selected from the group consisting of lower alkyl, thioalkyl, alkylamino, hydroxy, keto, alkoxy, halo, phenyl, amino, carboxyl or carboxyl ester, and fused phenyl; or $R^2$ taken together with $R^7$ forms a 4–12 membered heterocycle containing one or more heteroatom selected from O, N and S optionally unsaturated; or $R^2$ taken together with $R^7$ forms a 5 membered heteroaromatic ring fused with an aryl or heteroaryl ring;

$R^7$ (when not taken together with $R^2$) and $R^8$ are independently selected from the group consisting of H; alkyl; alkenyl; alkynyl; aralkyl; amino; alkylamino; hydroxy; alkoxy; arylamino; amido, alkylcarbonyl; arylcarbonyl; alkoxycarbonyl; aryloxy, aryloxycarbonyl; haloalkylcarbonyl; haloalkoxycarbonyl; alkylthiocarbonyl; arylthiocarbonyl; acyloxymethoxycarbonyl; cycloalkyl; bicycloalkyl; aryl; acyl; benzoyl; or $NR^7$ and $R^8$ taken together form a 4–12 membered mononitrogen containing monocyclic or bicyclic ring optionally substituted with one or more substituent selected from lower alkyl, carboxyl derivatives, aryl or hydroxy and wherein said ring optionally contains a heteroatom selected from the group consisting of O, N and S;

$R^5$ is selected from the group consisting of H, hydroxy, alkoxy, cycloalkyl, and alkyl; or

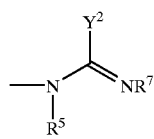

$A^1$ is wherein $Y^2$ is selected from the group consisting of alkyl; cycloalkyl; bicycloalkyl; aryl; monocyclic heterocycles;

$Z_1$ is selected from the group consisting of $CH_2$, O, $CH_2O$, $NR_k$, CO, S, SO, CH(OH) and $SO_2$, wherein $R_k$ is selected from H or lower alkyl;

$Z_2$ is a 1–5 carbon linker optionally containing one or more heteroatom selected from the group consisting of O, S and N; alternatively $Z_1$–$Z_2$ may further contain a carboxamide, sulfone, sulfonamide, alkenyl, alkynyl, or acyl group;

wherein the carbon and nitrogen atoms of $Z_1$–$Z_2$ are optionally substituted by alkyl, cycloalkyl, alkoxy, thioalkyl, alkylsulfone, aryl, arylsulfone, alkoxyalkyl, hydroxy, alkylamino, heteroaryl, alkenyl, alkynyl, carboxyalkyl, halogen, haloalkyl or acylamino;

n is an integer 1 or 2;

$R^c$ is selected from the group consisting of hydrogen, alkyl, heteroalkyl, cycloalkyl, heterocycloalkyl, halogen, hydroxy, nitro, alkoxy, amino, haloalkyl, aryl, heteroaryl, alkoxyalkyl, aminoalkyl, hydroxyalkyl, thioalkyl, alkylamino, arylamino, alkylsulfonylamino, acyl, acylamino, sulfonyl, sulfonamide, allyl, alkenyl, methylenedioxy, ethylenedioxy, alkynyl, alkynylalkyl, carboxy, alkoxycarbonyl, carboxamido, cyano, and —$(CH_2)_n$COR wherein n is 0–2 and R is selected from hydroxy, alkoxy, alkyl and amino;

X is selected from the group consisting of —$CHR^e$—, —$NR^f$—, —O—, —S—, —$SO_2$—, and —CO— wherein $R^e$ is H, lower alkyl, alkoxy, cycloalkyl, alkoxyalkyl, hydroxy, alkynyl, alkenyl, haloalkyl, thioalkyl or aryl; wherein when $R^e$ is hydroxy, the hydroxy group can optionally form a lactone with the carboxylic acid function of the chain; wherein $R^f$ is selected from the group consisting of H, alkyl, heteroalkyl, aryl, heteroaryl, aralkyl, arakylheteroaryl, and haloalkyl;

Y is selected from the group consisting of $(CH_2)_p$, —$CR^g$—, —$NR^g$, CO and $SO^2$, wherein $R^g$ is selected from the group consisting of H, alkyl, haloalkyl, alkoxyalkyl, alkynyl, aryl, heteroaryl, aralkyl, hydroxy, hydroxyalkyl, alkoxy, and carboxyalkyl; wherein p is 0 or 1;

optionally the group X—Y can contain a moiety selected from the group consisting of acyl, alkyl, sulfonyl, amino, ether, thioether, carboxamido, sulfonamido, aminosulfonyl and olefins;

$Y^3$ and $Y^4$ are independently selected from the group consisting of alkyl, haloalkyl, hydroxy, alkoxy, cyano, halogen, aralkyl, heteroaralkyl, alkoxyalkyl, hydroxyalkyl, aryloxyalkyl, alkylsulfone, alkene or alkyne; wherein the alkyl group optionally contains one or more heteroatoms selected from the group consisting of N, O, and S;

alternately, when $Y^3$ is an aryl or a heteroaryl, $Y^4$ may be an aryl, heteroaryl, alkene, alkyne, alkoxy, hydroxy, cyano, alkoxyalkyl or an alkylsulfone;

$Y^5$ is C;

Optionally, $Y^3$, $Y^4$ and $Y^5$ may form a sulfone ($SO_2$) group; or $Y^3$ taken together with $Y^4$ forms a 3–8 membered monocyclic or a 7–11 membered bicyclic ring, optionally containing one or more double bonds, optionally containing one or more heteroatom or functional group selected from O, $NR^g$, S, CO or $SO_2$, optionally substituted with one or more substituent selected from the group consisting of alkyl, heteroalkyl, hydroxy, halogen, haloalkyl, alkoxy, alkyne, cyano, alkylsulfone, sulfonamide, aryl, heteroaryl, arakylaryl, heteroarakyl arylcarboalkoxy and carboxyalkyl;

$R^b$ is $X_2$—$R^h$ wherein $X_2$ is selected from the group consisting of O, S and $NR^j$ wherein $R^h$ and $R^j$ are independently selected from the group consisting of H, alkyl, aryl, aralkyl, heteroalkyl, heteroaryl, heteroarakylaryl, acyl, and alkoxyalkyl;

It is another object of the invention to provide pharmaceutical compositions comprising compounds of the Formula I. Such compounds and compositions are useful in selectively inhibiting or antagonizing the $α_Vβ_3$ and/or $α_Vβ_5$ integrins and therefore in another embodiment the present invention relates to a method of selectively inhibiting or antagonizing the $α_Vβ_3$ and/or $α_Vβ_5$ integrin. The invention further involves treating or inhibiting pathological conditions associated therewith such as osteoporosis, humoral hypercalcemia of malignancy, Paget's disease, tumor metastasis, solid tumor growth (neoplasia), angiogenesis, including tumor angiogenesis, retinopathy including macular degeneration and diabetic retinopathy, arthritis, including rheumatoid arthritis, periodontal disease, psoriasis, smooth muscle cell migration and restenosis in a mammal in need of such treatment. Additionally, such pharmaceutical agents are useful as antiviral agents, and antimicrobials. The compounds of the present invention may be used alone or in combination with other pharmaceutical agents.

DETAILED DESCRIPTION

The present invention relates to a class of compounds represented by the Formula I, described above.

Wherein

is is a 4–8 membered monocyclic or a 7–12 membered bicyclic ring, optionally saturated or unsaturated, optionally substituted with one or more substituent selected from the group consisting of lower alkyl, alkynyl, alkenyl, halogen, alkoxy, hydroxy, cyano, amino, alkylamino, dialkylamino or methylsulfonamide.

$A^1$ is a 5–9 membered monocyclic or 7–12 membered bicyclic heterocycle of the formula

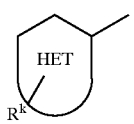

which includes the following heterocyclic ring systems containing at least one nitrogen atom:

B2
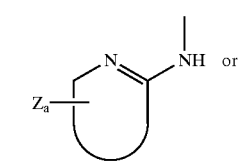 or

B3
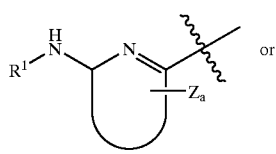 or

B4
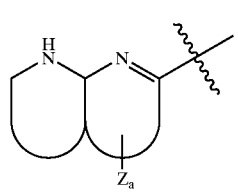

wherein $Z_a$ is H, alkyl, alkoxy, hydroxy, amine, alkylamine, dialkylamine, carboxyl, alkoxycarbonyl, hydroxyalkyl, halogen or haloalkyl and $R^1$ is H, alkyl, alkoxyalkyl, acyl, haloalkyl or alkoxycarbonyl. More specifically some examples include pyridylamino, imidazolylamino, morpholinopyridine, tetrahydronaphthyridine, oxazolylamino, thiazolylamino, pyrimidinylamino, quinoline, tetrahydroquinoline, imidazopyridine, benzimidazole, pyridone or quinolone.

The following heteroaryls include the ring systems described above.

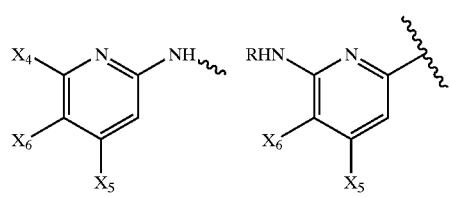

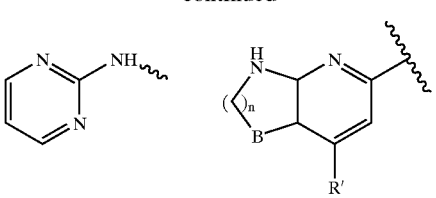

B = $CH_2$, O, CO, S, $CF_2$, $SO_2$, NR
R' = OR, OH, H, Me   n = 1 or 2

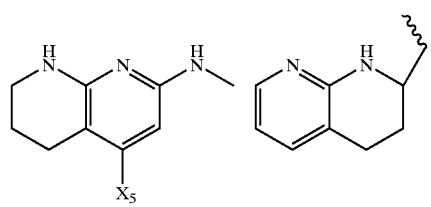

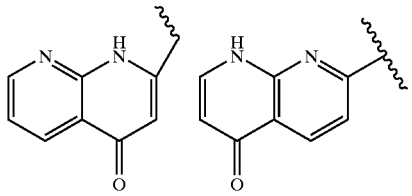

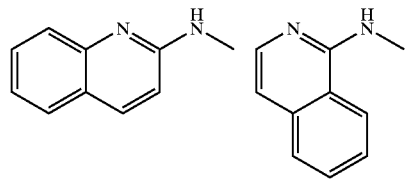

B = NH, NMe, O, S

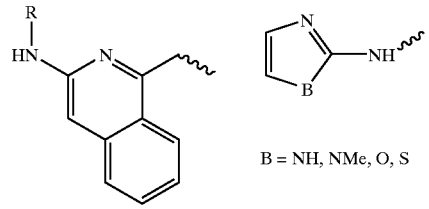

B = NH, O, S          B = N, CH

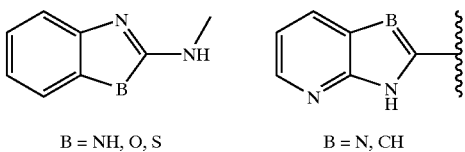

B = NH, O, S

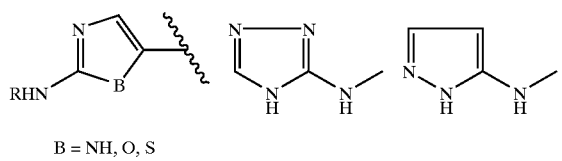

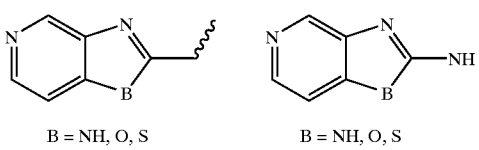

B = NH, O, S          B = NH, O, S

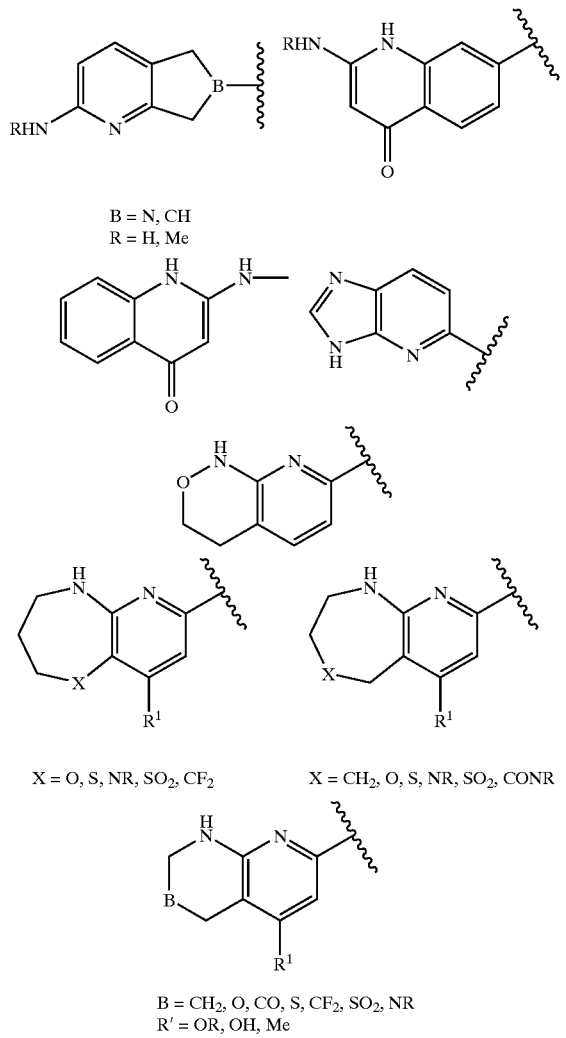

B = N, CH
R = H, Me

X = O, S, NR, SO₂, CF₂                    X = CH₂, O, S, NR, SO₂, CONR

B = CH₂, O, CO, S, CF₂, SO₂, NR
R' = OR, OH, Me

For the pyridyl derived heterocycle, the substituents $X_4$ and $X_5$ are selected from the group consisting of H, alkyl, branched alkyl, alkylamino, alkoxyalkylamino, haloalkyl, thioalkyl, halogen, amino, alkoxy, aryloxy, alkoxyalkyl, hydroxy, cyano or acylamino groups.

In another embodiment of the invention, the substituents $X_4$ and $X_5$ can be methyl, methoxy, amine, methylamine, trifluoromethyl, dimethylamine, hydroxy, chloro, bromo, fluoro and cyano. $X_6$ may preferentially be H, alkyl, hydroxy, halogen, alkoxy and haloalkyl. Alternately, the pyridyl ring can be fused with a 4–8 membered ring, optionally saturated or unsaturated. Some examples of these ring systems include tetrahydronaphthyridine, quinoline, tetrahydroquinoline, azaquinoline, morpholinopyridine, imidazopyridine and the like. The monocyclic ring systems such as imidazole, thiazole, oxazole, pyrazole, and the like, may contain an amino or alkylamino substituent at any position within the ring.

In another embodiment of the present invention, when $Z_1$ of Formula I is CO or $SO_2$, the linkage $A^1—Z_2$ of Formula I includes the heterocycle derived ring systems such as: pyridine, imidazole, thiazole, oxazole, benzimidazole, imidazopyridine and the like.

Other heterocycles for $A^1—Z_2$ of the present invention include

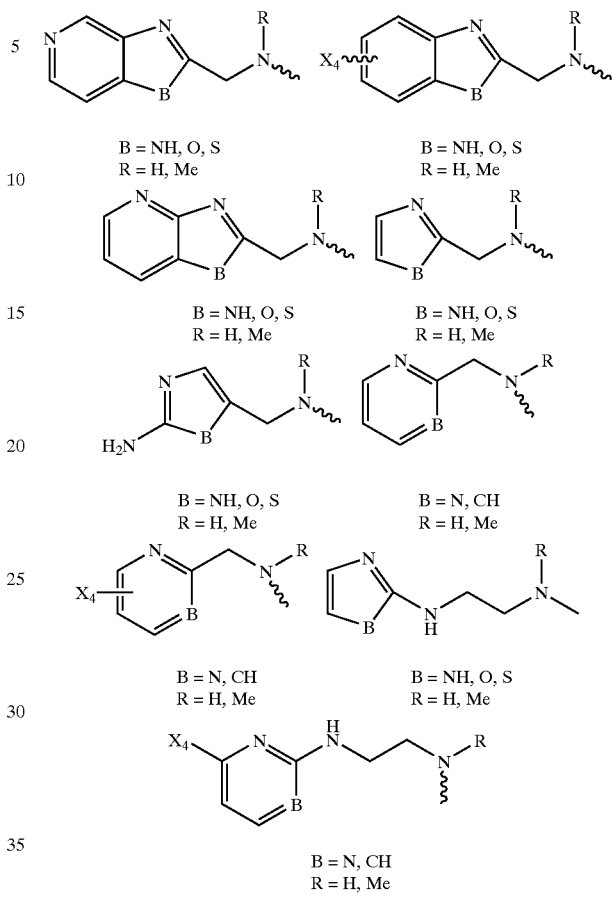

wherein
  $X_4$ is as defined above.
  $Y^3$ and $Y^4$ are as defined above; or
  $Y^3$ taken together with $Y^4$ forms a 3–8 membered monocyclic or a 7–11 membered bicyclic ring, optionally containing one or more double bonds, optionally containing one or more heteroatoms or functional groups selected from O, $NR^g$, S, CO or $SO_2$, optionally substituted with one or more substituent selected from the group consisting of alkyl, haloalkyl, halogen, haloalkyl, alkoxy, alkyne, cyano, alkylsulfone, sulfonamide, carboalkoxy and carboxyalkyl; wherein $R^g$ is selected from the group consisting of H, alkyl, haloalkyl, alkoxyalkyl, aryl, heteroaryl, aralkyl, and carboxyalkyl.

The invention further relates to pharmaceutical compositions containing therapeutically effective amounts of the compounds of Formula 1.

The invention also relates to a method of selectively inhibiting or antagonizing the $\alpha_v\beta_3$ integrin and/or the $\alpha_v\beta_5$ integrin and more specifically relates to a method of inhibiting bone resorption, periodontal disease, osteoporosis, humoral hypercalcemia of malignancy, Paget's disease, tumor metastasis, solid tumor growth (neoplasia), angiogenesis, including tumor angiogenesis, retinopathy including macular degeneration and diabetic retinopathy, arthritis, including rheumatoid arthritis, smooth muscle cell migration and restenosis by administering a therapeutically effective amount of a compound of the Formula I to achieve such inhibition together with a pharmaceutically acceptable carrier.

The following is a list of definitions of various terms used herein:

As used herein, the terms "alkyl" or "lower alkyl" refer to a straight chain or branched chain hydrocarbon radicals having from about 1 to about 10 carbon atoms, and more preferably 1 to about 6 carbon atoms. Examples of such alkyl radicals are methyl, ethyl, n-propyl, isopropyl, n-butyl, isobutyl, sec-butyl, t-butyl, pentyl, neopentyl, hexyl, isohexyl, and the like.

As used herein the terms "alkenyl" or "lower alkenyl" refer to unsaturated acyclic hydrocarbon radicals containing at least one double bond and 2 to about 6 carbon atoms, which carbon-carbon double bond may have either cis or trans geometry within the alkenyl moiety, relative to groups substituted on the double bond carbons. Examples of such groups are ethenyl, propenyl, butenyl, isobutenyl, pentenyl, hexenyl and the like.

As used herein the terms "alkynyl" or "lower alkynyl" refer to acyclic hydrocarbon radicals containing one or more triple bonds and 2 to about 6 carbon atoms. Examples of such groups are ethynyl, propynyl, butynyl, pentynyl, hexynyl and the like.

The term "cycloalkyl" as used herein means saturated or partially unsaturated cyclic carbon radicals containing 3 to about 8 carbon atoms and more preferably 4 to about 6 carbon atoms. Examples of such cycloalkyl radicals include cyclopropyl, cy clopropenyl, cyclobutyl, cyclopentyl, cyclohexyl, 2-cyclohexen-1-yl, and the like.

The term "aryl" as used herein denotes aromatic ring systems composed of one or more aromatic rings. Preferred aryl groups are those consisting of one, two or three aromatic rings. The term embraces aromatic radicals such as phenyl, pyridyl, naphthyl, thiophene, furan, biphenyl and the like.

As used herein, the term "cyano" is represented by a radical of the formula 1

The terms "hydroxy" and "hydroxyl" as used herein are synonymous and are represented by a radical of the formula 2

The term "lower alkylene" or "alkylene" as used herein refers to divalent linear or branched saturated hydrocarbon radicals of 1 to about 6 carbon atoms.

As used herein the term "alkoxy" refers to straight or branched chain oxy containing radicals of the formula —OR$^{20}$, wherein R$^{20}$ is an alkyl group as defined above. Examples of alkoxy groups encompassed include methoxy, ethoxy, n-propoxy, n-butoxy, isopropoxy, isobutoxy, sec-butoxy, t-butoxy and the like.

As used herein the terms "arylalkyl" or "aralkyl" refer to a radical of the formula

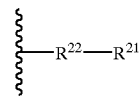

3 wherein R$^{21}$ is aryl as defined above and R$^{22}$ is an alkylene as defined above. Examples of aralkyl groups include benzyl, pyridylmethyl, naphthylpropyl, phenethyl and the like.

As used herein the term "nitro" is represented by a radical of the formula 4

As used herein the term "halo" or "halogen" refers to bromo, chloro, fluoro or iodo.

As used herein the term "haloalkyl" refers to alkyl groups as defined above substituted with one or more of the same or different halo groups at one or more carbon atom. Examples of haloalkyl groups include trifluoromethyl, dichloroethyl, fluoropropyl and the like.

As used herein the term "carboxyl" or "carboxy" refers to a radical of the formula —COOH.

As used herein the term "carboxyl ester" refers to a radical of the formula —COOR$^{23}$ wherein R$^{23}$ is selected from the group consisting of H, alkyl, heteroalkyl, heteroaryl, heteroaralkylalkyl, aralkyl or aryl as defined above.

As used herein the term "carboxyl derivative" refers to a radical of the formula

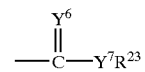

5 wherein Y$^6$ and Y$^7$ are independently selected from the group consisting of O, N or S and R$^{23}$ is selected from the group consisting of H, alkyl, aralkyl, heteroalkyl, heteroaryl, heteroaralkylalkyl or aryl as defined above.

As used herein the term "amino" is represented by a radical of the formula —NH$_2$.

As used herein the term "alkylsulfonyl" or "alkylsulfone" refers to a

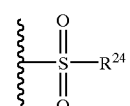

radical of the formula 6 wherein R$^{24}$ is alkyl, cycloalkyl, heteroalkyl or heterocycloalkyl as defined above.

As used herein the term "alkylthio" refers to a radical of the formula —SR$^{24}$ wherein R$^{24}$ is alkyl or heteroalkyl as defined above.

As used herein the term "sulfonic acid" refers to a radical of the

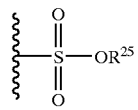

formula 7 wherein $R^{25}$ is alkyl, cycloalkyl, heteroalkyl, hetero-cycloalkyl as defined above.

As used herein the term "sulfonamide" or "sulfonamido" refers to a radical of the formula

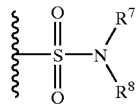

8 wherein $R^7$ and $R^8$ are as defined above.

As used herein the term "fused aryl" refers to an aromatic ring such as the aryl groups defined above fused to one or more phenyl rings.

Embraced by the term "fused aryl" is the radical naphthyl and the like.

As used herein the terms "monocyclic heterocycle" or "monocyclic heterocyclic" refer to a monocyclic ring containing from 4 to about 12 atoms, and more preferably from 5 to about 10 atoms, wherein 1 to 3 of the atoms are heteroatoms selected from the group consisting of oxygen, nitrogen and sulfur with the understanding that if two or more different heteroatoms are present at least one of the heteroatoms must be nitrogen. Representative of such monocyclic heterocycles are imidazole, furan, pyridine, oxazole, pyran, triazole, thiophene, pyrazole, thiazole, thiadiazole, and the like.

As used herein the term "fused monocyclic heterocycle" refers to a monocyclic heterocycle as defined above with a benzene fused thereto. Examples of such fused monocyclic heterocycles include benzofuran, benzopyran, benzodioxole, benzothiazole, benzothiophene, benzimidazole and the like.

As used herein the term "methylenedioxy" refers to the radical

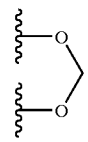

and the term "ethylenedioxy" refers to the radical

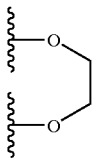

of the formula 9 and 10. As used herein the term "4–12 membered dinitrogen containing heterocycle refers to a radical of the formula

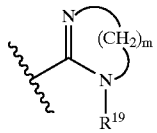

11 wherein m is 1–4 and $R^{19}$ is H, alkyl, aryl, heteroalkyl, heteroaryl, heteroaralkyl, alkyl or aralkyl and more preferably refers to 4–9 membered ring and includes rings such as imidazoline.

As used herein the term "5-membered optionally substituted heteroaromatic ring" includes for example a radical of the formula

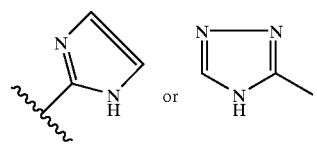

and "5-membered heteroaromatic ring fused with a phenyl" refers to such a "5-membered heteroaromatic ring" with a phenyl fused thereto. Representative of such 5-membered heteroaromatic rings fused with a phenyl is benzimidazole.

As used herein the term "bicycloalkyl" refers to a bicyclic hydrocarbon radical containing 6 to about 12 carbon atoms which is saturated or partially unsaturated.

As used herein the term "acyl" refers to a radical of the formula

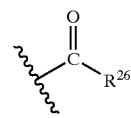

12 wherein $R^{26}$ is alkyl, cycloalkyl, alkenyl, alkynyl, aryl, hetero alkyl, heterocycloalkyl, or aralkyl and optionally substituted thereon as defined above. Encompassed by such radical are the groups acetyl, benzoyl and the like.

As used herein the term "thio" refers to a radical of the formula

As used herein the term "sulfonyl" refers to a radical of the formula

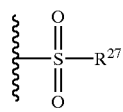

14 wherein $R^{27}$ is alkyl, aryl, heteroalkyl, heteroaryl, heteroaralkylalkyl or aralkyl as defined above.

As used herein the term "haloalkylthio" refers to a radical of the formula —S—$R^{28}$ wherein $R^{28}$ is haloalkyl as defined above.

As used herein the term "aryloxy" refers to a radical of the formula

15 wherein $R^{29}$ is aryl or heteroaryl as defined above.

As used herein the term "acylamino" refers to a radical of the formula

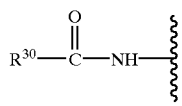

wherein $R^{30}$ is alkyl, heteroalkyl, heteroaryl, heteroaralkylalkyl, aralkyl or aryl as defined above.

As used herein the term "amido" refers to a radical of the formula

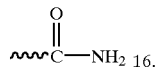 16.

As used herein the term "alkylamino" refers to a radical of the formula —$NHR^{32}$ wherein $R^{32}$ is alkyl or heteroalkyl as defined above.

As used herein the term "dialkylamino" refers to a radical of the formula —$NR^{33}R^{34}$ wherein $R^{33}$ and $R^{34}$ are the same or different alkyl or cycloalkyl groups as defined above.

As used herein the term "trifluoromethyl" refers to a radical of the formula

17

As used herein the term "trifluoroalkoxy" refers to a radical of the formula

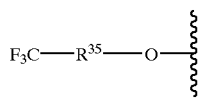

18 wherein $R^{35}$ is a bond or an alkylene as defined above.

As used herein the term "alkylaminosulfonyl" or "aminosulfonyl" refers to a radical of the formula 19

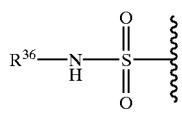

wherein is $R^{36}$ is alkyl, heteroalkyl, heteroaralkylalkyl, or heteroaryl as defined above.

As used herein the term "alkylsulfonylamino" or "alkyl-sulfonamide" refers to a radical of the formula 20

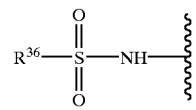

wherein $R^{36}$ is alkyl, heteroalkyl, heterocycloalkyl, or cycloalkyl as defined above.

As used herein the term "trifluoromethylthio" refers to a radical of the formula

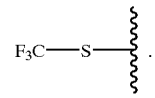

21

As used herein the term "trifluoromethylsulfonyl" refers to a radical of the formula

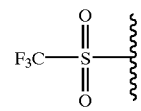

22.

As used herein the term "4–12 membered mono-nitrogen containing monocyclic or bicyclic ring" refers to a saturated or partially unsaturated monocyclic or bicyclic ring of 4–12 atoms and more preferably a mono or bicyclic ring of 4–9 atoms wherein one atom is nitrogen. Such rings may optionally contain additional heteroatoms selected from nitrogen, oxygen or sulfur. Included within this group are morpholine, piperidine, piperazine, thiomorpholine, pyrrolidine, proline, azacycloheptene and the like.

As used herein the term "benzyl" refers to the radical

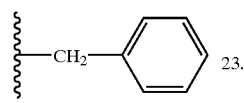

As used herein the term "phenethyl" refers to the radical

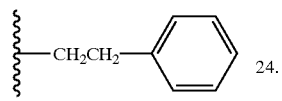

As used herein the term "4–12 membered mono-nitrogen containing monosulfur or monooxygen containing heterocyclic ring" refers to a ring consisting of 4 to 12 atoms and more preferably 4 to 9 atoms wherein at least one atom is a nitrogen and at least one atom is oxygen or sulfur. Encompassed within this definition are rings such as thiazoline and the like.

As used herein the term "arylsulfonyl" or "arylsulfone" refers to a radical of the formula 25

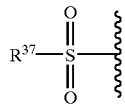

wherein $R^{37}$ is aryl as defined above.

As used herein the terms "alkylsulfoxide" or "arylsulfoxide" refer to radicals of the formula

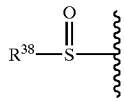

26 wherein $R^{38}$ is, respectively, alkyl, heteroalkyl, heteroaryl or aryl as defined above.

As used herein the term "arylthio" refers to a radical of the formula 27

wherein $R^{42}$ is aryl as defined above.

As used herein the term "monocyclic heterocycle thio" refers to a radical of the formula

28 wherein $R^{43}$ is a monocyclic heterocycle radical as defined above.

As used herein the terms "monocyclic heterocycle sulfoxide" and "monocyclic heterocycle sulfone" refer, respectively, to radicals of the formula 29 30

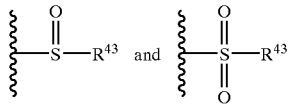

wherein $R^{43}$ is a monocyclic heterocycle radical as defined above.

As used herein the term "alkylcarbonyl" refers to a radical of the formula

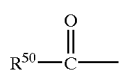

31 wherein $R^{50}$ is alkyl, heteroaryl, heterocycloaryl or cycloalkyl as defined above.

As used herein the term "arylcarbonyl" refers to a radical of the formula

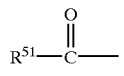

32 wherein $R^{51}$ is aryl as defined above.

As used herein the term "alkoxycarbonyl" refers to a radical of the formula

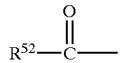

33 wherein $R^{52}$ is alkoxy as defined above.

As used herein the term "aryloxycarbonyl" refers to a radical of the formula

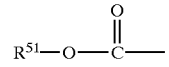

34 wherein $R^{51}$ is aryl as defined above.

As used herein the term "haloalkylcarbonyl" refers to a radical of the formula

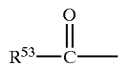

35 wherein $R^{53}$ is haloalkyl as defined above.

As used herein the term "haloalkoxycarbonyl" refers to a radical of the formula

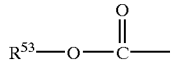

36 wherein $R^{53}$ is haloalkyl as defined above.

As used herein the term "alkylthiocarbonyl" refers to a radical of the formula

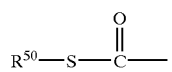

37 wherein $R^{50}$ is alkyl or cycloalkyl as defined above.

As used herein the term "arylthiocarbonyl" refers to a radical of the formula

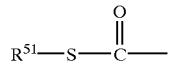

38 wherein $R^{51}$ is aryl as defined above.

As used herein the term "acyloxymethoxycarbonyl" refers to a radical of the formula

39 wherein $R^{54}$ is acyl as defined above.

As used herein the term "arylamino" refers to a radical of the formula $R^{51}$—NH— wherein $R^{51}$ is aryl as defined above.

As used herein the term "acyloxy" refers to a radical of the formula $R^{55}$—O— wherein $R^{55}$ is acyl as defined above.

As used herein the term "alkenylalkyl" refers to a radical of the formula $R^{50}$—$R^{57}$— wherein $R^{50}$ is an alkenyl as defined above and $R^{57}$ is alkylene as defined above.

As used herein the term "alkenylene" refers to a linear hydrocarbon radical of 1 to about 8 carbon atoms containing at least one double bond.

As used herein the term "alkoxyalkyl" refers to a radical of the formula $R^{56}$—$R^{57}$— wherein $R^{56}$ is alkoxy as defined above and $R^{57}$ is alkylene as defined above.

As used herein the term "alkynylalkyl" refers to a radical of the formula $R^{59}$—$R^{60}$— wherein $R^{59}$ is alkynyl as defined as above and $R^{60}$ is alkylene as defined as above.

As used herein the term "alkynylene" refers to divalent alkynyl radicals of 1 to about 6 carbon atoms.

As used herein the term "allyl" refers of a radical of the formula —$CH_2CH$=$CH_2$.

As used herein the term "aminoalkyl" refers to a radical of the formula $H_2N$—$R^{61}$ wherein $R^{61}$ is alkylene as defined above.

As used herein the term "benzoyl" refers to the aryl radical $C_6H_5$—CO—.

As used herein the term "carboxamide" or "carboxamido" refer to a radical of the formula —CO—$NH_2$.

As used herein the term "carboxyalkyl" refers to a radical HOOC—$R^{62}$— wherein $R^{62}$ is alkylene as defined as above.

As used herein the term "carboxylic acid" refers to the radical —COOH.

As used herein the term "ether" refers to a radical of the formula $R^{63}$—O— wherein $R^{63}$ is selected from the group consisting of alkyl, aryl and heteroaryl.

As used herein the term "haloalkylsulfonyl" refers to a radical of the formula

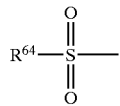

wherein the $R^{64}$ is haloalkyl as defined above.

As used herein the term "heteroaryl" refers to an aryl radical contain at least one heteroatom.

As used herein the term "hydroxyalkyl" refers to a radical of the formula HO—$R^{65}$ wherein $R^{65}$ is alkylene as defined above.

As used herein the term "keto" refers to a carbonyl group joined to 2 carbon atoms.

As used herein the term "lactone" refers to an anhydro cyclic ester produced by intramolecular condensation of a hydroxy acid with the elimination of water.

As used herein the term "olefin" refers to an unsaturated hydrocarbon radical of the type $C_nH_{2n}$.

As used herein the term "sulfone" refers to a radical of the formula $R^{66}$—$SO_2$— wherein $R^{66}$ is alkyl or cycloalkyl as defined above.

As used herein the term "thioalkyl" refers to a radical of the formula $R^{77}$—S— wherein $R^{77}$ is alkyl as defined above.

As used herein the term "thioether" refers to a radical of the formula $R^{78}$—S— wherein $R^{78}$ is alkyl, aryl or heteroaryl.

As used herein the term "trifluoroalkyl" refers to an alkyl radical as defined above substituted with three halo radicals as defined above.

The term "composition" as used herein means a product which results from the mixing or combining of more than one element or ingredient.

The term "pharmaceutically acceptable carrier", as used herein means a pharmaceutically acceptable material, composition or vehicle, such as a liquid or solid filler, diluent, excipient, solvent or encapsulating material, involved in carrying or transporting a chemical agent.

The term "therapeutically effective amount" shall mean that amount of drug or pharmaceutical agent that will elicit the biological or medical response of a tissue, system or animal that is being sought by a researcher or clinician.

The following is a list of abbreviations and the corresponding meanings as used interchangeably herein:

$^1$H-NMR=proton nuclear magnetic resonance
AcOH=acetic acid
Ar=Argon
BOC=tert-butoxycarbonyl
BuLi=butyl lithium
Cat.=catalytic amount
$CH_2Cl_2$=dichloromethane
$CH_3CN$=acetonitrile
$CH_3I$=iodomethane
CHN analysis=carbon/hydrogen/nitrogen elemental analysis
CHNCl analysis=carbon/hydrogen/nitrogen/chlorine elemental analysis
CHNS analysis=carbon/hydrogen/nitrogen/sulfur elemental analysis
DEAD=diethylazodicarboxylate
DIAD=diisopropylazodicarboxylate
DI water=deionized water
DMA=N,N-dimethylacetamide
DMAC=N,N-dimethylacetamide
DMF=N,N-dimethylformamide
EDC=1-(3-dimethylaminopropyl)-3-ethylcarbodiimide hydrochloride
Et=ethyl
EtI=ethyl iodide
$Et_2O$=diethyl ether
$Et_3N$=triethylamine
EtOAc=ethyl acetate
EtOH=ethanol
FAB MS=fast atom bombardment mass spectroscopy
g=gram(s)
HCl=hydrochloric acid
HOBT=1-hydroxybenzotriazole hydrate
hplc=high performance liquid chromatography
HPLC=high performance liquid chromatography
IPA=isopropyl alcohol
i-Pr=iso propyl
i-Prop=iso propyl
$K_2CO_3$=potassium carbonate
KF=potassium fluoride
kg=kilogram
KH—potassium hydride
$KMnO_4$=potassium permanganate
KOH=potassium hydroxide
KSCN=potassium thiocyanate
L=Liter
LDA=Lithium Diisopropylamide
LiOH=lithium hydroxide
LTMP=Lithium tetramethylpiperidide
Me=methyl
MeOH=methanol
mg=milligram
$MgSO_4$=magnesium sulfate
ml=milliliter
mL=milliliter MS=mass spectroscopy
NaH—sodium hydride
NaHCO$_3$=sodium bicarbonate
NaOH=sodium hydroxide
NaOMe=sodium methoxide
NH$_4^+$HCO$_2^-$=ammonium formate
NH$_4$OH=ammonium hydroxide
NMR=nuclear magnetic resonance
Pd=palladium
Pd/C=palladium on carbon
Ph=phenyl
psi=pressure per square inch
Pt=platinum
Pt/C=platinum on carbon
RP HPLC=reverse phase high performance liquid chromatography
RT=room temperature
t-BOC=tert-butoxycarbonyl
TEA=triethylamine
TFA=trifluoroacetic acid
THF=tetrahydrofuran
TLC—thin layer chromatography
TMS=trimethylsilyl
Δ=heating the reaction mixture The compounds as shown above can exist in various isomeric forms and all such isomeric forms are meant to be included. Tautomeric forms are also included as well as pharmaceutically acceptable salts of such isomers and tautomers.

In the structures and formulas herein, a bond drawn across a bond of a ring can be to any available atom on the ring. a ring can be to any available atom on the ring.

The term "pharmaceutically acceptable salt" refers to a salt prepared by contacting a compound of Formula I with an acid whose anion is generally considered suitable for human consumption. Examples of pharmacologically acceptable salts include the hydrochloride, hydrobromide, hydroiodide, sulfate, phosphate, propionate, lactate, maleate, malate, succinate, tartrate salts and the like. Furthermore, where the compounds of the invention carry an acidic moiety, suitable pharmaceutically acceptable salts thereof may include alkali metal salts, e.g., sodium or potassium salts; or alkaline earth metal salts. All of the pharmacologically acceptable salts may be prepared by conventional means. (See Berge et al., *J Pharm. Sci*, 66(1), 1–19 (1977) for additional examples of pharmaceutically acceptable salts.)

The present invention includes within its scope prodrugs of compounds of Formula I. These prodrugs are typically derivatives of the compounds of Formula I which are convertible to the active compounds on in-vivo exposure. These compounds may be derivatives of carboxylic acid (such as ester, amide, orthoester, urea and the like). Similarly derivatives of amine, hydroxy or other functional groups may be used as handles for prodrug formation. Thus in the present invention, administering a compound for treatment of various conditions would include compounds specifically disclosed or the compounds which may not be specifically disclosed but would be converted to the specifically disclosed compound of Formula 1 on in-vivo administration. The methods described in literature (e.g., Design of prodrugs, H. Bundgaard, Elsevier, 1985; Annual reports in Medicinal Chemistry, Vol 10, R. V. Heinzelman, ed.: Academic Press, 306–326, 1975) may be used for the preparation of prodrugs.

The compounds of the present invention may be chiral or achiral. These compounds may exist as racemic mixtures, diastereomers or pure enantiomers. For a chiral compound of present invention, separate enantiomers or all mixtures of diastereomers are included.

For the selective inhibition or antagonism of $\alpha_V\beta_3$ and/or $\alpha_V\beta_5$ integrins, compounds of the present invention may be administered orally, parenterally, or by inhalation spray, or topically in unit dosage formulations containing conventional pharmaceutically acceptable carriers, adjuvants and vehicles. The term parenteral as used herein includes, for example, subcutaneous, intravenous, intramuscular, intrasternal, transmuscular infusion techniques or intraperitonally.

The compounds of the present invention are administered by any suitable route in the form of a pharmaceutical composition adapted to such a route, and in a dose effective for the treatment intended. Therapeutically effective doses of the compounds required to prevent or arrest the progress of or to treat the medical condition are readily ascertained by one of ordinary skill in the art using preclinical and clinical approaches familiar to the medicinal arts.

Accordingly, the present invention provides a method of treating conditions mediated by selectively inhibiting or antagonizing the $\alpha_V\beta_3$ and/or $\alpha_V\beta_5$ cell surface receptor which method comprises administering a therapeutically effective amount of a compound selected from the class of compounds depicted in the above formulas, wherein one or more compound is administered in association with one or more non-toxic, pharmaceutically acceptable carriers and/or diluents and/or adjuvants (collectively referred to herein as "carrier" materials) and if desired other active ingredients. More specifically, the present invention provides a method for inhibition of the $\alpha_V\beta_3$ and/or $\alpha_V\beta_5$ cell surface receptors. Most preferably the present invention provides a method for inhibiting bone resorption, treating osteoporosis, inhibiting humoral hypercalcemia of malignancy, treating Paget's disease, inhibiting tumor metastasis, inhibiting neoplasia (solid tumor growth), inhibiting angiogenesis including tumor angiogenesis, treating retinopathy including macular degeneration and diabetic retinopathy, inhibiting arthritis, psoriasis and periodontal disease, and inhibiting smooth muscle cell migration including restenosis.

Based upon standard laboratory experimental techniques and procedures well known and appreciated by those skilled in the art, as well as comparisons with compounds of known usefulness, the compounds of Formula I can be used in the treatment of patients suffering from the above pathological conditions. One skilled in the art will recognize that selection of the most appropriate compound of the invention is within the ability of one with ordinary skill in the art and will depend on a variety of factors including assessment of results obtained in standard assay and animal models.

Treatment of a patient afflicted with one of the pathological conditions comprises administering to such a patient an amount of compound of the Formula I which is therapeutically effective in controlling the condition or in prolonging the survivability of the patient beyond that expected in the absence of such treatment. As used herein, the term "inhibition" of the condition refers to slowing, interrupting, arresting or stopping the condition and does not necessarily indicate a total elimination of the condition. It is believed that prolonging the survivability of a patient, beyond being a significant advantageous effect in and of itself, also indicates that the condition is beneficially controlled to some extent.

As stated previously, the compounds of the invention can be used in a variety of biological, prophylactic or therapeutic areas. It is contemplated that these compounds are useful in prevention or treatment of any disease state or condition wherein the $\alpha_v\beta_3$ and/or $\alpha_v\beta_5$ integrin plays a role.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary widely. Dosage levels of the order from about 0.01 mg to about 100 mg per kilogram of body weight per day are useful in the treatment of the above-indicated conditions.

Oral dosages of the present invention, when used for the indicated effects, will range between about 0.01 mg per kg of body weight per day (mg/kg/day) to about 100 mg/kg/day, preferably 0.01 to 10 mg/kg/day, and most preferably 0.1 to 1.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100, 200 and 500 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. Intravenously, the most preferred doses will range from about 0.1 to about 10 mg/kg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regiment.

For administration to a mammal in need of such treatment, the compounds in a therapeutically effective amount are ordinarily combined with one or more adjuvants appropriate to the indicated route of administration. The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulphuric acids, gelatin, acacia, sodium alginate, polyvinylpyrrolidone, and/or polyvinyl alcohol, and tableted or encapsulated for convenient administration. Alternatively, the compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

The pharmaceutical compositions useful in the present invention may be subjected to conventional pharmaceutical operations such as sterilization and/or may contain conventional pharmaceutical adjuvants such as preservatives, stabilizers, wetting agents, emulsifiers, buffers, etc.

In another embodiment, the present invention provides treatment or prevention of a neoplasia disease in a mammal by combining one or more $\alpha_v\beta_3$ integrin antagonists of the present invention with one or more chemotherapeutic agents. Among chemotherapeutic agents that may be used in combination with the $\alpha_v\beta_3$ antagonist compounds include but are not limited to 5-fluorouacil, cyclophosphamide, cisplatin, taxol, and doxorubicin are preferred. Other chemotherapeutics useful in combination and within the scope of the present invention include but are not limited to buserelin, topoisomerase inhibitors such as topotecan and irinotecan, mitoxantrone, BCNU, CPT-11, chlorotranisene, chromic phosphate, gemcitabine, dexamethasone, estradiol, estradiol valerate, estrogens conjugated and esterified, estrone, ethinyl estradiol, floxuridine, goserelin, hydroxyurea, carboplatin, melphalan, methotrexate, mitomycin and prednisone.

The methods and combinations using one provide treatment or prevention of a neoplasia disease in a mammal using one or more $\alpha_v\beta_3$ integrin antagonists described above with one or more chemotherapeutic agents described above. The method comprises treating a mammal with a therapeutically effective amount of an $\alpha_v\beta_3$ integrin antagonist in combination with a chemotherapeutic agent.

There are five major classes of chemotherapeutic agents currently in use for the treatment of cancer: natural products and their derivatives; anthracyclins; alkylating agents; antimetabolites; and hormonal agents. Chemotherapeutic agents are often referred to as antineoplastic agents. The alkylating agents are believed to act by alkylating and cross-linking guanine and possibly other bases.

In DNA, arresting cell division. Typical alkylating agents include nitrogen mustards, ethyleneimine compounds, alkyl sulfates, cislatin, and various nitrosoureas. A disadvantage with these compounds is that they not only attack malignant cells, but also other cells which are naturally dividing, such as those of bone marrow, skin, gastro-intestinal mucosa and fetal tissue.

Antimetaloties are typically reversible or irreversible enzyme inhibitors, or compounds that otherwise interfere with the replication, translation or transcription of nucleic acids. Several synthetic nucleosides have been identified that exhibit anticancer activity. A well-known nucleoside derivative with strong anticancer activity is 5-fluorouacil. 5-fluorouacil has been used clinically in the treatment of malignant tumors, including, for example, carcinomas, sarcomas, skin cancer, cancer of the digestive organs, and breast cancer. 5-fluoroucil, however, causes serious adverse reactions such as nausea, alopecia, stomatites, leukocytic thrombocytopenia, anorexia, pigmentation and edema.

Cytosine arabinoside (also referred to as Cytarabin, araC, and Cytosar) is a nucleoside analog of deoxycytidine that was first synthesized in 1950 and introduced into clinical medicine in 1963. It is currently an important drug in the treatment of acute myeloid leukemia. It is also active against acute lymphocytic leukemia, and to a lesser extent, is useful in chronic myelocytic leukemia and non-Hodgkin's lymphoma.

The following table (Table 1) provides illustrative examples of median dosages for selected cancer agents that may be used in combination with a $\alpha_v\beta_3$ integrin antagonist agent. It should be noted that the specific dose regimen for the chemotherapeutic agents below will depend upon dosing considerations based upon a variety of factors including the type of neoplasia; the state of the neoplasm, the age, weight, sex and medical condition of the patient; the route of administration, the renal and hepatic function of the patient; and the particular combination employed.

TABLE 1

| NAME OF CHEMOTHERAPEUTIC AGENT | |
|---|---|
| Asparaginase | 10,000 units |
| Bleomycin Sulfate | 15 Units |
| Carboplatin | 50–450 mg |
| Carmustine | 100 mg. |
| Cisplatin | 10–50 mg. |
| Cladribine | 10 mg. |
| Cyclophosphmide (lyophilized) | 100 mg.–2 gm. |
| Cyclophosphamide (non-lyophilized) | 100 mg.–2 gm. |
| Cytarabine (lyophilized powder) | 100 mg.–2 gm. |
| Dacarbazine | 100 mg.–200 mg. |
| Dactinomycin | 0.5 mg. |
| Daunorubicin | 20 mg. |
| Diethylstilbestrol | 250 mg. |
| Doxorubin | 10–150 mg. |
| Etidronate | 300 mg. |
| Etoposide | 100 mg. |
| Floxuridine | 500 mg. |
| Fludarabine Phosphate | 50 mg. |
| Fluorouracil | 500 mg.–5 gm. |
| Goserelin | 3.6 mg. |
| Granisetron Hydrochloride | 1 mg. |
| Idarubicin | 5–10 mg. |
| Ifosfamide | 1–3 gm. |
| Leucovorin Calcium | 50–350 mg. |
| Leuprolide | 3.75–7.5 mg. |
| Mechlorethamine | 10 mg. |
| Medroxyprogeserone | 1 gm. |
| Melphalan | 50 gm. |

TABLE 1-continued

| NAME OF CHEMOTHERAPEUTIC AGENT | |
|---|---|
| Methotrexate | 20 mg.–1 gm. |
| Mitomycin | 5–40 mg. |
| Mitoxantrone | 20–30 mg. |
| Ondansetron Hydrochloride | 40 mg. |
| Paclitaxel | 30 mg. |
| Pamidronate Disodium | 30–90 mg. |
| Pegaspargase | 750 units |
| Pilcamyican | 2,500 mcgm. |
| Streptozocin | 1 gm. |
| Thiotepa | 15 mg. |
| Teniposide | 50 mg. |
| Vinblastine | 10 mg. |
| Vincristine | 1–5 mg. |

The pharmaceutical compositions useful in the present invention may be subjected to conventional pharmaceutical operations such as sterilization and/or may contain conventional pharmaceutical adjuvants such as preservatives, stabilizers, wetting agents, emulsifiers, buffers, etc.

The general synthetic sequences for preparing the compounds useful in the present invention are outlined in SCHEMES 1–3. Both an explanation of, and the actual procedures for, the various aspects of the present invention are described where appropriate. The following Schemes and Examples are intended to be merely illustrative of the present invention, and not limiting thereof in either scope or spirit. Those with skill in the art will readily understand that known variations of the conditions and processes described in the Schemes and Examples can be used to synthesize the compounds of the present invention.

Unless otherwise indicated all starting materials and equipment employed were commercially available.

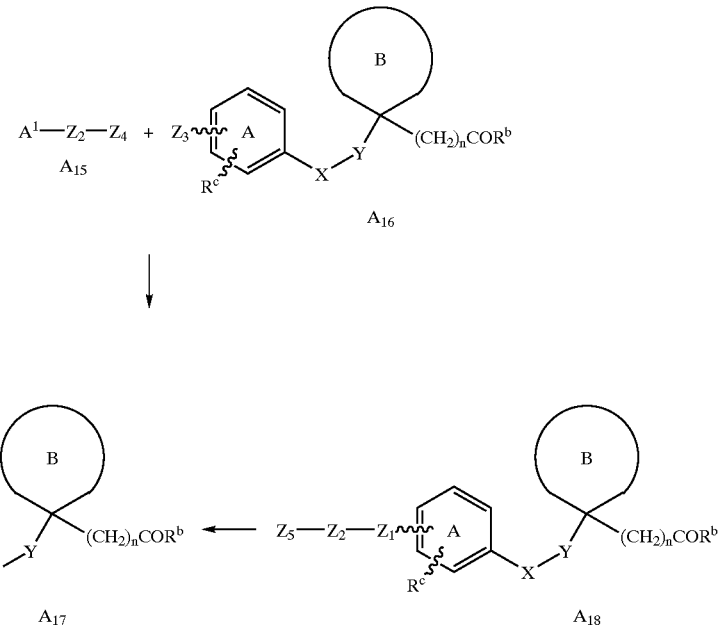

SCHEME 1

Scheme 1

The compounds of formula $A_{17}$ are generally prepared by reacting an intermediate of formula $A_{16}$ with a compound of the formula $A_{15}$. For example, when $Z_3$ is a OH, SH or NHR group, $A_{16}$ may be alkylated with $A_{15}$ ($Z_4$=Br or OMs) using a base such as sodium hydride, potassium hydride and preferably in a solvent such as dimethylsulfoxide or DMF. These reactions may preferentially be carried at 0° C. to approximately 40° C. Alternately, when $Z_3$ and $Z_4$ are both OH, the ether formation to product $A_{17}$ may be accomplished by using Mitsunobu reaction. This reaction may preferentially be carried out using triarylphosphine (such as triphenylphoshine) and azodicarboxylate (such as diethyl azodicarboxylate, di-tert-butyl azodicarboxylate, di-isopropyl azodicarboxylate) in solvents such as DMF, methylene chloride, THF and the like. When $Z_3$ carries a carboxylic acid or a sulfonic acid and $Z_4$ is an amine, the standard coupling conditions may be used to synthesize the carboxamide (CONH) or the sulfonamide ($SO_2NH$) containing targets $A_{17}$.

Alternately, the compounds of formula $A_{17}$ may be prepared by starting with compounds of general formula $A_{18}$. For example, when $Z_5$ in $A_{18}$ is $NH_2$, cyclic or acyclic guanidino containing compounds of formula $A_{17}$ may be synthesized by adopting the methodologies discussed in e.g. U.S. Pat. Nos. 5,852,210 or 5,773,646. Similarly, compounds of formula $A_{18}$ ($Z_5$=$NH_2$) may be treated with appropriately substituted heteroaromatic system (such as 2-fluoropyridine or 2-chloropyridine N-oxide) to give the target compounds $A_{17}$. This reaction may preferentially be carried out by refluxing the intermediate $A_{18}$ and 2-halopyridine N-oxide (such as 2-chloropyridine N-oxide) in solvents such as tert-butyl alcohol, tert-amyl alcohol in the presence of a base (such as sodium bicarbonate, sodium carbonate, potassium carbonate, potassium bicarbonate).

Compounds of the general formula $A_{15}$, $A_{16}$, $A_{18}$ may be prepared by methodologies discussed hereinafter.

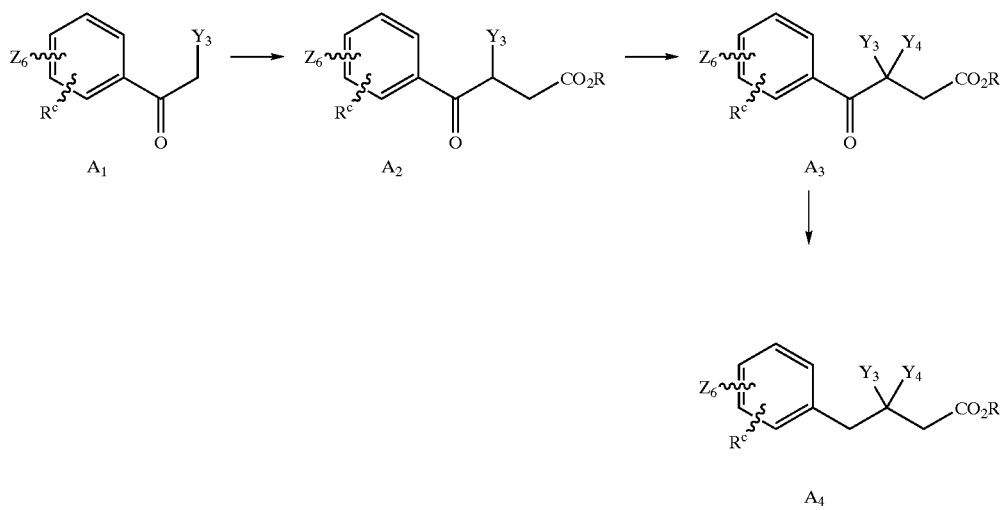

SCHEME 2

R = H or alkyl

Scheme 2

Compounds of the formula $A_4$ containing a methyl substituent may be prepared by starting with substituted propiophenone $A_1$. Generation of enolate with a base (such as HMDS, LDA, NaH, KH) at low temperature (−78°–0° C.) followed by quenching with an electrophile such as ethyl bromoacetate gives the intermediates $A_2$. Base hydrolysis of the ester (using e.g; 1N NaOH) followed by repetition of the enolate chemistry using excess of a base (such as HMDS, LDA, NaH, KH) followed by reaction with electrophile (such as alkyl iodide, or benzyl halide) gives the intermediate $A_3$. Esterification of the resulting acid with an alcohol in the presence of drops of acid gives the desired ester intermediate $A_3$. Deoxygenation of carbonyl group gives the intermediate $A_4$. This transformation may be carried out using catalytic hydrogenation conditions in the presence of an acid (such as phosphoric acid). Palladium on carbon and hydrogen under 5–60 psi can be used to achieve this reduction. The intermediates $A_3$ and $A_4$ are processed to the target compounds of Formula I by synthetic transformations outlined in Scheme 1.

SCHEME 3

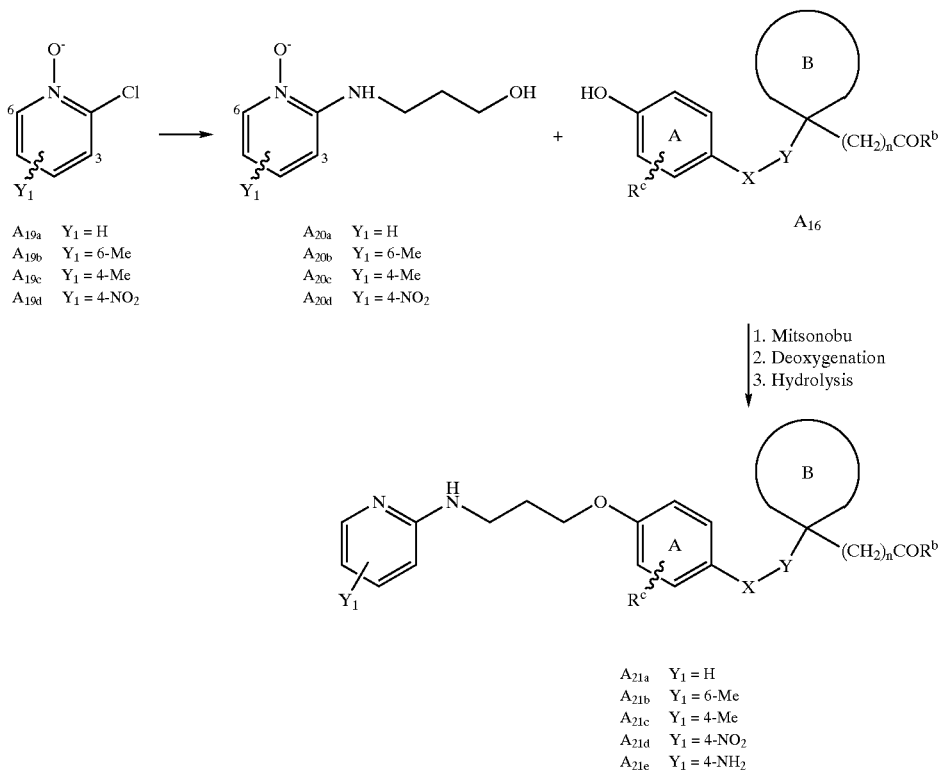

Scheme 3

The compounds of Formula I, wherein A is substituted pyridyl may be prepared by adopting the general synthetic Scheme 3. For example, reaction of substituted 2-halopyridine N-oxide (such as $A_{19a}$–$A_{19d}$) with e.g. 3-aminopropanol gives the intermediates $A_{20a}$–$A_{20d}$. This reaction may preferentially be carried out by refluxing the intermediate 2-halopyridine N-oxide (such as 2-chloropyridine N-oxide) in solvents such as tert-butyl alcohol, tert-amyl alcohol in the presence of base (such as sodium bicarbonate, sodium carbonate, potassium carbonate, potassium bicarbonate). The preparative conditions described in WO 99/15508 (PCT US 98/19466) may be used for this transformation. Coupling of the intermediates $A_{20a}$–$A_{20d}$ with $A_{16}$ using Mitsunobu reaction gives the compounds containing the ether link. This reaction may preferentially be carried out using triarylphosphine (such as triphenylphoshine) and dialkyl azodicarboxylate (such as diethyl azodicarboxylate, di-tert-butyl azodicarboxylate, di-iso-propyl azodicarboxylate) in solvents such as DMF, methylene chloride, or THF. N-Deoxygenation of the resulting intermediates followed by hydrolysis of the ester gives the target compounds ($A_{21a}$–$A_{21d}$). Reduction of the N-oxide bond may be accomplished using e.g., transfer hydrogenation (cyclohexene/Pd on carbon) or ammonium formate and Pd on carbon or iron powder and acetic acid. The nitro group in $21_d$ may be hydrogenated using Pd on carbon or Pt on carbon as catalysts. This transformation may be carried out using solvents such as methanol, ethanol or THF. The hydrolysis of the ester group may be carried out using aqueous base (such as sodium hydroxide, lithium hydroxide or potassium hydroxide) in solvents such as methanol, ethanol and THF.

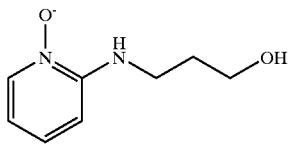

Example A

2-[3-Hydroxy-1-propyl)amino]pyridine-N-oxide

A mixture of 2-chloropyridine-N-oxide (16.6 g, 100 mmole), 3-amino-1-butanol (15.3 ml, 200 mmole), NaHCO$_3$ (42 g, 0.5 mole), and tert-amyl alcohol (100 ml) was heated to reflux. After 23 hours, the reaction was cooled, diluted with CH$_2$Cl$_2$ (300 ml), and filtered to remove insoluble materials. The filtrate was concentrated to afford a brown oil. The oil was dried under vacuum overnight. The ether (100 ml) was added to give a brown solid. The ether was decanted and the solid was washed further with ether/acetonitrile (3/1). The resulting solid was heated at 67° C. under vacuum to give the desired product (13.5 g). $^1$H NMR was consistent with the proposed structure.

EXAMPLE 1

1-[2-oxo-2-[4-[3-(2-pyridinylamino)propoxy]phenyl]ethyl]cyclopentaneacetic Acid

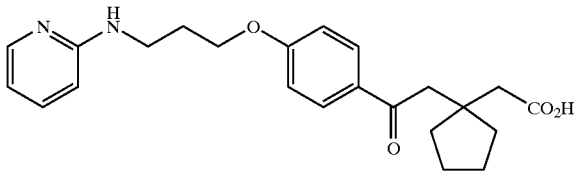

Step 1

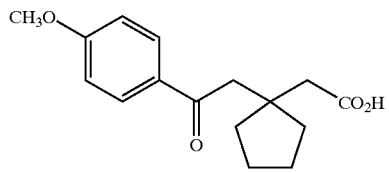

In a flame dried flask under nitrogen was placed a solution of 5.0 g of 3,3-tetramethylene glutaric anhydride in 25 mL of THF. The solution was chilled to −65 degrees and 59.4 mL of a solution of 4-methoxyphenyl magnesium bromide (0.5 M in THF) was added dropwise. The reaction was stirred at 65 degrees for 2 hours and then quenched with 100 mL of saturated aqueous ammonium chloride solution. The layers were separated and the aqueous portion was extracted well with ethyl acetate. The combined organic extracts were washed with brine, dried over $Na_2SO_4$, concentrated and purified on a silica gel column eluting with 1:1 ethyl acetate/hexane to produce a viscous oil (5.1 g). The $^1H$ NMR spectra was consistent with the proposed structure.

Step 2

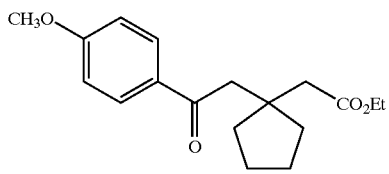

A solution of the product from STEP 1 (5.0 g), ethanol (50 mL) and 4N HCl in dioxane (50 mL) was stirred at room temperature overnight. The reaction was concentrated and the residue was purified on a silica gel column eluting with 25% ethyl acetate/hexane to afford a liquid (4.6 g). The $^1H$ NMR spectra was consistent with the proposed structure.

Step 3

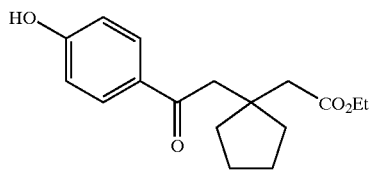

To a solution of the product from STEP 2 (4.5 g), in methylene chloride was added boron tribromide (1.0 M solution in $CH_2Cl_2$) over 10 minutes at room temperature. After standing for one hour the reaction was quenched with ethanol and concentrated. The residue was partitioned between ethyl acetate and 10% $NaHCO_3$ solution. The aqueous portion was extracted with additional solvent and the combined organic extracts were washed with brine, dried over $Na_2SO_4$, concentrated, and the residue purified on a silica gel column eluting with 25% ethyl acetate/hexane to afford an oil (2.5 g). The $^1H$ NMR spectra was consistent with the proposed structure.

Step 4

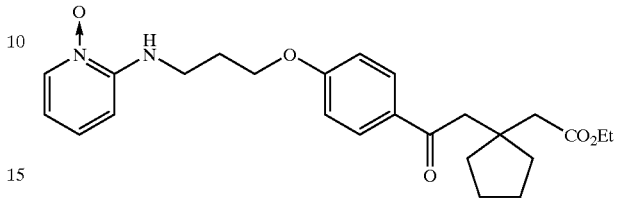

To a solution of the product from STEP 3 (450 mg), in DMF (20 ml) under nitrogen was added 2-[3-(hydroxy-1-propyl)amino]pyridine-N-oxide (470 mg) and triphenylphosphine (459 mg). The solution was stirred at room temperature for several minutes and then a solution of diethyl azodicarboxylate (305 mg) in DMF (5 ml) was added dropwise. The reaction was stirred for 18 hours and the solvent was removed in vacuo. The residue was purified on a silica gel column eluting with 98% $CH_2Cl_2$—1.5% $CH_3OH$—0.5% $NH_4OH$ to produce a golden oil (240 mg). The $^1H$ NMR was consistent with the proposed structure.

Step 5

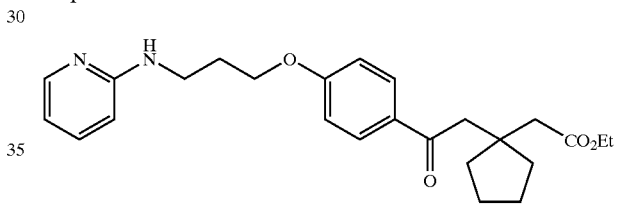

A mixture of the product from STEP 4 (225 mg), 10% Pd/C (approximately 200 mg) and cyclohexene (approximately 1.5 ml) and isopropanol (10 ml) was refluxed for 8 hours under nitrogen. The reaction was cooled, filtered through a pad of celite and washed with excess isopropanol. The filtrate was concentrated and the residue was purified on a silica gel column eluting with 98% $CH_2Cl_2$—1.5% $CH_3OH$ 0.5% $NH_4OH$ to afford a viscous oil (120 mg). The $^1H$ NMR was consistent with the proposed structure.

Step 6

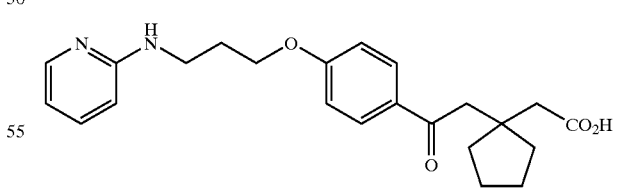

1-[2-oxo-2-[4-[3-(2-pyridinylamino)propoxy]phenyl]ethyl]cyclopentaneacetic Acid

A solution of the product from STEP 5 (115 mg) in methanol (5 mL) and 1N sodium hydroxide (5 ml) was stirred at room temperature for 18 hours. The reaction was quenched with TFA (2 mL) and concentrated. The residue was purified on a reverse phase HPLC using acetonitrile/water (0.5% TFA) gradient to give a white solid (110 mg).

$^1$H NMR (DMSO-d$_6$) δ1.60 (m, 8H); 2.08 (p, 2H); 2.48 (s, 2H); 3.20 (s, 2H); 3.49 (br. q, 2H); 4.18 (t, 2H); 6.84 (t, 1H); 7.03 (d, 3H); 7.86 (t, 2H); 7.95 (d, 3H); 8.70 (br. s, 1H); 11.96 (br. s, 1H); 13.5 (v. br. s, 1H). Anal. Calcd. for C$_{23}$H$_{28}$N$_2$O$_4$. 1.0 TFA: C, 58.85; H, 5.73; N, 5.49, Found: C, 58.41; H, 5.67; N, 5.55.

EXAMPLE 2

1-[2-[4-[3-(2-pyridinylamino)propoxy]phenyl]ethyl] cyclopentaneacetic Acid

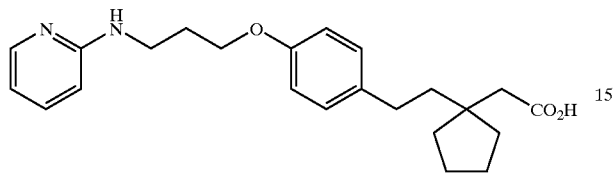

Step 1

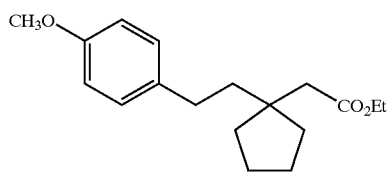

A solution of the product from STEP 2, EXAMPLE 1 (2.8 g) in ethanol containing several drops of phosphoric acid was shaken in a Parr hydrogenation apparatus with 20% Pd(OH)$_2$ on carbon under 60 psi hydrogen pressure at room temperature for 16 hours. The reaction mixture was then filtered and concentrated and the residue was purified on a silica gel column eluting with 15% ethyl acetate/hexane to afford a colorless liquid (1.5 g). The $^1$H NMR was consistent with the proposed structure.

Step 2

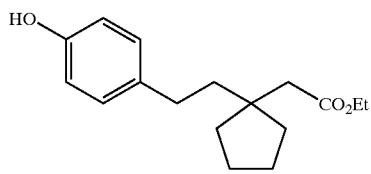

The above compound was prepared from the product described in STEP 1 (1.5 g) utilizing the same procedure as described in STEP 3, EXAMPLE 1. The crude product was purified on a silica gel column eluting with 30% ethyl acetate/hexane to afford a viscous oil (965 mg). The $^1$H NMR was consistent with the proposed structure.

Step 3

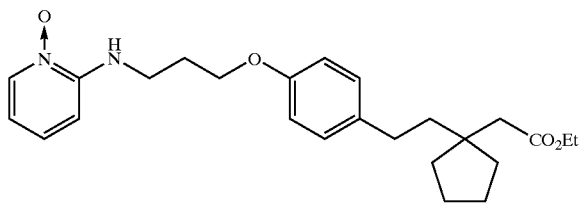

The above compound was prepared from the product prepared in STEP 2 (450 mg) using the same procedure as described in STEP 4, EXAMPLE 1. The crude product was purified on a silica gel column eluting with 97% CH$_2$Cl$_2$—2.5% CH$_3$OH—0.5% NH$_4$OH to afford a viscous oil (314 mg). The $^1$H NMR was consistent with the proposed structure.

Step 4

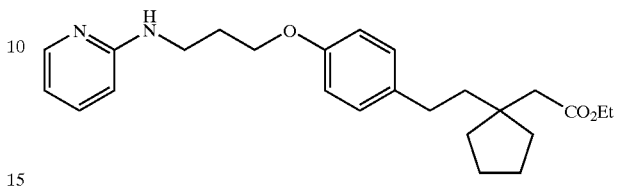

The above compound was prepared from the product of STEP 3 (305 mg) using the procedure described in STEP 5, EXAMPLE 1. The crude product was purified on a silica gel column eluting with 98% CH$_2$Cl$_2$—1.5% CH$_3$OH—0.5% NH$_4$OH to afford a viscous colorless oil (160 mg). The $^1$H NMR was consistent with the proposed structure.

Step 5

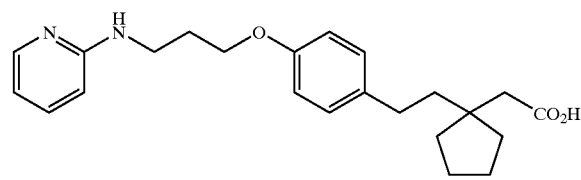

1-[2-[4-[3-(2-pyridinylamino)proppoxy]phenyl] ethyl]cyclopentaneacetic Acid

The above compound was prepared from the product from STEP 4 (150 mg) utilizing the same procedure as described in STEP 6, EXAMPLE 1. The crude product was purified in similar fashion to afford a viscous colorless oil (87 mg).). $^1$H NMR (DMSO-d$_6$) δ1.45 (m, 2H); 1.59 (m, 8H); 2.03 (p, 2H); 2.27 (s, 2H); 3.46 (q, 2H); 4.04 (t, 1H); 6.80 (t, 1H); 6.84 (d, 2H); 6.96 (d, 1H); 7.09 (d, 2H); 7.81 (t,1H); 7.92 (d, 1H); 8.45 (br. s, 1H); 12.02 (br. s, 1H). Anal. Calcd. for C$_{23}$H$_{30}$N$_2$O$_3$. 1.0 TFA: C, 60.48; H, 6.29; N, 5.64, Found: C, 61.21; H, 5.56; N, 5.84.

EXAMPLE 3

1-[2-oxo-2-[4-[2-(2-pyridinylamino)ethoxy]phenyl] ethyl]cyclopentaneacetic Acid

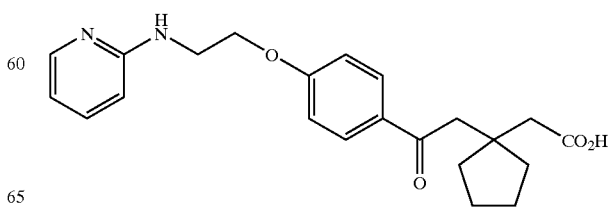

Step 1

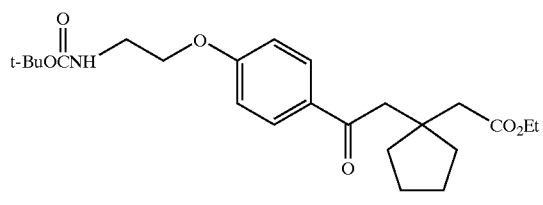

In a flame dried flask under nitrogen was prepared a solution of the product from STEP 3, EXAMPLE 1 (2.9 g), t-butyl N-(2-hydroxyethyl) carbamate (1.93 g), triphenylphosphine (3.15 g) and THF (45 mL) at room temperature. A solution of diethylazodicarboxylate (2.09 g) in THF (5 mL) was added dropwise and the reaction was allowed to stir at room temperature for 18 hours. The solvent was removed in vacuo and the crude product was purified on a silica gel column eluting with 25% ethyl acetate/hexane to afford a colorless viscous oil (3.40 g). The $^1$H NMR was consistent with the proposed structure.

Step 2

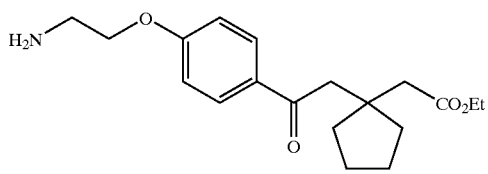

A solution of the product produced in STEP 1 (3.25 g), trifluoroacetic acid (15 mL) and methylene chloride (15 mL) was stirred at room temperature for 1 hour. The solvent was removed in vacuo and the resulting brown oil was partitioned between ethyl acetate and 10% sodium carbonate solution. The aqueous portion was extracted well with additional ethyl acetate and the combined organic extract was washed with water, brine and dried over $Na_2SO_4$. The solvent was removed to produce a viscous golden oil (2.68 g) which was used without further purification. The $^1$H NMR was consistent with the proposed structure.

Step 3

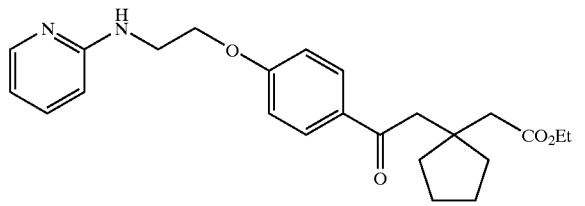

A mixture of the product prepared in STEP 2 (1.4 g), 2-fluoropyridine (458 mg) and DMF (10 mL) was heated at 110 degrees for 18 hours under nitrogen. The solvent was removed in vacuo and the residue was purified on a silca gel column eluting with 96.5% $CH_2Cl_2$—3.0% $CH_3OH$ and 0.5% $NH_4OH$ to afford a golden oil (145 mg). The $^1$H NMR was consistent with the proposed structure.

Step 4

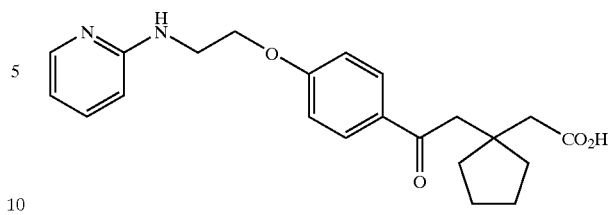

1-[2-oxo-2-[4-[2-(2-pyridinylamino)ethoxy]phenyl]ethyl]cyclopentaneacetic Acid

The above compound was prepared from the product prepared in STEP 3 (140 mg) using the procedure described in STEP 6, EXAMPLE 1. The crude product was purified in similar fashion to produce of a viscous colorless oil (50 mg). ). $^1$H NMR (CDCl$_3$) δ1.59 (m, 2H); 1.69 (m, 6H); 2.59 (s, 2H); 3.15 (s, 2H); 3.80 (br. q, 2H); 4.30 (t, 2H); 6.78 (t, 1H); 6.91 (d, 2H); 6.91 (d, 2H); 7.06 (d, 1H); 7.81 (br.d, 1H); 7.88 (ddd, 1H); 7.96 (d, 2H); 10.15 (br. s, 1H). Anal. Calcd for $C_{22}H_{26}N_2O_4 \cdot 1.75$ TFA: C, 52.63; H, 4.81; N, 4.81, Found: C, 52.33; H, 4.71; N, 4.70.

EXAMPLE 4

4-{4-[2-(6-aminopyridin-2-yl)ethoxy]phenyl}-3,3-dimethylbutanoic Acid

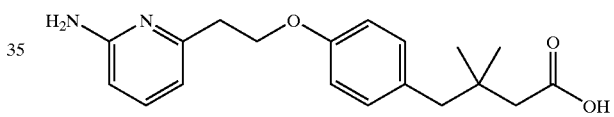

Step 1

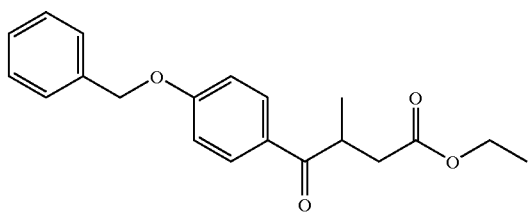

Ethyl 4-[4-(benzyloxy)phenyl]-3-methyl-4-oxobutanoate

To a stirred solution of lithium diisopropylamide (Aldrich, 100 mL, 2M solution in THF) in THF (950 mL) at −78° C. was added a suspension of 4-benzyloxypropiophenone (Lancaster, 50 g) in THF (75 mL) over one minute. After 45 minutes, ethyl bromoacetate (Aldrich, 23 mL) was added during one minute. After one hour, the mixture was allowed to warm to 0° C. over 3 hours. The reaction was quenched with saturated NH$_4$Cl (500 mL). The organic phase was separated and concentrated in vacuo. The residue was purified by chromatography over silica gel using 10% ethyl acetate in hexane as eluant to provide the above compound as a colorless liquid.

Step 2

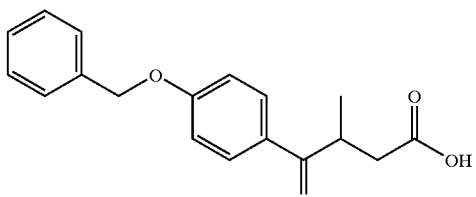

4-[4-(benzyloxy)phenyl]-3-methyl-4-oxobutanoic Acid

A mixture of the product of STEP 1 (45 g), ethanol (15 mL) and 15% aqueous NaOH (70 mL) was stirred at 23° C. for 30 minutes. The volatiles were removed in vacuo and the residue was acidified to pH=3. The precipitated solid was filtered and dried to give the above product as a white solid (40 g).

Step 3

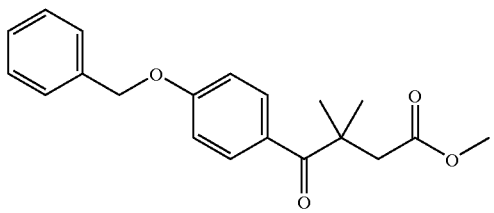

Methyl 4-[4-(benzyloxy)phenyl]-3,3-dimethyl-4-oxobutanoate

The product of STEP 2 (40 g) was added over 5 minutes, in portions to a stirred suspension of KH (Aldrich, 35 g of an oil suspension 35% (w/w)) in THF (750 mL) at 0° C. The mixture was cooled to −40° C. and DMSO (19 mL) was added over 2 minutes. The mixture was allowed to warm to 0° C. over ten minutes. Then the thick reaction mixture was cooled to −40° C. and iodomethane (Aldrich, 19 g) was added. After the addition was complete the reaction mixture became easy to stir. The mixture was allowed to warm to 0° C. and stirred for an additional 30 minutes. The reaction mixture was quenched with concentrated hydrochloric acid (50 mL). The mixture was extracted with ether and water. The organic phase was dried and concentrated. An ether solution of the residue was treated with excess diazomethane in ether 0° C. The resulting solution was concentrated in vacuo and the residue was purified by chromatography over silica gel using 10% ethyl acetate in hexane as eluant to provide the above compound as a colorless thick liquid.

Step 4

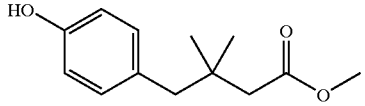

Methyl 4-(4-hydroxyphenyl)-3,3-dimethylbutanoate

A solution of the product of STEP 3 in methanol and phosphoric acid (catalytic amount) was shaken in Parr hydrogenation apparatus with 20% Pd(OH)$_2$/C under 60 psi hydrogen pressure for 9 hours. The solution was filtered and filtrate concentrated in vacuo. An ether solution of the residue was treated with excess diazomethane in ether at 0° C. The resulting solution was concentrated in vacuo and the residue was purified by chromatography over silica gel using 10% ethyl acetate in hexane as eluant to provide the above compound as a colorless thick liquid.

Step 5

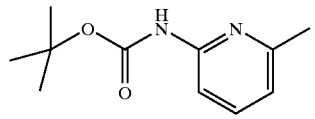

tert-butyl 6-methylpyridin-2-ylcarbamate

A solution of di-tert-butyl dicarbonate (32 g, Aldrich), 2-amino-6-picoline (15 g, Aldrich) and ether (20 mL) was allowed to stand at ambient temperature for 4 days. The volatiles were removed. The residue was purified by chromatography to give the above product as a white solid.

Step 6

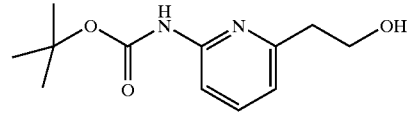

tert-butyl 6-(2-hydroxyethyl)pyridin-2-ylcarbamate

[6-(2-hydroxyethyl)-2-pyridinyl]carbamic acid, 1,1-dimethylethyl ester To stirred solution of the product of STEP 5 (11.9 g) in THF (100 mL) at −78° C. was added lithium diisopropylamide (85 mL, 1.5 M solution in THF, Aldrich) over 5 minutes. The cooling bath was removed after 1.5 hours. The reaction mixture was cooled back to −78° C. and DMF (4.5 mL) was added. After 15 minutes methanol (50 mL) was added followed by acetic acid (3.5 mL). Then sodium borohydride (2 g, Aldrich) was added and the reaction mixture was allowed to warm to ambient temperature. The mixture was carefully quenched with saturated aqueous ammonium chloride solution. The mixture was extracted with ethyl acetate. The layers were separated. The organic phase washed with water and concentrated in vacuo. The residue was purified by chromatography over silica gel using 20% ethyl acetate in hexane to remove starting material. Subsequent elution of the column with 60% ethyl acetate provided the above product as a white solid.

Step 7

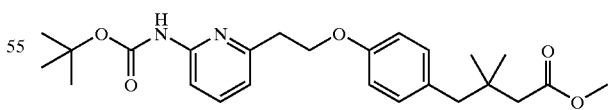

Methyl 4-[4-(2-{6-[(tert-butoxycarbonyl)amino] pyridin-2-yl}ethoxy)phenyl]-3,3-dimethylbutanoate To a stirred solution of the product of STEP 4 (0.45 g), the product of STEP 6 (0.723 g), triphenyl phosphine (0.80 g, Aldrich) in THF (10 mL) at −78° C. was added diisopropyl azodicarboxylate (Aldrich, 0.63 mL) over 3 minutes. The mixture was stirred at −78° C. for 3 hours and at 22° C. for 16 hours. The mixture was concentrated in vacuo and the residue was chromatographed over silica gel using 20% ethyl acetate in hexane as eluant. The fractions containing the desired product were pooled and concentrated to provide the above product as a thick gum.

Step 8

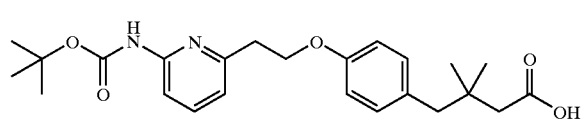

4-[4-(2-{6-[(tert-butoxycarbonyl)amino]pyridin-2-yl}ethoxy)phenyl]-3,3-dimethylbutanoic Acid A mixture of the product of STEP 7 (0.5 g) in methanol (2 mL) and a solution of NaOH (1 g) in water (6 mL) was heated to reflux for 30 minutes. The mixture was cooled to 0° C., acidified to pH=4 and extracted with ethyl acetate. The extract was dried over $MgSO_4$ and concentrated in vacuo to provide the above product as a white solid.

Step 9

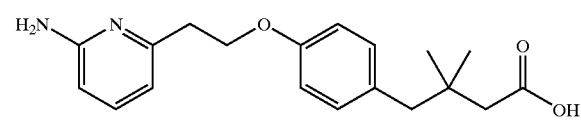

4-{4-[2-(6-aminopyridin-2-yl)ethoxy]phenyl}-3,3-dimethylbutanoic Acid

A solution of the product of STEP 8 in 4N hydrochloric acid was allowed to stir at 23° C. for 16 hours. The volatiles were removed in vacuo and the residue was washed with methanol and ether. The residue was dried in vacuo to provide the hydrochloride salt of the above product as a hygroscopic colorless solid. $^1H$ ($CD_3OD$) δ7.86 (1H, dd); 7.08 (2H, d); 6.86(3H, d); 4.31 (2H, t); 3.17 (2H, t); 2.53 (2H, s); 2.04 (2H, s); 0.91 (6H, s); Anal. Calcd for $C_{19}H_{24}N_2O_3 \cdot HCl \cdot 0.5 H_2O$: C, 61.04;H, 7.01; N, 7.49; Cl, 9.48; Found: C, 61.21; H, 7.18; N, 7.52; Cl, 9.44.

EXAMPLE 5

3,3-dimethyl-4-{4-[3-(pyridin-2-ylamino)propoxy]phenyl}butanoic Acid

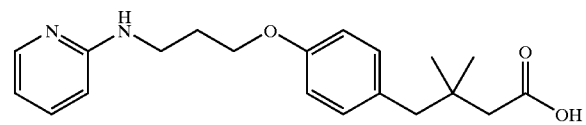

Step 1

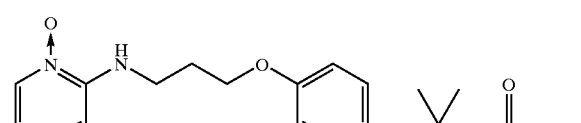

Methyl 3,3-dimethyl-4-{4-[3-(1-oxidopyridin-2-ylamino)propoxy]phenyl}-butanoate

The procedure for the preparation of the product of STEP 7, EXAMPLE 4 was repeated using 2-[3-hydroxy-1-propyl)amino]pyridine-N-oxide (Ref: WO 98/30542) in the place of the product of STEP 6, EXAMPLE 4 to provide the above product as a colorless gum.

Step 2

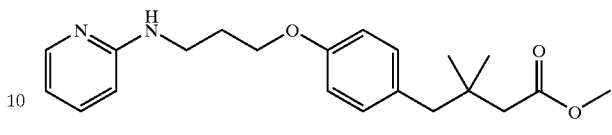

Methyl 3,3-dimethyl-4-{4-[3-(pyridin-2-ylamino) propoxy]phenyl}butanoate

A mixture of the product of STEP 1 (0.95 g), cyclohexene (Aldrich, 7 mL), 10% Pd/C (0.2 g) and isopropanol (10 mL) was heated to reflux for 20 hours. The mixture was filtered through celite and concentrated in vacuo. The residue was purified by chromatography using ethyl acetate as eluant to provide the above product as a thick gum.

Step 3

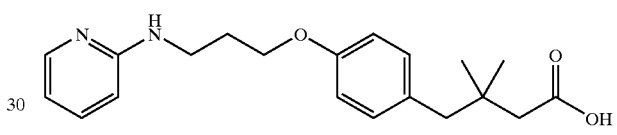

3,3-dimethyl-4-{4-[3-(pyridin-2-ylamino)propoxy] phenyl}butanoic Acid

A mixture of the product of STEP 2 (0.25 g) in methanol (2 mL) and a solution of NaOH (0.7 g) in water (4.5 mL) was heated to reflux for 30 minutes. The volatiles were removed and the residue was stirred with 1N hydrochloric acid (5 mL) for 5 minutes. The mixture was concentrated in vacuo. The residue was stirred with acetonitrile (5 mL) for 5 minutes. The precipitated colorless solid was collected by filtration and dried in vacuo provide the hydrochloride salt of the above product. $^1H$ DMSO) δ7.87 (1H, dd);7.80 (1H, d);7.09 (3H, d);6.86 (1H, t);6.84 (2H, d);4.12 (2H, t);3.61 (2H, t);2.60 (2H, s);2.18 (H, p);2.12 (2H, s);0.98 (6H, s). Anal. Calcd for $C_{20}H_{26}N_2O_3 \cdot HCl \cdot 0.25 H_2O$: C, 62.65; H, 7.23; N, 7.31; Cl, 9.25; Found: C, 62.89; H, 7.13; N, 7.36; Cl, 9.31.

EXAMPLE 6

1-[[4-[3-(2-pyridinylaminopropoxy]phenyl]methyl] cyclopropaneacetic Acid

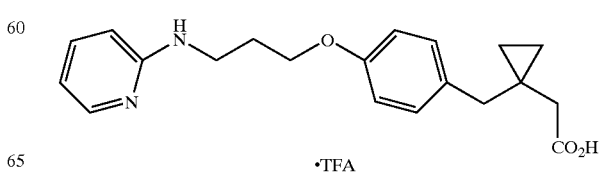

Step 1

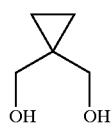

Dimethyl-1,1-cyclopropane dicarboxylate (18.4 g; 116.3 mmol) was dissolved in anhydrous diethyl ether (100 ml) and set aside. A 2L three-necked flask equipped with an inert atmosphere, magnetic stir bar and dropping funnel was charged with 2×100 mL of a 0.5 M solution of lithium aluminum hydride in glycoldimethyl ether and 1×100 mL of a 0.5M solution of lithium aluminum hydride in THF. The resulting solution was diluted further with anhydrous diethylether (200 mL). The solution of the diester was added dropwise via the addition funnel at 0° C. After the addition, the reaction was heated to reflux overnight. The following day the reaction mixture was carefully quenched with a saturated solution of sodium sulfate until all bubbling ceased. The solution was filtered through a coarse fritted funnel, dried (MgSO$_4$), filtered and concentrated to give a colorless oil. The precipitate, containing adhered product, was extracted with THF continuously in a soxhlet extractor. The THF was removed and the product was combined with the original batch to give the desired product (10 g;84% yield). $^1$H NMR was consistent with the structure of the desired product.

Step 2

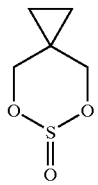

The diol (4.38 g; 42.9 mmoles) from the previous step was dissolved in pyridine (42.9 mL). To this solution was added, in a dropwise fashion, thionyl chloride (6.2 mL). After the addition the solution was stirred at 25° C. for 1 hour and the reaction mixture was filtered through a coarse fritted funnel. The precipitate was washed with fresh pyridine and the filtrates were concentrated to dryness. The resulting residue was diluted with anhydrous ether (450 mL) which caused a solid precipitate to form. The solution was decanted away from the solid and then washed with 6N aqueous HCl solution and a saturated solution of sodium bicarbonate. The ethereal extracts were dried (MgSO$_4$), filtered then concentrated to dryness to afford a white crystalline solid (4 g, 70% yield). The structural data was identical to that reported in the literature. $^1$H NMR was consistent with the structure of the desired product.

Step 3

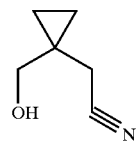

The starting cyclic sulfite (4.9625 g; 37.5 mmoles) produced in STEP 2 was dissolved in dry DMF (37 mL). To this solution was added sodium cyanide (2.01 g; 41.2 mmoles) and sodium iodide (1.12 g; 7.5 mmoles). The solution was heated to 70° C. After four days, the reaction mixture was diluted with toluene (59 mL) and then water (0.89 mL) was added slowly. The resulting yellow precipitate was filtered and washed with fresh toluene. The filtrates were transferred to a separatory funnel and diluted with ethyl acetate (500 mL) and washed with water (1×500 mL; 3×100 mL). The combined aqueous extracts were extracted with ethyl acetate (3×100 mL). The organic extracts were washed with brine and dried (MgSO$_4$), filtered and concentrated to give an oil which was purified by column chromatography (SiO$_2$ ethyl acetate/ hexane) to give the desired product (1.7 g; 41% yield). $^1$H NMR was consistent with the structure of the desired product.

Step 4

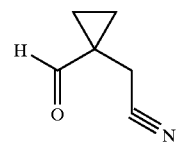

A flask equipped with an inert atmosphere was charged with methylene chloride (13 mL). To this solution was added a 2.0 M solution of oxalyl chloride in methylene chloride (11.3 mL) and a 2.0 M solution of oxallyl chloride in methylene chloride (11.3 mL). The solution was cooled to −60° C. then a solution of 3.4 mL of dimethylsulfoxide (3.84 g; 49.20 mmoles) in methylene chloride (8 mL) was added dropwise. After 10 minutes, a solution of the cyano-alcohol (2.28 g; 20.5 mmoles) from step 3 was added as a solution in methylene chloride (4 mL) and the solution was stirred at −60° C. After 15 minutes, triethylamine (2.8 mL) was added and then the reaction was allowed to warm to 25° C. The work-up consisted of filtering off the triethylamine hydrochloride then concentrating the filtrate to dryness. The crude residue was taken up in anhydrous ether and the solution was carefully pipetted away from the hydrochloride salt. The solution was concentrated and the crude residue was purified by column chromatography (35% ethyl acetate/ hexane) to give the desired aldehyde (1.68 g ; 75% yield). The $^1$H NMR spectrum was consistent with the structure of the desired product.

Step 5

The aldehyde from STEP 4 was dissolved in anhydrous ether (50 mL). To this solution was added 30.8 mL of a 0.5 M solution of 4-methoxyphenyl-magnesium bromide in tetrahydrofuran in a dropwise fashion over 1 hour at −30° C. After 1 hour, the reaction mixture was poured into a cold sulfuric acid solution (prepared by pouring 30 mL of concentrated sulfuric acid onto 250 g of crushed ice then adding 250 mL of water). The aqueous solution was extracted with ether. The ether extracts were washed with a saturated solution of sodium bicarbonate followed by brine and the organic extracts were dried (MgSO$_4$). The solution was filtered then evaporated to dryness to provide a yellow oil (4.1 g) which contained traces of THF and ether. The oil was calculated to contain 3.09 g of the desired product (92%).

The product was used in the next step without further purification. ¹H NMR was consistent with the structure of the desired product.

Step 6

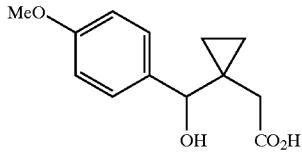

The hydroxynitrile (3.0 g; 13.8 mmole) prepared in STEP 5 was suspended in 10 ml of a 1.68 M aqueous potassium hydroxide solution. The reaction was heated overnight to 80° C. The temperature was raised to 100° C. The traces of organic solvent left in the product from the previous step prevented the reaction to reach the required temperature so it was removed under reduced pressure. The resulting solution was heated overnight to 80° C. and by tlc, the following day, the reaction went to completion. The reaction was worked up by extracting it with ether. The aqueous layer was acidified to pH 6 then extracted with ethyl acetate then methylene chloride. The tlc was taken on the extracted aqueous layer and it was noted that UV activity was present. The pH was carefully adjusted by adding increments of acid followed by extracting with ethyl acetate and then rechecking the water layer for UV activity. This process was repeated until UV activity was absent from the water layer. The organic extracts were dried (MgSO₄), filtered then evaporated under reduce pressure to give the crude product (2.6 g). This material was used in the next step without further purification. ¹H NMR was consistent with the structure of the desired product.

Step 7

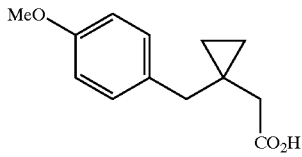

The hydroxy acid (1.41 g; 5.96 mmoles) produced in STEP 6 was dissolved in methylene chloride (22 mL) followed by the addition of 0.91 ml of triethylsilane (832 mg; 7.15 mmoles) and trifluoracetic acid (1.14 mL) at 25° C. After stirring for 12 hours, an aliquot was removed, the solvent was evaporated under reduced pressure. ¹H NMR indicated that the reaction went to 25% completion. The crude mixture was re-subjected to the reaction conditions. After 12 hours, the solvent was removed under reduced pressure. The crude material (1.4 g; >100% yield) was clean enough to take on to the next step without purification. ¹H NMR was consistent with the structure of the desired product.

Step 8

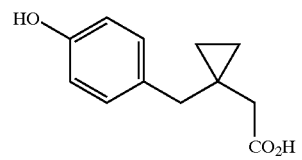

The carboxylic acid (706 mg; 3.26 mmoles) obtained from the previous step was dissolved in anhydrous methylene chloride (3.5 mL) and cooled to 0° C. To this solution was added a 1M solution of boron tribromide in methylene chloride (7.35 mL) all at once. The solution turned a red-brown color. After 30–40 minutes at 0° C., water (9 mL) was added along with additional methylene chloride until the layers cleanly separated. The aqueous layer was extracted once with methylene chloride and several times with ethyl acetate. The methylene chloride solution was extracted with a saturated solution of sodium bicarbonate and then the aqueous extracts were washed with methylene chloride. The pH was then adjusted to 3 with 6N HCl then extracted several times with ethyl acetate. The combined ethyl acetate extracts were washed two times with water then washed with brine. The organic extracts were dried (MgSO₄), filtered and evaporated to dryness to give the desired compound as a brown oil (443 mg; 67% yield). The product was taken to the next step without further purification. ¹H NMR was consistent with the structure of the desired product.

Step 9

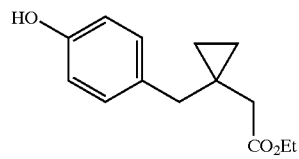

The crude acid (586 mg; 2.90 mmoles) isolated from the previous step was dissolved in absolute ethanol (5 mL) and 4N HCl in dioxane (5 mL) at 25° C. After stirring for 12 hours, the reaction mixture was evaporated to dryness under reduced pressure. The crude oil was redissolved in ethylacetate and washed with a saturated solution of aqueous sodium bicarbonate then washed with brine. The organic extracts were dried (MgSO₄), filtered and evaporated under reduced pressure to give a brown oil (609 mg). The oil was dissolved in anhydrous ether, which caused the brown color to precipitate out of solution. The precipitate was filtered away which resulted in a yellow oil (550 mg; 82% yield), which was taken to the next step without further purification. The ¹H NMR spectrum was consistent with the structure of the desired product.

Step 10

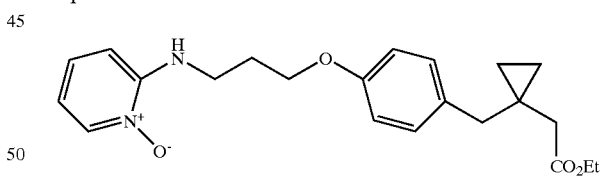

The crude phenol (246.6 mg; 1.07 mmoles) from STEP 9 and triphenylphosphine (430 mg; 1.64 mmoles) were stirred together at 0° C. under nitrogen in THF (3.8 ml). To this solution was added DEAD (0.23 mL) which was stirred at 0° C. After 15 minutes, 2-(3-hydroxypropylamino)pyridine N-oxide (410.5 mg; 1.53 mmoles) was added as a powder all at once. The reaction mixture was placed in a hot water bath (50° C.) for 15 minutes and the reaction was allowed to cool to 25° C. and stirrred overnight. The reaction mixture was concentrated under reduced pressure and then purified by flash chromatography (SiO₂; 100% ethyl acetate then 92 CH₂Cl₂/8IPA 0.5% acetic acid) to give a yellow oil (239 mg; 50% yield). This material was converted to the free base by dissolving the yellow oil in absolute ethanol (1 ml) and then adding concentrated ammonium hydroxide (0.33 mL). This was followed by concentrating down the solution under reduced pressure then subjecting the resulting residue to high vacuum for 1 hour to give a pink oil (203 mg). The ¹H NMR spectrum was consistent with the structure of the desired product.

Step 11

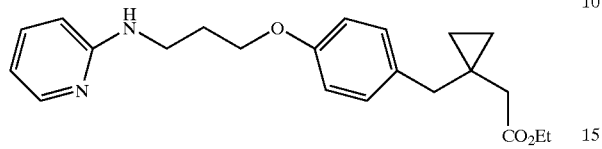

The pyridyl ester (200 mg; 0.52 mmoles) from STEP 10 was dissolved in isopropyl alcohol (4.4 ml) to give a pink solution. To this solution was added 10% palladium on carbon (46 mg) followed by cyclohexene (0.44 mL). The reaction was heated to reflux. After 2 hours, no product was observed by TLC. Additional catalyst (46 mg) and cyclohexene (0.44 ml) were added. The TLC was checked after 1 hour which indicated the reaction went to completion. The reaction was filtered through celite, then concentrating the filtrates under reduced pressure gave a colorless oil (222 mg). This material was taken to the next step without further purification. ¹H NMR was consistent with the structure of the desired product.

Step 12

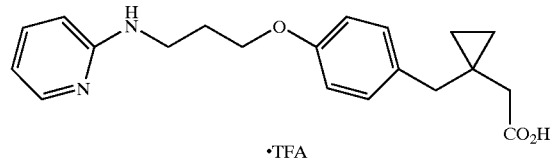

1-[[4-[3-(2-pyridinylaminopropoxy]phenyl]methyl] cyclopropaneacetic Acid

The ester (222 mg; 0.52 mmoles) produced in STEP 11 was dissolved in methanol (7.2 ml). To this solution was added 1N sodium hydroxide (7.2 ml). This solution was stirred overnight at 25° C. and then quenched with TFA (ca. 0.55 mL) until pH 3 was obtained. The solvent was removed under reduced pressure to give the crude residue which was purified by HPLC (gradient elution 90/10 H$_2$O/CH$_3$CN to 50/50 H$_2$O/CH$_3$CN) to give the desired compound as a colorless oil (198 mg). NMR (CDCl$_3$) δ0.49 (m, 2H); 0.54(m, 2H); 2.13 (s, 2H); 2.15 (pentet, 2H); 2.64 (s, 2H); 3.53 (t, 2H); 4.06 (t, 2H); 6.76 (t, 1H); 6.82(d, 2H); 6.92 (d, 1H); 7.12 (d, 2H) 7.76–7.84 (2H) Anal. Calcd. for C$_{20}$ H$_{24}$ N$_2$O$_3$.1.5 CF$_3$CO$_2$H: C, 54.01; H, 5.03; N, 5.48; Found: C, 54.38; H, 5.10; N, 5.94.

EXAMPLE 7

[[[4-[3-(2-pyridinylamino)propoxy]phenyl]methyl] sulfonyl]acetic Acid

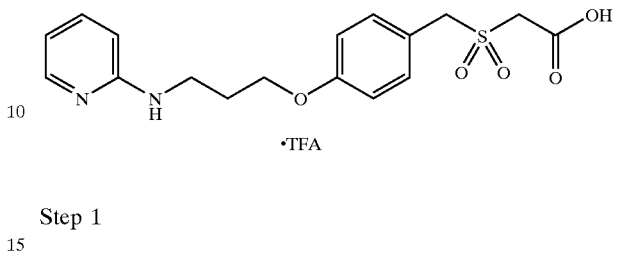

Step 1

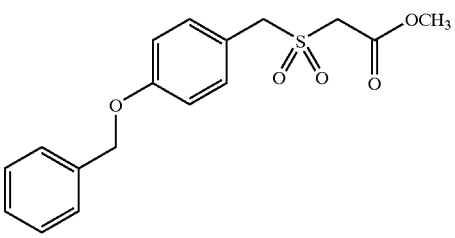

To a three-necked flask equipped with bubbler, nitrogen atmosphere and stir bar was added methanol (100 ml) and methyl thioglycolate (5.30 g; 50 mmoles) followed by sodium methoxide (2.70 g; 50 mmoles). After stirring at 25° C. for 15 minutes, the solution was clear and then 4-benzyloxybenzyl chloride (16 g; 75 mmoles) was added all at once and the reaction was heated to 80° C. After 12 hours, the reaction was cooled then filtered. The filtrates were concentrated under reduced pressure to give an oil which was redissolved in methanol (200 ml). An aqueous solution of Oxone (61.4 g dissolved in 247 ml of water) was prepared and then added to the methanolic solution of the crude sulfide. After stirring at 25° C. for 12 hours, the solution was concentrated under reduced pressure then partitioned between additional water and CH$_2$Cl$_2$. The aqueous extracts were were extracted three times with CH$_2$Cl$_2$. The organic extracts were dried (MgSO$_4$) filtered and stripped to provide a colorless oil which solidified upon standing. The crude material was purified by column chromatography (SiO$_2$, 10/90 ethyl acetate-toluene) to give the desired material (5.0 g). The ¹H NMR spectrum was consistent with the structure of the desired product.

Step 2

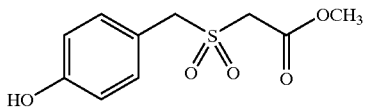

The compound (5 g; 16 mmol) isolated from STEP 1 was dissolved in MeOH (50 mL). THF (10 mL) was added to help solubilize the compound, which was followed by the addition of 20% palladium hydroxide on carbon (1 g). The reaction mixture was charged into 250 mL hydrogenation bottle and shaken in a Parr hydrogenation apparatus at 25° C. for 1 hour. The catalyst was removed by filtration and washed with methanol (2×20 mL). The washes and filtrate were combined and concentrated under reduced pressure to give the desired product (3.01 g; 75% yield).

Step 3

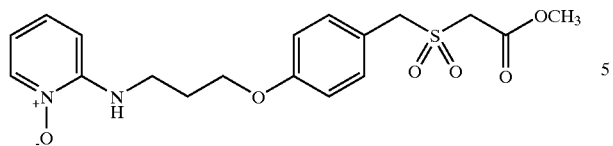

The phenol (256 mg; 1.05 mmoles) from STEP 2 and triphenylphosphine (430 mg; 1.64 mmoles) were dissolved in anhydrous THF (3.8 mL) and cooled to 0° C. under an atmosphere of nitrogen. To this solution was added DEAD (263.3 mg; 1.51 mmoles). After 15 minutes, the aminopyridine alcohol (410.5 mg;1.53 mmoles) was added as a powder all at once. The reaction mixture was placed in a hot water bath (50° C.) for 15 minutes and the reaction was allowed to cool to 25° C. and stirred overnight. The reaction mixture was concentrated under reduced pressure and then purified by flash chromatography (SiO$_2$; 100% ethyl acetate then 92 CH$_2$Cl$_2$/8IPA 0.5% acetic acid) to give a yellow oil (239 mg; 50%). This material was converted to the free base by dissolving the yellow oil in absolute ethanol (1 ml) and then adding concentrated ammonium hydroxide (0.33 mL). The mixture was concentrated under reduced pressure and the resulting residue was subjected to high vacuum for 1 hour to give the desired compound (189 mg; 44% yield). The $^1$H NMR spectrum was consistent with the structure of the desired product.

Step 4

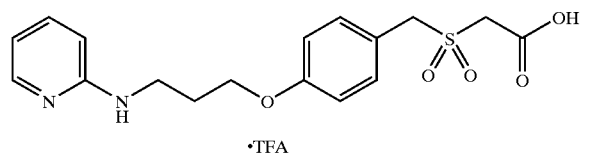

·TFA

[[[4-[3-(2-pyridinylamino)propoxy]phenyl]methyl] sulfonyl]Acetic Acid

The desired pyridine-N-oxide (189 mg; 0.465 mmoles) isolated from STEP 3 was dissolved in isopropanol (4.4 mL). To this solution was added 10% palladium on carbon (46 mg) followed by cyclohexene (0.44 mL). After 2 hours, the TLC showed no reaction. Equivalent quantities of catalyst and cyclohexene were added. Some THF was added to enhance solubility of the starting material. The following day tlc indicated both product and starting material were present. The catalyst and cyclohexene (quantities used are stated above) were added. By 6 hours, the reaction was complete. The reaction mixture was filtered through celite and the filtrates were concentrated under reduced pressure. The resulting crude residue was dissolved in aqueous 1N sodium hydroxide (7 ml) and methanol (7 ml) and stirred at 25° C. After 12 hours, the reaction was quenched with TFA and concentrated under reduced pressure. The resulting residue was purified by reverse phase HPLC (90/10 H$_2$O/CH$_3$CN—50/50 H$_2$O/CH$_3$CN gradient elution) to give a white solid (173 mg). $^1$H NMR (DMSO-d$_6$) δ2.06 (pentet, 2H); 3.48 (t, 2H); 4.10 (t, 2H); 4.13 (s, 2H); 4.55 (s, 2H); 6.81 (t, 1H); 6.94–7.03 (3H), 7.31 (d, 2H); 7.83 (t, 1H); 7.92 (d, 1H); Anal. Calcd. for C$_{17}$H$_{20}$O$_5$N$_2$S1.1CF$_3$CO$_2$H. C, 47.18; H, 4.14; N, 5.73; S, 6.56. Found: C, 47.05; H, 4.20; N, 5.72; S, 6.63.

EXAMPLE 8

1-[[4-[3-(2-pyridinylamino)propoxy]phenyl]methyl] cyclobutaneacetic Acid

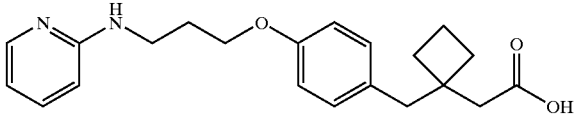

Step 1

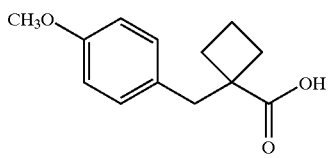

A solution of cyclobutanecarboxylic acid (10 g, 100 mmoles) in THF (100 ml) was added dropwise to a solution of lithium diisopropylamide (110 ml, 220 mmoles, 2M in heptane/THF/ethylbenzene) diluted with THF (120 ml) at −20° C. under argon. The resulting mixture was stirred at 0° C. for 15 minutes, then warmed to 30–35° C. and stirred for 1 hour. The mixture was cooled back to −20° C., and treated with a solution of 4-methoxybenzyl chloride (20 g, 130 mmoles) in THF (100 ml) dropwise. The reaction was stirred at −10° C. for 1 hour, and then gradually warmed to 30–35° C. After 1 hour, the reaction mixture was quenched with a saturated NH$_4$Cl solution (120 ml). The solvents were partially removed under reduced pressure. A 5% aqueous NaOH solution was added to adjust the pH to 12. The mixture was washed with ether (3×150 ml). The aqueous layer was acidified with concentrated HCl, and thoroughly extracted with CH$_2$Cl$_2$ (3×150 ml). The combined CH$_2$Cl$_2$ layers were dried with Na$_2$SO$_4$, and concentrated to give the crude product mixture (12.1 g). The $^1$H-NMR spectrum was consistent with the proposed structure.

Step 2

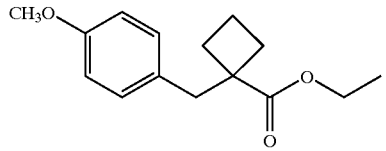

A solution of the product from STEP 1 (12.1 g), HCl in 1,4-dioxane (50 ml, 4.0 M) and ethanol (100 ml) was stirred at room temperature for 48 hours. The solvents were removed under reduced pressure. The residue was diluted with ethyl acetate (300 ml), and washed with saturated NaHCO$_3$ solution (100 ml). The organic extracts were dried with MgSO$_4$ and concentrated to give a pale brown oil (8.7 g). The combined yield of STEP 1 and STEP 2 was 35%. The $^1$H-NMR spectrum was consistent with the proposed structure.

Step 3

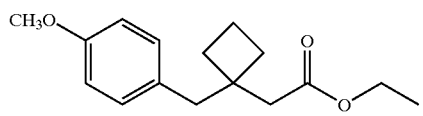

Under an atmosphere of argon, 2,2,6,6-tetramethyl piperidine (6.85 g, 48.4 mmoles) was added to a solution of n-butyl lithium (18.0 ml. 44.4 mmoles, 2.5M in hexane) diluted with THF (50 ml) at 0° C. to form LTMP. In a separate flask, a solution of the product from STEP 2 (5.0 g, 20.2 mmoles), dibromomethane (7.7 g, 44.4 mmoles), and THF (50 ml) was cooled to −78° C. After 30 minutes, LTMP solution was added to above solution via a double-ended needle over 20 minutes. After 10 minutes, a lithium bis (trimethylsilyl)amide solution (40.3 ml, 40.3 mmoles, 1 M in THF) was added to the reaction over 15 minutes at −78° C. The reaction was warmed to −20° C. and then cooled to −78° C. A solution of s-butyl lithium (62 ml, 80.6 mmoles, 1.3M in cyclohexane) was added at −60° C. over 20 minutes. The reaction was warmed to −20° C. A solution of n-butyl lithium (16.1 ml, 40.3 mmoles, 2.5M in hexane) was added. The reaction was allowed to warm to room temperature, and stirred for 1 hour. The reaction was cooled to −78° C. and quenched into a stirred anhydrous acidic ethanol solution at 0° C. over 40 minutes. The resulting mixture was diluted with ether (800 ml), and washed with 1N HCl solution (350 ml). The aqueous layer was extracted with ether (3×80 ml). The combined ethereal extracts were dried with MgSO$_4$, filtered and concentrated. Chromatography of the residue (SiO$_2$; ethyl acetate/hexane=8/92) gave the desired product as a pale brown oil (1.6 g; 30% yield). The $^1$H NMR spectrum was consistent with the proposed structure.

Step 4

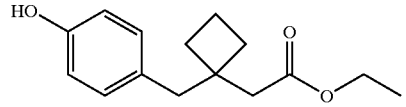

A solution of boron tribromide (5.1 ml, 5.1 mmoles, 1 M in CH$_2$Cl$_2$) was added to a solution of the product from STEP 3 (1.0 g, 3.8 mmoles) in CH$_2$Cl$_2$ (12 ml) at 0° C. over 10 minutes. The cold bath was removed. After 1.5 hours, ethanol (20 ml) was added to the reaction at 0° C. The resulting solution was stirred at room temperature for 40 minutes, diluted with ethyl acetate and washed with saturated NaHCO$_3$ solution (50 ml). The aqueous layer was extracted with ethyl acetate. The combined organic extracts were dried with MgSO$_4$, and concentrated to give a crude product mixture. Chromatography of the crude residue (on silica gel, hexane/ethyl acetate 88/12) gave the desired product as a pale brown oil (0.36 g; 38% yield). The $^1$H NMR spectrum was consistent with the proposed structure.

Step 5

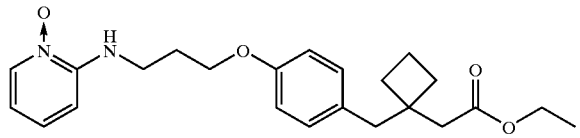

Triphenyl phosphine (0.51 g, 1.97 mmoles) was added to a solution of the product from STEP 4 (0.35 g, 1.41 mmoles) in THF (20 ml) at 0° C. Diethyl azodicarboxylate (0.31 ml, 1.97 mmoles) was added to above solution at 0° C. under Argon. The resulting solution was stirred at 0° C. for 20 minutes. 2-(3-hydroxypropylamino)pyridine N-oxide (0.26 g, 1.55 mmoles) was added to the reaction at 0° C. over 15 minutes. The reaction was allowed to warm to 25° C. and stirred for 18 hours. The solvent was removed from the reaction mixture under reduced pressure to give an oily residue. The residue was purified by chromatography (on silica gel, dichloromethane /2-propanol/acetic acid 92/8/0.5) to give the desired product as an oil (0.32 g; 51% yield). The $^1$H NMR spectrum was consistent with the proposed structure.

Step 6

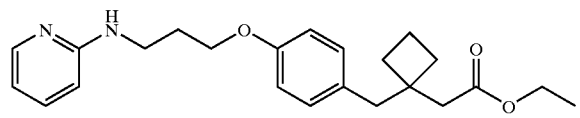

A mixture of the product from STEP 5 (0.28 g, 0.61 mmoles), 10% Pd/C (0.078 g, 0.073 mmoles), cyclohexene (0.74 ml, 7.3 mmoles), and 2-propanol (15 ml) was heated to reflux. After 18 hours, the reaction was allowed to cooled to room temperature. An additional 10% Pd/C (0.078 g, 0.073 mmoles) and cyclohexene (0.74 ml, 7.3 mmoles) was added. After 5 hours of reflux, the reaction was cooled to room temperature, filtered through a short column of Celite®, and washed with 2-propanol (25 ml). The filtrate was concentrated to give a clean product as an oil (0.27 g; 100% yield). The $^1$H NMR spectrum was consistent with the proposed structure.

Step 7

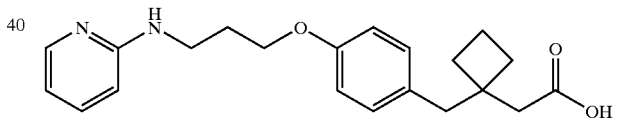

1-[[4-[3-(2-pyridinylamino)propoxy]phenyl]methyl] cyclobutaneacetic Acid

A solution of the product from STEP 6 (0.25 g, 0.65 mmoles), aqueous NaOH solution (12 ml, 2N), and ethanol (18 ml) were stirred at room temperature for 18 hours. Trifluoroacetic acid (2 ml) was added to the reaction. The solvents were removed from the reaction under reduced pressure to give a crude product. The crude residue was purified by reversed phase HPLC to give 1-[[4-[3-2 (pyridinylamino)propoxy]phenyl]methyl]cyclobutaneacetic acid as a gummy solid (0.26 g; 81% yield). $^1$H NMR (CDCl$_3$) δ1.88 (m, 4H); 2.01 (m, 2H); 2.18 (p, 2H); 2.40 (s, 2H); 2.84 (s, 2H); 3.52 (br. t, 2H); 4.06 (t, 2H); 6.68 (t,1H); 6.79 (d, 2H); 6.83 (d, 1H); 7.21 (d, 2H); 7.74 (m, 2H); 9.89 (br. s, 1H); Anal. Calcd for C$_{21}$H$_{26}$N$_2$O$_3$·1.1CF$_3$COOH·0.5H$_2$O: C, 57.00; H, 5.79; N, 5.73; found C, 57.37; H, 5.92; N, 5.21.

EXAMPLE 9

1-[[4-[3-(2-pyridinylamino)propoxy]phenyl]methyl]cyclopentaneacetic Acid

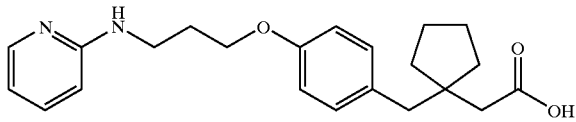

Step 1

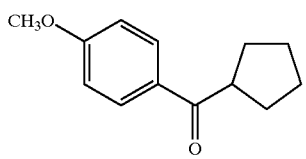

A solution of cyclopentylmagnesium bromide (56.3 ml, 113 mmoles, 2M in ether) was added to a solution of 4-methoxybenzonitrile (10.0 g, 75.1 mmoles) in THF (50 ml) dropwise at 0° C. The resulting reaction mixture was allowed to warm to room temperature. After 3 hours, the reaction mixture was cooled to 0° C., and quenched with an aqueous 10% HCl solution. The resulting mixture was stirred at room temperature for 30 minutes. An aqueous NaOH (6N) solution was added slowly to adjust the pH to 6. The product was extracted with ether (350 ml) and washed with brine (200 ml). The organic layer was dried with MgSO$_4$ and concentrated to give a crude residue. Chromatography of the crude residue (SiO$_2$; hexane/ethyl acetate 8/2) gave the desired product as a pale yellow oil (9.3 g; 61% yield). The $^1$H NMR spectrum was consistent with the proposed structure.

Step 2

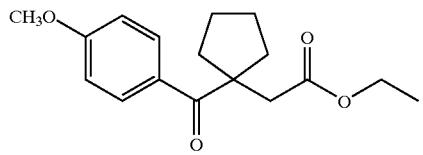

A solution of the product from STEP 1 (8.0 g, 39.3 mmoles) in THF (100 ml) was added to a solution of potassium bis(trimethylsilyl)amide (94.4 ml, 47.2 mmoles, 0.5M in toluene) diluted with THF (50 ml) at 25° C. under argon. The resulting solution was stirred at room temperature for 45 minutes. A solution of ethyl bromoacetate (4.45 g, 47.2 mmoles) in THF (100 ml) was added at 0° C. dropwise and then allowed to warm to room temperature. After 1.5 hours, the reaction was diluted with ethyl acetate (500 ml) and washed with water (300 ml). The organic layer was dried with MgSO$_4$, filtered and concentrated. Chromatography of the residue (on silica gel, toluene/ethyl acetate= 8/2) gave the desired product as an oil (2.7 g; 24% yield). The $^1$H NMR spectrum was consistent with the proposed structure.

Step 3

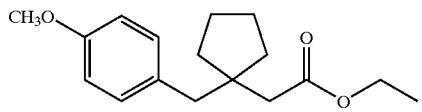

A mixture of product from STEP 2 (0.79 g, 2.72 mmoles) was dissolved in ethanol (30 ml), and followed by addition of 20% Palladium (II) hydroxide on carbon (0.40 g) and H$_3$PO$_4$ (4 drops). The reaction was purged with nitrogen and hydrogenated at 60 psi and at 25° C. for 20 hours. The catalyst was removed by filtration and washed with ethanol (2×20 ml). The filtrate was concentrated, diluted with ethyl acetate (150 ml), and washed with water. The organic layer was dried with MgSO$_4$ and concentrated. The residue (0.64 g) was dissolved in ethanol (15 ml) and a solution of 4M HCl in dioxane (15 ml). The resulting solution was stirred at 25° C. for 48 hours. The solvents were removed under reduced pressure to give a pale brown oil (0.64 g; 85% yield). The $^1$H NMR spectrum was consistent with the proposed structure.

Step 4

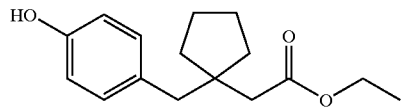

A boron tribromide solution (2.97 ml, 1M in CH$_2$Cl$_2$) was added dropwise to a solution of product from STEP 3 (0.62 g) in CH$_2$Cl$_2$ (8 ml) at 0° C. The cold bath was removed. After 20 minutes, ethanol (8 ml) was added to the reaction. The resulting mixture was stirred at room temperature for 30 minutes. The solvents were removed from the reaction under reduced pressure. The residue was diluted with ethyl acetate (100 ml), and washed with a saturated aqueous NaHCO$_3$ solution (50 ml). The aqueous layer was extracted with ethyl acetate (2×20 ml). The combined organic extracts were dried with Na$_2$SO$_4$, and concentrated to give a crude product mixture. Chromatography of the crude residue (SiO$_2$; hexane/ethyl acetate 8/2) gave the desired product as a pale brown oil (0.22 g; 38% yield). The $^1$H NMR spectrum was consistent with the proposed structure.

Step 5

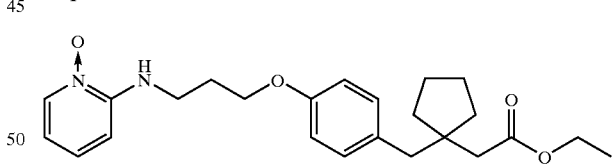

Triphenyl phosphine (0.393 g, 1.5 mmoles) was added to a solution of the product from STEP 4 (0.28 g, 1.07 mmoles) in THF (15 ml) at 0° C. Diethyl azodicarboxylate (0.24 ml, 1.5 mmoles) was added to above solution at 0° C. under argon. The resulting solution was stirred at 0° C. for 20 minutes. 2-(3-hydroxypropylamino)pyridine N-oxide (0.197 g, 1.17 mmoles) was added to the reaction over 15 minutes. The reaction was allowed to warm to room temperature and stirred for 18 hours. The solvent was removed from the reaction mixture under reduced pressure to give an oily residue. The crude residue was purified by chromatography (on silica gel, dichloromethane /2-propanol/acetic acid 93/7/ 0.5) to give the desired product as an oil (0.25 g; 57% yield). The $^1$H NMR spectrum was consistent with the proposed structure.

Step 6

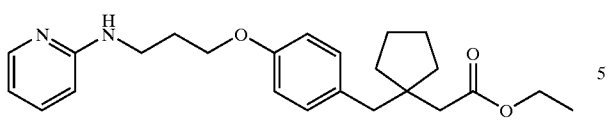

A mixture of the product from STEP 5 (0.25 g, 0.53 mmoles), 10% Pd/C (0.068 g, 0.064 mmoles), cyclohexene (0.64 ml, 6.4 mmoles), and 2-propanol (10 ml) was heated to reflux. After 18 hours, the reaction was allowed to cool to room temperature. An additional 10% Pd/C (0.068 g, 0.064 mmoles) and cyclohexene (0.64 ml, 6.4 mmoles) were added. After 6 hours of reflux, the reaction was cooled to room temperature and filtered through a short column of Celite®, and washed with 2-propanol (15 ml). The filtrate was concentrated to give a clean product as an oil (0.18 g; 75% yield). The $^1$H NMR spectrum was consistent with the proposed structure.

Step 7

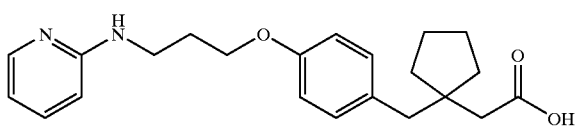

1-[[4-[3-(2-pyridinylamino)propoxy]phenyl]methyl]cyclopentaneacetic Acid

A solution comprised of the product of STEP 6 (0.18 g, 0.45 mmoles), aqueous 25° C. room temperature for 18 hours. Trifluoroacetic acid (2 ml) was added to the reaction. The solvents were removed from the reaction under reduced pressure to give a crude product. The crude product was purified by HPLC to give 1-[[4-[3-(2-pyridinylamino)propoxy]phenyl]methyl]cyclopentaneacetic acid as a clear oil (0.15 g; 79% yield). ). $^1$H NMR (CDCl$_3$) δ1.51 (m, 2H); 1.61 (m, 2H); 1.68 (m, 4H); 2.17 (p, 2H); 2.26 (s, 2H); 2.73 (s, 2H); 3.56 (q, 2H); 4.05 (t, 2H); 6.73 (t, 1H); 6.81 (d, 2H); 6.87 (d, 1H); 7.14 (d, 2H); 7.77 (dd, 1H); 7.85 (d, 1H); 9.22 (br. s, 1H); 11.34 (br.s, 1H). Anal. Calcd for C$_{22}$H$_{28}$N$_2$O$_3$.1.75 CF$_3$COOH.0.25 H$_2$O: C, 53.08; H, 5.37; N, 4.85; found C, 52.85; H, 5.29; N, 4.87.

EXAMPLE 10

[[[4-[2-[6-(methylamino)-2-pyridinyl]ethoxy]phenyl]methyl]sulfonyl]acetic Acid

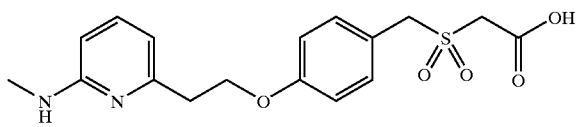

Step 1

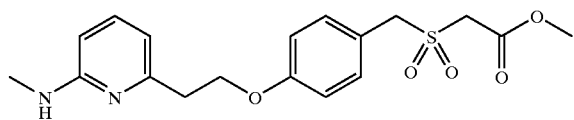

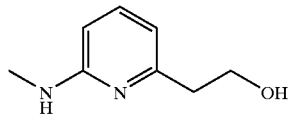

The phenol (300 mg; 1.23 mmoles) from STEP 2, EXAMPLE 7 and triphenylphosphine (494 mg; 1.88 mmoles) were dissolved in anhydrous THF (2 mL) and cooled to 0° C. under an atmosphere of nitrogen. To this solution was added DEAD (302.04 mg; 1.73 mmoles). After 15 minutes, the aminopyridine alcohol B (232 mg; 1.52 mmoles) was added as a solution in THF (2 ml) over 15 minutes. The reaction mixture was warmed to 25° C. After 12 hours, the reaction mixture was concentrated under reduced pressure and then purified by flash chromatography (SiO$_2$; 50% ethylacetate/hexane) to give a yellow oil. The $^1$H NMR spectrum was consistent with the structure of the desired product.

Step 2

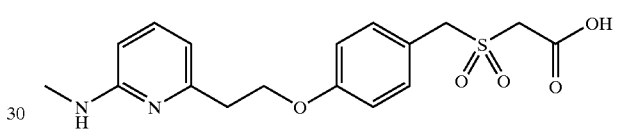

[[[4-[2-[6-(methylamino)-2-pyridinyl]ethoxy]phenyl]methyl]sulfonyl]acetic Acid

The compound obtained from STEP 1 was dissolved in aqueous 1N sodium hydroxide (7 ml) and methanol (7 mL) and stirred at 25° C. After 12 hours the reaction was quenched with TFA and concentrated under reduced pressure. The resulting residue was purified by reverse phase HPLC (90/10 H$_2$O/CH$_3$CN-50/50 H$_2$O/CH$_3$CN gradient elution) to give a white solid (173 mg). NMR (acetonitrile-d$_3$) δ2.84 (s, 3H); 3.1 (t, 2H); 3.94 (s, 2H); 4.21 (t, 2H); 4.41 (s, 2H); 6.65 (d, 1H); 6.72 (d, 1H); 6.85 (d, 2H), 7.25 (d, 2H 7.70 (t, 1H). Anal. Calcd for C$_{17}$H$_{20}$N$_2$O$_5$S plus 1.1 CF$_3$CO$_2$H: C, 47.08; H, 4.34; N, 5.72; S, 6.55. Found: C, 47.27; H, 4.57; N, 6.15; S, 6.28.

EXAMPLE 11

3,3-dimethyl-4-{4-[2-(5,6,7,8-tetrahydro-1,8-naphthyridin-2-yl)ethoxy]phenyl}butanoic Acid

CF$_3$COOH

Step 1

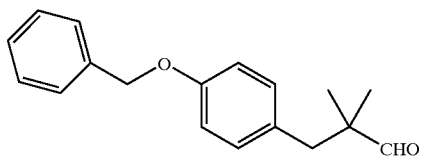

3-[4-(benzyloxy)phenyl]-2,2-dimethylpropanal

A mixture of NaOH (0.7 g), and (Bu)₄NI (0.15 g) in benzene (2.0 mL) and water (0.7 mL) was heated at 70° C. under argon to obtain a homogeneous mixture. To this mixture was added dropwise a mixture of isobutylaldehyde (1.44 g, Aldrich), and 4-benzyloxybenzyl chloride (3.5 g, Aldrich) in benzene (5.0 mL). After the addition, the resulting mixture was stirred at 70° C. for 3 h under argon. It was cooled, diluted with water, and extracted with EtOAc (3×25 mL). The combined organic extracts were washed with water, dried (anhydrous Na2SO4) and concentrated to dryness. This residue was purified by silica gel flash chromatography using 5% EtOAC in hexane. The appropriate fractions (monitored by TLC and ES mass spectrometry) were combined and concentrated to dryness to give the desired product (2.0 g, ~50%) as a white powder: Rf=0.28 (10% EtOAc/Hexane), ¹H -NMR (CDCl₃) δ9.56 (s, 1H), 7.4 (m, 5H), 6.99 (d, 2H), 6.83 (d, 2H), 5.02 (s, 2H), 2.71 (s, 2H), 1.02 (6H); ES-MS m/z 286 (M+18); HRMS calcd $C_{18}H_{20}O_{20}NH_4$ (M+NH₄) 286.2100, found 286.1833.

Step 2

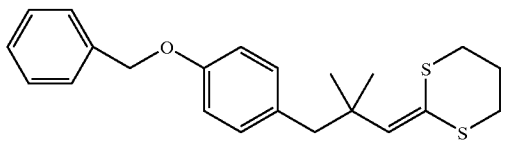

2-{3-[4-(benzyloxy)phenyl]-2,2-dimethylpropylidene}-1,3-dithiane

A solution of 2-trimethylsilyl-1,3-dithiane (0.8 mL, 1.2 equiv. Aldrich, STENCH !) in dry THF (10.0 mL) was cooled to −70° C., added dropwise BuLi (3.0 mL, 1.6 M) and stirred under argon for 15 min. Then added dropwise a solution of product from step A (0.95 g) in THF (10.0 mL). The resulting mixture was allowed to warm to −50° C. over a period of 2 h. During this period TLC (10% EtOAc in hexane), and ES mass spectrometry of the crude reaction mixture revealed completion of the reaction. The cold (31 50° C.) reaction mixture was quenched with saturated ammonium chloride solution (~25 mL), and extracted with EtOAc (3×25 mL). The combined organic extracts were washed with water (3×20 mL), dried (anhydrous Na₂SO₄) and concentrated to dryness. The residue (TLC in 10% EtOAc in hexane appeared to be one major product) was purified by silica gel flash chromatography using 5% EtOAC in hexane. The appropriate fractions (monitored by TLC and ES mass spectrometry) were combined and concentrated to dryness to give the title compound (0.95 g, 70% ) as a white solid: Rf=0.47 (10% EtOAc/Hexane); ¹H -NMR (CDCl3) δ7.4 (m, 5H), 7.06 9 d, 2H), 6.9 (d, 2H), 5.88 (s, 1H), 5.04 (s, 1H), 2.88 (m, 4H), 2.77 (s, 2H), 2.11 (m, 2H), 1.15 (s, 6H); ES-MS m/z 371(M+H); HRMS calcd $C_{22}H_{27}OS_2$ 371.1498, found 371.1521.

Step 3

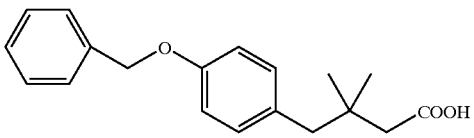

4-[4-(benzyloxy)phenyl]-3,3-dimethylbutanoic Acid

A solution of product from STEP 2 (0.4 g) in MeOH (3.00 mL) containing pTSA (0.05 g) and water (0.1 mL) was heated to reflux for 4 h. The reaction mixture was diluted with water (10 mL), and extracted with EtOAc (3×15 mL). The combined organic extracts were washed with water, dried over anhydrous Na₂SO₄, filtered and concentrated to dryness. The resulting residue was purified by silica gel flash chromatography using 5% EtOAc in hexane to a colorless liquid (0.29 g, Stench). This substance was treated with 1N NaOH (1.5 mL) and heated to reflux for 3 h. The reaction mixture was diluted with water (15.0 mL) and extracted with EtOAc (3×10 mL) to remove the thiol containing byeproducts. The aqueous phase was acidified with citric acid and extracted with EtOAc (3×15 mL). The combined organic extracts were washed with water, dried (anhydrous Na2SO4), and concentrated to dryness to give the title compound as a white solid (0.18 g, 56%). This can be further purified by crystallization from dichloromethane/hexane: Rf=0.31 (50% EtOAc/Hexane); ¹H-NMR (CDCl₃) δ7.37 (m, 5H), 7.08 (d, 2H); 6.88 (d, 2H); 5.03 (s, 2H); 2.61 (s, 2H); 2.21 (s, 2H) 1.02 (s, 6H); ES-MS m/z 297(M-H); HRMS calcd $C_{19}H_{22}O_3NH_4$ 316.1907, found 316.1924.

Step 4

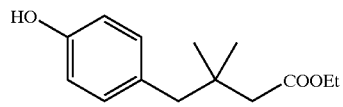

Ehyl 4-(4-hydroxyphenyl)-3,3-dimethylbutanoate

The acid from STEP 3 (0.5 g) was suspended in absolute EtOH (3.0 mL), added 4N HCl/dioxane (2.0 mL) and stirred overnight at room temperature, and heated to reflux for 1 h. The solution was concentrated to dryness and the residue was dissolved in EtOAC (15 mL), washed with water, dried and concentrated to dryness. The resulting syrup (0.4 g) was dissolved in EtOH (10 mL), added acetic acid (0.1 mL), Pd/C (10%, 0.25 g), and stirred in an atmosphere of hydrogen gas at 50 psi at room temperature. After 16 h, the catalyst was removed by filtration, and the filtrate was concentrated to dryness under reduced pressure. The resulting colorless syrup was dried in vacuo to give the title compound (0.34 g, 80%): Rf=0.44 (50% EtOAc/Hexane); ¹H -NMR (CDCl₃) δ7.02 (d, 2H); 6.73 (d, 2H); 4.12 (q, 2H); 2.58 (s, 2H); 2.15 (d, 2H); 1.24 (t, 3H); 0.98 (s, 6H); ES-MS m/z 235(M-H); HRMS calcd $C_{14}H_{21}O_3$ (MH⁺) 237.1485, found 237.1511.

Step 5

3,3-dimethyl-4-{4-[2-(5,6,7,8-tetrahydro-1,8-naphthyridin-2-yl)ethoxy]phenyl}butanoic Acid To a cold (5° C.) solution of 4-hydroxy-β,β-dimethylbenzenebutanoic ethyl ester (1, 0.15 g, 0.63 mmoles) in THF (3.0 mL), triphenyl-phosphine (0.25 g, 0.95 mmoles) was added and the mixture was stirred under an argon atmosphere. After 10 min, diisopropyldiazodicarboxylate (DIAD, 0.18 mL, 0.95 mmoles) was added and the mixture was stirred for another 15 min. To this mixture a solution of 2-(5,6,7,8-tetrahydro-1,8-naphthyridin-2-yl)-1-ethanol (1, 0.14 g, 0.79 mmoles) in THF (2.0 mL) was added and stirred for 30 min at 5° C., and at room temperature for 16 h. when a clear light brown solution was formed. This material was concentrated to dryness and purified by silica gel flash chromatography using ethyl acetate as the eluent to afford 0.1 g (32%) the desired product as a light brown oil: ES-MS m/z 397 (M+H); HR-MS calcd $C_{24}H_{33}N_2O_3$ 397.2491, found 397.2513. This ester was then dissolved in ethanol (1 mL), added 1M LiOH (1.0 mL) and heated at 80° C. for 4 h under an atmosphere of argon. The reaction mixture was cooled, diluted with water (1.0 mL), acidified with trifluoroacetic acid and purified by reverse-phase HPLC using 10–90% acetonitrile/water gradient (30 min) at a flow rate of 70 mL/min. The appropriate fractions were combined and freeze dried to give the desired product as a pale yellow solid: $^1$H-NMR (CD$_3$OD) δ7.4 (d, 1H, J=8.8 Hz); 7.08 (d, 2H, J=8.8 Hz); 6.81 (d, 2H, J=8.8 Hz); 6.74 (1H, d); 4.25 (t, 2H, J=6.0 Hz); 3.49 (t, 2H J=6 Hz); 3.13 (t, 2H, J=6.0 Hz); 2.81 (t, 2H, J=6.0 Hz); 2.59 (s, 2H), (s, 2H); 1.94 (m, 2H); 0.96 (s, 6H); ES-MS m/z 369 (M+H); HR-MS calcd $C_{22}H_{29}N_2O_3$ 369.2178, found 369.2179.

EXAMPLE 12

3-benzyl-3-methyl-4-{4-[3-(pyridin-2-ylamino)propoxy]phenyl}butanoic Acid

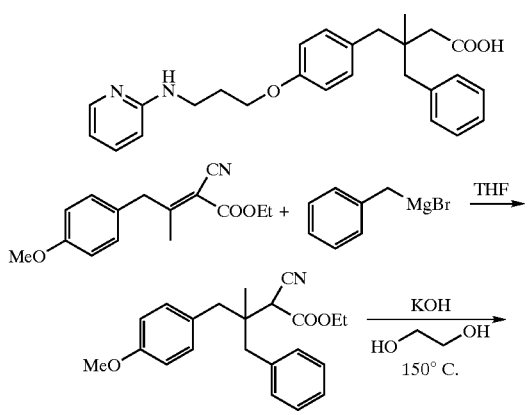

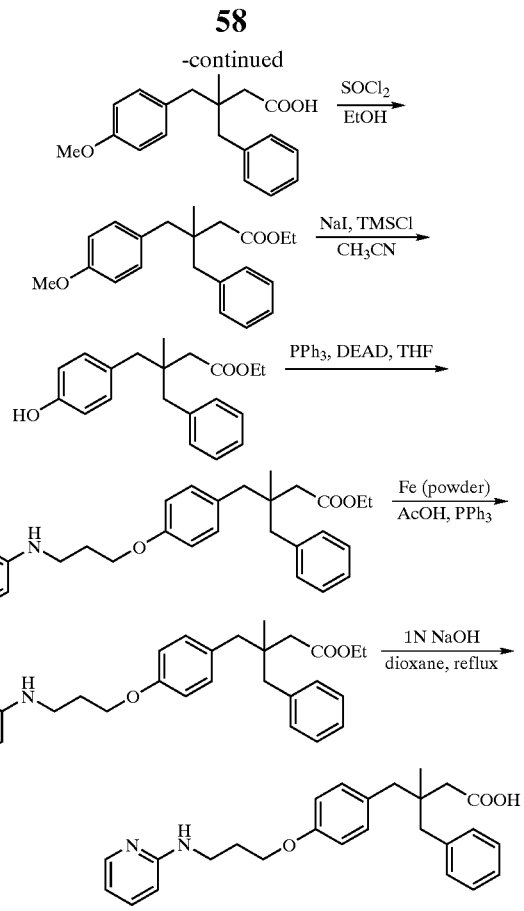

Step 1

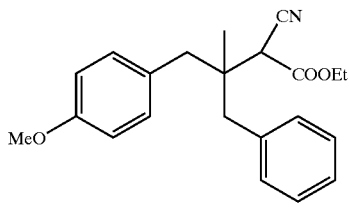

Ethyl 3-benzyl-2-cyano-4-(4-methoxyphenyl)-3-methylbutanoate

To a mixture of CuI (18.3 mg, 0.096 mmol) in anhydrous THF (3.6 mL) at RT under Ar gas was added benzylmagnesium bromide (5.5 mL, 11.1 mmol). The reaction mixture was cooled to 0° C. and ethyl (2E)-2-cyano-4-(4-methoxyphenyl)-3-methylbut-2-enoate (2.5 g, 9.6 mmol) in anhydrous THF (16 mL) was added slowly. The reaction mixture was stirred for 4 h at RT, quenched into 1N HCl and extracted with EtOAC (3×). The organic layers were combined, washed with brine, dried over Na$_2$SO$_4$, and concentrated to an oil. The oil was purified by flash chromatography using 15% EtOAc/Hexane as eluent. Obtained was ethyl 3-benzyl-2-cyano-4-(4-methoxyphenyl)-3-methylbutanoate (3.1 g, 8.8 mmol, 92%) as a diastereomeric mixture. LC-MS (MH+)=352. H NMR (DMSO-d$_6$) δ0.85 (s, 3H), 1.17 (t, 3H), 2.45–2.91 (m, 4H), 3.46 (s, 1H), 3.66 (s, 3H), 4.12 (q, 2H), 6.81 (m, 2H), 7.01 (d, 1H), 7.09 (m, 2H), 7.15–7.28 (m, 4H).

Step 2

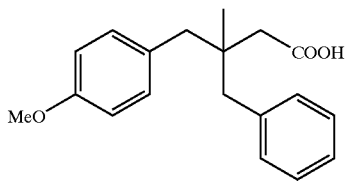

3-benzyl-4-(4-methoxyphenyl)-3-methylbutanoic acid

To ethyl 3-benzyl-2-cyano-4-(4-methoxyphenyl)-3-methylbutanoate (3.0 g, 8.7 mmol) in anhydrous ethylene glycol (30 mL) under Ar gas was added solid KOH (2.4 g, 43 mmol). The reaction mixture was heated at 150° C. for 60h. The reaction mixture was cooled to RT and quenched into 1N HCl. The resulting acidic mixture was extracted with EtOAc (3×). The organic layers were combined, washed with brine, dried over $Na_2SO_4$, and concentrated to an oil. The oil was purified by flash chromatography using 25% EtOAc/Hexane as eluent. Obtained was an oil 3-benzyl-4-(4-methoxyphenyl)-3-methylbutanoic acid (1.92 g, 6.4 mmol, 74%). LC-MS (M+Na)=321. H NMR (DMSO-$d_6$) δ0.88 (s, 3H), 2.03 (s, 2H), 2.65–2.92 (m, 4H), 3.82 (s, 3H), 6.94 (d, 2H), 7.17 (d, 2H), 7.25 (d, 2H), 7.31 (dd, 1H), 7.38 (dd, 2H), 12.25 (bs, 1H).

Step 3

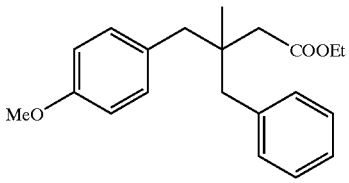

Ethyl 3-benzyl-4-(4-methoxyphenyl)-3-methylbutanoate

To 3-benzyl-4-(4-methoxyphenyl)-3-methylbutanoic acid (1.83 g, 6.1 mmol) in absolute ethanol (30 mL) at RT under Ar gas was added thionyl chloride (0.90 mL, 12.3 mmol). The reaction mixture was stirred at RT for 3 h and then refluxed for 2 h. The reaction mixture was concentrated to an oil and purified by flash column chromatography using 20% EtOAc/hexane as the eluent. Obtained was an oil ethyl 3-benzyl-4-(4-methoxyphenyl)-3-methylbutanoate (1.47 g, 5.1 mmol, 84%). LC-MS (M+Na)=349. H NMR (DMSO-$d_6$) δ0.81 (s, 3H), 1.21 (t, 3H), 2.02 (s, 2H), 2.56–2.77 (m, 4H), 3.73 (s, 3H), 4.09 (q, 2H), 6.85 (d, 2H), 7.08 (d, 2H), 7.15 (d, 2H), 7.22 (dd, 1H), 7.29 (dd, 2H).

Step 4

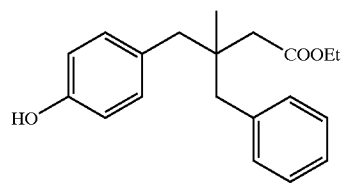

Ethyl 3-benzyl-4-(4-hydroxyphenyl)-3-methylbutanoate

To a solution of ethyl 3-benzyl-4-(4-methoxyphenyl)-3-methylbutanoate (500 mg, 1.5 mmol) and NaI (900 mg, 6.0 mmol) in anhydrous $CH_3CN$ (10 mL) at RT under Ar gas was added chlorotrimethylsilane (0.76 mL, 6.0 mmol). The reaction mixture was refluxed overnight and quenched into water (30 mL). The aqueous was extracted with EtOAc (3×). The organic layers were combined, washed with brine, dried over $Na_2SO_4$, and concentrated to an oil. The oil was purified by flash chromatography using 15% EtOAc/Hexane as eluent. Obtained was an oil ethyl 3-benzyl-4-(4-hydroxyphenyl)-3-methylbutanoate (286 mg, 0.92 mmol, 61%). LC-MS (M+Na)=335. H NMR (DMSO-$d_6$) δ0.79 (s, 3H), 1.20 (t, 3H), 2.01 (s, 2H), 2.53–2.77 (m, 4H), 4.09 (q, 2H), 6.67 (d, 2H), 6.95 (d, 2H), 7.15 (d, 2H), 7.22 (dd, 1H), 7.28 (dd, 2H).

Step 5

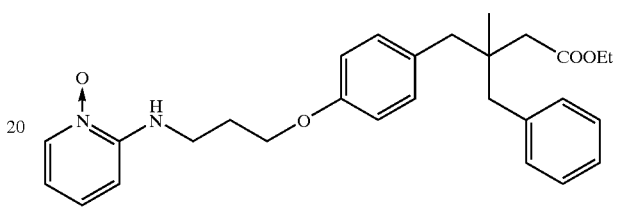

Ethyl 3-benzyl-3-methyl-4-(4-{3-[(1-oxidopyridin-2-yl)amino]propoxy}phenyl)butanoate To a mixture of ethyl 3-benzyl-4-(4-hydroxyphenyl)-3-methylbutanoate (275 mg, 0.88 mmol), 3-(pyridin-1-oxo-2-ylamino)propan-1-ol (178 mg, 1.06 mmol), and triphenylphosphine (278 mg, 1.06 mmol) in anhydrous THF (4 mL) under Ar gas at 0° C. was added slowly diethyl azodicarboxylate (166 µL, 1.06 mmol). The reaction mixture was stirred overnight. The solvent was removed under reduced pressure and the residue purified by flash column chromatography using 100% EtOAc, followed by 10% MeOH/$CH_2Cl_2$/$NH_4OH$ as eluents. Obtained was an oil ethyl 3-benzyl-3-methyl-4-(4-{3-[(1-oxidopyridin-2-yl)amino]propoxy}-phenyl)butanoate (329 mg). NMR consistent with structure and indicates impurity present. Compound was taken into next step as is.

Step 6

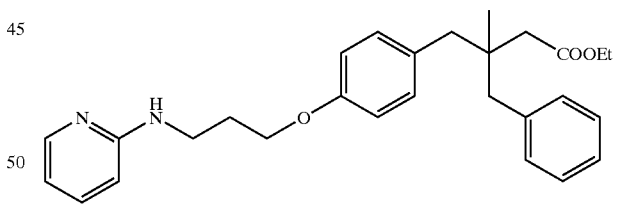

Ethyl 3-benzyl-3-methyl-4-{4-[3-(pyridin-2-ylamino)propoxy]phenyl}butan-oate

To ethyl 3-benzyl-3-methyl-4-(4-{3-[(1-oxidopyridin-2-yl)amino]propoxy}phenyl)butanoate (322 mg) and $PPh_3$ (220 mg, 0.84 mmol) in glacial acetic acid (5 mL) was added Fe powder (58 mg, 1.0 mmol). The reaction mixture was refluxed for 20 min and cooled to RT. The iron was removed by using a magnet and the mixture concentrated to an oil. The oil was purified by flash column chromatography using 80% EtOAc/hexane as eluent. Obtained was an oily ethyl 3-benzyl-3-methyl-4-{4-[3-(pyridin-2-ylamino) propoxy]phenyl}butan-oate (218 mg, 0.48 mmol, 2 step yield 55%). LC-MS (MH+)=447. H NMR (DMSO-$d_6$) δ0.81 (s, 3H), 1.20 (t, 3H), 1.95 (m, 2H), 2.02 (s, 2H), 2.54–2.78 (m, 4H), 3.37 (q, 2H), 4.02 (t, 2H), 4.09 (q, 2H), 6.43 (m, 2H), 6.55 (t, 1H), 6.85 (d, 2h), 7.06 (d, 2H), 7.15 (d, 2H), 7.21 (dd, 1H), 7.28 (d, 2H), 7.33 (dd, 1H), 7.95 (d, 1H).

Step 7

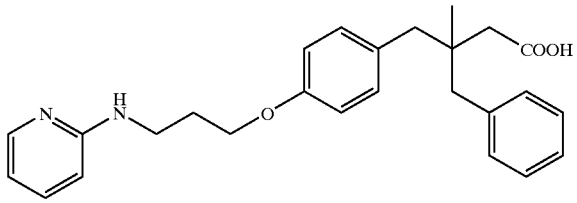

3-benzyl-3-methyl-4-{4-[3-(pyridin-2-ylamino) propoxy]phenyl}butanoic Acid

To Ethyl 3-benzyl-3-methyl-4-{4-[3-(pyridin-2-ylamino) propoxy]phenyl}butanoate (210 mg, 0.47 mmol) in dioxane (3 mL) was added 1N NaOH (3 mL). The reaction mixture was refluxed for 3.5 h, cooled to RT, acidified, and concentrated under reduced pressure. The residue was purified by gradient reverse phase HPLC using 10–50% acetonitrile/water/2% TFA as eluent. Obtained was 3-benzyl-3-methyl-4-{4-[3-(pyridin-2-ylamino) propoxy]phenyl}butanoic acid (131 mg). HRMS (MH+) calcd: 419.2249. Found: 419.2266. H NMR (DMSO-$d_6$) δ0.80 (s, 3H), 1.95 (s, 2H), 2.05 (m, 2H), 2.55–2.83 (m, 4H), 3.48 (m, 2H), 4.05 (t, 2H), 6.83 (dd, 1H), 6.85 (d, 2H), 7.02 (d, 1H), 7.08 (d, 2H), 7.16 (d, 2H), 7.23 (dd, 1H), 7.29 (dd, 2H), 7.84 (dd, 1H), 7.93 (d, 1H), 8.70 (bs, 1H), 12.2 (bs, 1H).

EXAMPLE 13

4-{3-bromo-4-[3-(pyridin-2-ylamino)propoxy]phenyl}-3,3-dimethylbutanoic Acid

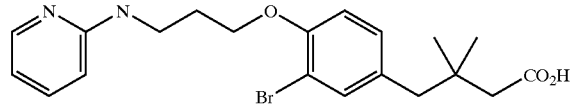

Step 1

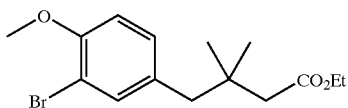

4-Methoxyphenyl-3,3-dimethylbutanoic acid ethyl ester (1.6 g, 6.4 mmol) was dissolved in glacial acetic acid (12.8 ml) and Bromine 1M in carbon tetrachloride (12.4 ml) was added and the reaction mixture was stirred at room temperature for 15 minutes under nitrogen atmosphere and concentrated and residue was neutralized with a saturated sodium bicarbonate solution. The alkaline solution was extracted with ethyl acetate and was washed with water, and dried over $Na_2SO_4$. The solid was filtered and concentrated to give 1.55 g (74%) of the desired product as oily gum. $^1$H NMR (CDCl$_3$) 7.38(s, 1H), 7.05(m, 1H), 6.82(d, 1H), 4.15 (q,2H),3.9(s,3H), 2.58(2H,s), 2.18(s,2H), 1.25(t,3H), 1.01 (s,6H).

Step 2

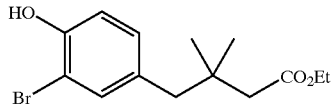

The product of STEP 1, Example 13 (0.987 g, 3.0 mmol) was dissolved in methylene chloride (10 ml) and was cooled to 0 C. and 1M boron tribromide in methylene chloride (6.0 ml) was added. The mixture was stirred at 0 C. for 30 minutes under nitrogen atmosphere. The reaction mixture was quenched with ethanol (2.0 ml) and was warmed to room temperature and was stirred at room temperature for 1 hour. The solvents were removed under reduced pressure. The residue was dissolved in ethyl acetate and was washed with a saturated solution of sodium bicarbonate and water, dried over $Na_2SO_4$. The solid was filtered and concentrated to yield 0.795 g (89.2%) of desired product as pale yellow oil. $^1$H NMR (CDCl$_3$) 7.30(m, 1H), 7.05(d, 1H), 6.95(d, 1H), 4.15(q,2H), 2.58(2H,s), 2.18(s,2H), 1.25(t,3H), 1.01(s, 6H).

Step 3

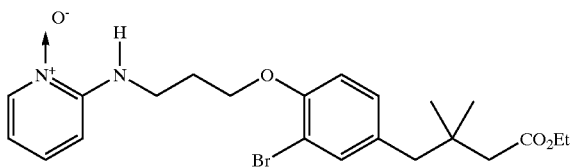

This compound was prepared following the procedure described in EXAMPLE 5, STEP 1 using the product of STEP 2. NMR spectrum of the product was consistent for the proposed structure.

Step 4

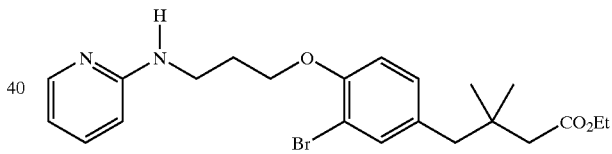

A mixture of the product of STEP 3 (2.2 g, 4.73 mmol), triphenylphosphine (1.1 g), iron powder(440 mg), in glacial acetic acid (20 ml) was heated to reflux and was allowed to reflux for 30 mins. Under nitrogen atmosphere. The mixture was cooled to room temperature and was filtered thorough celite and the filtrate was concentrated in vacuo. The residue was purified by chromatography on silica gel (CH$_2$Cl$_2$/CH$_3$OH/ NH$_4$OH: 97/2.5/0.5) to give 1.4 g of desired compound as oily gum. NMR spectrum was consistent for the proposed structure.

Step 5

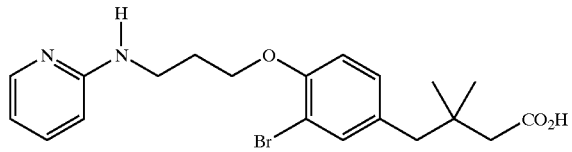

4-{3-bromo-4-[3-(pyridin-2-ylamino)propoxy]phenyl}-3,3-dimethylbutanoic acid trifluoroacetate hydrate The product of STEP 4 (150 mg) was dissolved in a mixture of 1.5 ml methanol and 1.5 ml of THF and 1.5 ml of 1N NaOH solution was added. The reaction mixture was stirred at ambient temperature for 5 hours. The volatile solvents were removed under vacuo and remaining aqueous solution was acidified with 1.5 ml of 1N HCl and was concentrated in vacuo to give a crude product. The crude product was purified on HPLC using acetonitrile water gradient 10–50% in 30 min to yield 89 mg of the title compound as TFA salt. $^1$H NMR (CD$_3$OD) 7.92(m, 1H), 7.85(m1H), 7.38(d, 1H), 7.18(m, 1H), 7.12(m, 1H), 7.0(d, 2H), 6.9(t, 1H), 4.2(t,2H), 3.69(t,2H), 2.62(2H,s), 2.25(m, 2H),2.12 (s1H), 1.01(s,6H); Anal. Calcd. for C$_{20}$H$_{25}$N$_2$O$_3$ plus 1.25 CF$_3$CO$_2$H, plus 0.25 H$_2$O: C,47.55; H,4.75; N,4.93. Found: C,47.34; H,4.62; N,5.11; Mass Spectrum: (MH+)=421.

EXAMPLE 14

4-{3-cyano-4-[3-(pyridin-2-ylamino)propoxy]phenyl}-3,3-dimethylbutanoic Acid

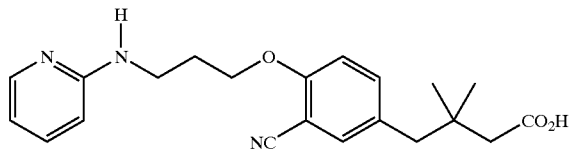

Step 1

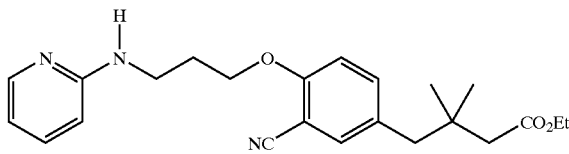

The final product of STEP 4, EXAMPLE 13 (500 mg) was dissolved in DMF (10 ml) and water (1.0 ml) and was treated with tris(dibenzylideneacetone) dipalladium(0) (51 mg) and bis(diphenylphosphino)ferrocene (75 mg).The reaction mixture was heated to reflux and was allowed to reflux for 20 hours under nitrogen atmosphere. The mixture was cooled to room temperature and was filtered through celite under vacuum. The filtrate was concentrated. The residue was dissolved in ethyl acetate and was washed with a saturated solution of ammonium chloride and dried over Na$_2$SO$_4$. The solid was filtered and the filtrate was concentrated. The cude product was purified by flash chromatography on silica gel (EA/Hexane/NH$_4$OH:80/19.5/0.5) to give 181 mg of desired compound as oily gum. NMR spectrum was consistent for the proposed structure.
Step 2

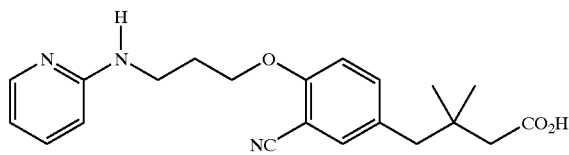

4-{3-cyano-4-[3-(pyridin-2-ylamino)propoxy]phenyl}-3,3-dimethylbutanoic Acid

The title compound was prepared following the procedure described in EXAMPLE 13, STEP 5 and replacing the product of EXAMPLE 13, STEP 3 with the product of STEP 1 to give crude product which was purified on HPLC using acetonitrile Water gradient 10–50% in 30 min to yield the title compound as TFA salt. $^1$H NMR (CD$_3$OD) 7.92(m, 1H), 7.85(m1H), 7.42(m, 2H), 7.13(m,2H), 6.9(t,1H), 4.32(t,2H), 3.69(t,2H), 2.62(2H,s), 2.25(m,2H), 2.12 (s1H), 1.01(s,6H); Anal. Calcd. for C$_{21}$H$_{25}$N$_3$O$_3$ plus 1.25 CF$_3$CO$_2$H: C,55.35; H,5.19; N,8.24. Found: C,55.67; H,5.36.; N,7.81; Mass Spectrum: (MH+)=368.

EXAMPLE 15

4-{3-ethynyl-4-[3-(pyridin-2-ylamino)propoxy]phenyl}-3,3-dimethylbutanoic Acid

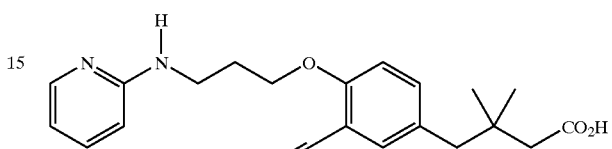

Step 1

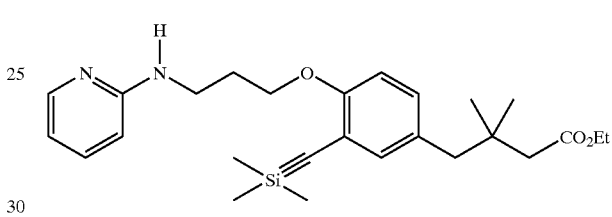

The final product of EXAMPLE 13, STEP 4 (500 mg) was dissolved in Et$_3$N (10 ml) was treated with CuI (40 mg), triphenylphosphine (80 mg), Pd(Ph$_3$P)$_2$Cl$_2$ (40 mg) and (trimethylsilyl) acetylene (1 ml). The reaction mixture was heated to 120 C. in a sealed tube for 20 hours under nitrogen atmosphere. The mixture was cooled to room temperature and was filtered through celite under vacuum. The filtrate was concentrated. The residue was dissolved in ethyl acetate and was washed with a saturated solution of ammonium chloride and dried over Na$_2$SO$_4$. The solid was removed by filtration and the filtrate was concentrated. The cude product was purified by flash chromatography on silica gel (EtOAc/Hexane/NH$_4$OH: 80/19.5/0.5) to give 181 mg of desired compound as oily gum. NMR spectrum was consistent for the proposed structure.
Step 2

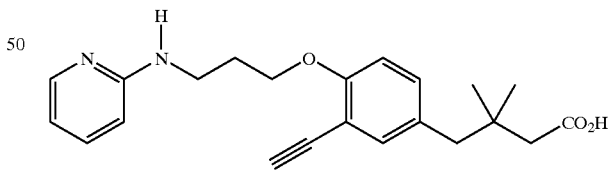

4-{3-ethynyl-4-[3-(pyridin-2-ylamino)propoxy]phenyl}-3,3-dimethylbutanoic Acid

This compound was prepared following the procedure described in EXAMPLE 14, STEP 5 and replacing the product of EXAMPLE 14, STEP 1 with the product of STEP 1 to give the desired crude product which was purified on HPLC using acetonitrile Water gradient 20–90% in 30 min to yield the title compound as TFA salt. $^1$H NMR (CD$_3$OD) 7.92 (m, 1H), 7.85 (m, 1H), 7.33–7.13(m,3H),6.98(d, 1H), 6.9(t,1H), 4.32(t,2H), 3.69(t,2H), 3.64 (s, 1H), 2.62(2H,s), 2.25(m,2H),2.12 (s,1H), 1.01(s,6H); Anal. Calcd. for $C_{22}H_{26}N_3O_3$ plus $1CF_3CO_2H$ plus 1 $CH_3OH$: C,58.59; H,6.10; N,5.47. Found: C,59.03; H,6.51.; N,5.37; Mass Spectrum: (MH+)=367.

EXAMPLE 16

5-(3-carboxy-2,2-dimethylpropyl)-2-[3-(pyridin-2-ylamino)propoxy]benzoic Acid

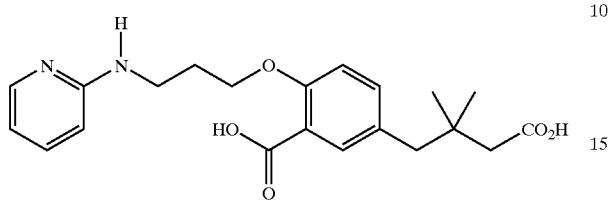

Step 1

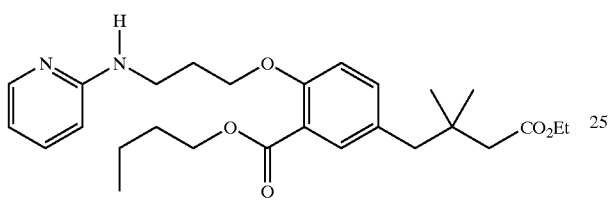

The product of EXAMPLE 13, STEP 4 (540 mg) was dissolved in diisopropylamine (7.5 ml) and n-butanol (7.5 ml). The solution was treated with $Pd(Ph_3P)_2Cl_2$ (60 mg). The reaction mixture was heated to 100 C. for 20 hours under carbon monoxide atmosphere. The mixture was cooled to room temperature and was filtered through celite under vacuum. The filtrate was concentrated. The residue was dissolved in ethyl acetate and was washed with a saturated solution of ammonium chloride and dried over $Na_2SO_4$. The solid was removed and the filtrate was concentrated. The cude product was purified on HPLC using acetonitrile Water gradient 20–90% in 30 min to yield 428 mg of title compound as TFA salt. NMR spectrum was consistent for the proposed structure. Mass Spectrum: (MH+)=471.2.

Step 2

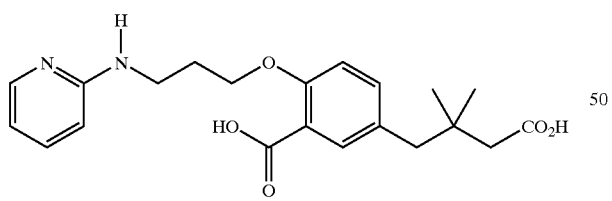

5-(3-carboxy-2,2-dimethylpropyl)-2-[3-(pyridin-2-ylamino)propoxy]benzoic Acid

The title compound was prepared following the procedure described in EXAMPLE 14, STEP 5 and replacing the product of EXAMPLE 14, STEP 1 with the product of STEP 1 to give the desired crude product which was purified on HPLC using acetonitrile Water gradient 20–90% in 30 min to yield the title compound as TFA salt. $^1$H NMR (DMSOd$_6$) 7.92(m, 1H), 7.85(m1H), 7.5(d, 1H),7.32(m, 1H),–7.05(m, 2H),6.85(m, 1H), 4.32(t,2H), 3.52(t,2H),3.64(s, 2.62(s,2H), 2.35(m,2H),2.12 (s1H), 9.93(s,6H); Anal. Calcd. for $C_{21}H_{26}N_3O_5$ plus $1.25CF_3CO_2H$ plus $0.25H_2O$: C,52.91; H,5.24; N,5.25. Found: C,52.97; H,5.02.; N,5.11; Mass Spectrum: (MH+)=386.

EXAMPLE 17

1-acetyl-4[[4-[3-(2-pyridinylamino)propoxy]phenyl]methyl]-4-piperidineacetic Acid

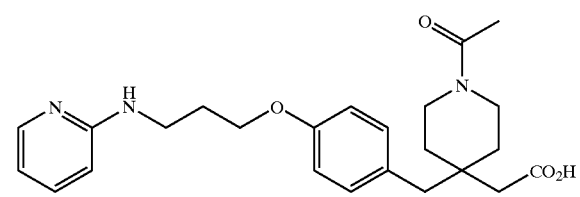

Step 1

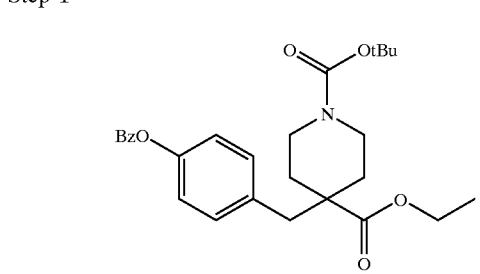

A solution of the starting material (22 g, 89 mmol) in 265 ml THF was added to a solution of lithium diisopropylamine (53 ml, 106 mmol, 2M solution) dropwise between –30° C. and –20° C. The resulting mixture allowed to warm to room temperature then cooled to –35° C. and 4-benzyloxybenzyl chloride (20.8 g, 89 mmol) was added all at once, then the resulting mixture was warmed to 25° C. After 24 hr, the reaction was quenched with water and extracted with ethyl acetate. The combined organic extracts were washed with $H_2O$, brine, and then dried with $MgSO_4$, and concentrated. The residue was purified by chromatography (on silica gel, ethyl acetate/hexane=1/4) to yield 23 g of a viscous oil. The $^1$H NMR spectrum of the product was consistent for the proposed structure.

Step 2

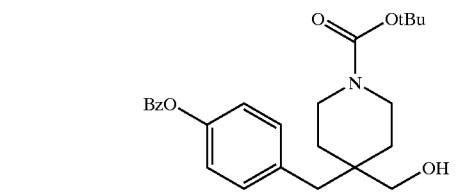

A solution of diisobutylaluminum hydride (41.0 ml, 41.20 mmol, 1M in THF) was added to a solution of the product of STEP 1 (22 g, 21 mmol) in 50 ml THF dropwise at –20° C. The resulting mixture was stirred at –20° C. for 30 min and allowed to slowly warm to room temperature. After 3 h, the reaction was diluted with ether (200 ml) and washed with aqueous 1M tartaric acid solution. The organic extracts were dried with $MgSO_4$, filtered and concentrated. The residue was purified by chromatography (on silica gel, ethyl acetate/hexane=1/3) to afford 4.2 g of a viscous oil in 0.58 g. The $^1$H NMR spectrum of the product was consistent for the proposed structure.

Step 3

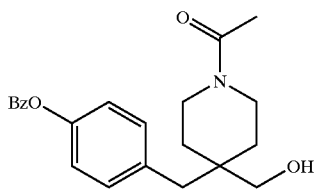

The product from STEP 2 (5.38 g; 13.0 mmole) was dissolved in 43 ml of THF and 43 mL of 4M HCl in dioxane the reaction was stirred at 25° C. until LCMS indicated the starting material had disappeared. The reaction mixture was evaporated to dryness under reduced pressure and then redissolved in ether and evaporated two times. The resulting crude mixture was dissolved in a solution containing 57 ml of methylene chloride, 10.8 ml of triethylamine (7.88 g; 77.8 mmol) and 80 mg of dimethylaminopyridine. After cooling to 0° C., 2.6 mL of acetic anhydride was added and then the reaction was allowed to warm to room temperature. After 18 h, the reaction was diluted with dichloromethane, washed with water and brine, then dried with $MgSO_4$, filtered and concentrated. The residue was dissolved in 108 ml of methanol. An aqueous, saturated $K_2CO_3$ solution (65 ml) was added at 0° C. The reaction was allowed to warm to room temperature. After 1.5 h, glacial acetic acid was added to adjust pH value to 6.5. The reaction was concentrated and product was extracted with ethyl acetate. The organic extracts were washed with brine, dried with $MgSO_4$, filtered and concentrated. The residue was purified by chromatography ($SiO_2$; $CH_2Cl_2$/MeOH/$NH_4OH$=90/10/0.2) to afford a viscous oil in 2.8 g. The $^1$H NMR spectrum of the product was consistent for the proposed structure.

Step 4

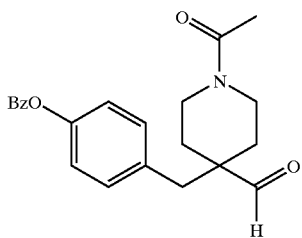

N-methyl morpholine-N-oxide (1.036 g, 2.94 mmol) and powdered 4 angstrom molecular sieves (2.945 g) were added to a solution of the product of STEP 3 (2.08 g, 5.89 mmol) in 82 ml of dichloromethane. Tetrapropylammonium perruthenate (103.6 mg, 0.29 mmol) was added at 0° C., and the reaction was allowed to warm to room room temperature. After 1.5 h, the reaction was filtered through a short column of silica gel (2") and washed with $CH_2Cl_2$/MeOH (9/1). The filtrate was concentrated, and the residue was purified by chromatography (on silica gel, $CH_2Cl_2$/MeOH/$NH_4OH$=95/5/0.1) to give a viscous oil in 1.08 g of the desired product. The $^1$H NMR spectrum of the product was consistent for the proposed structure.

Step 5

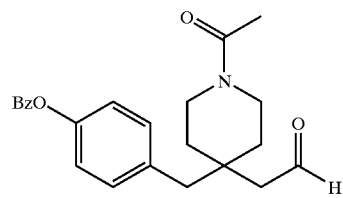

Lithium bis(trimethylsilyl)amide solution (4.6 ml, 4.6 mmol, 1.0M in THF) was added to a mixture of methoxymethyltriphenyl phosphonium chloride (1.58 g, 4.6 mmol) in 9 ml of THF dropwise at 0° C. After 15 min, it was added to a solution of the product of STEP 4 (1.95 g, 7.08 mmol) in 6 mL of THF at 0° C. The reaction was stirred for 1 h and quenched with $H_2O$. The product was extracted with dichloromethane. The aqueous layer was extracted with dichloromethane. The combined organic layers were washed with $H_2O$, brine, dried ($MgSO_4$) and concentrated. The residue was purified by chromatography ($SiO_2$; $CH_2Cl_2$/MeOH/$NH_4OH$=95/5/0.1) to yield an impure oil in 1.8 g. It was dissolved in 166 ml THF and 110 ml of a 2.0 N HCl solution. The reaction was stirred at room temperature for 1 h. The solution was transferred to a separatory funnel and extracted with ethyl acetate several times. The organic layer was washed with brine, dried with $MgSO_4$, and concentrated to give 1.6 g of product. The $^1$H NMR spectrum of the product was consistent for the proposed structure.

Step 6

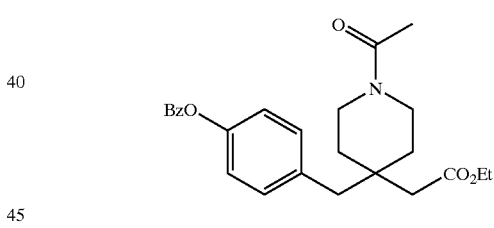

Silver nitrate (0.648 g, 3.82 mmol) was dissolved in 1 ml $H_2O$ and added to a solution of the product of step 5 (0.698 g, 1.91 mmol) in 9 ml ethanol. A solution resulting from dissolving of NaOH (0.301 g, 7.6 mmol) in 1.73 ml of $H_2O$ was added dropwise, then the reaction was stirred at room temperature or 2 h. The reaction was diluted with 7 ml $H_2O$ and then the ethanol was evaporated and then the resulting solution extracted with ethyl acetate. The water layer was acidified with aqueous 1 N HCl solution to pH=5, and extracted with ethyl acetate. The organic extracts were washed with brine, dried with $MgSO_4$, and concentrated to afford 0.371 gr of an oil. The oil was dissolved in 10 mL of 4N HCl in dioxane and 10 ml of absolute ethanol overnight at 25° C. The reaction was evaporated to dryness then taken up in ethyl acetate and extracted with a saturated solution of aqueous sodium bicarbonate. The organic extracts were washed with brine, dried ($MgSO_4$), filtered and evaporated to give the desired compound. The $^1$H NMR spectrum of the product was consistent with the proposed structure.

Step 7

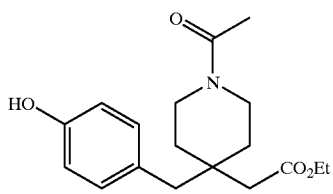

The product from STEP 6 (0.131 g) was dissolved in 25 ml of EtOH, followed by addition of 50 mg of 20% Pd(OH)$_2$/C. The reaction mixture was purged with nitrogen (5×), hydrogen (5×) and hydrogenated at 40 psi and room temperature for 2 h. The catalyst was removed by filtration and was washed with 2×20 ml of EtOH. Washes and filtrate were combined and evaporated to dryness to give the desired product. The $^1$H NMR spectrum of the product was consistent with the proposed structure.

Step 8

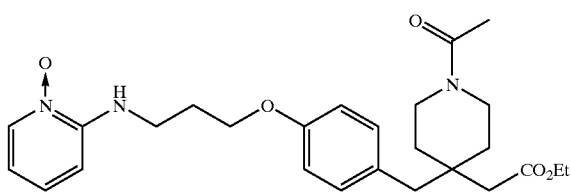

Diethyl azodicarboxylate (312 mg, 1.79 mmol) was added to a solution of the product of step 8 (406 mg, 1.26 mmol) and triphenylphosphine (508 mg, 1.94 mmol) in 4.5 ml THF at 0° C. and stirred for 15 min. 2-(3-Hydroxypropylamino) pyridine N-oxide (485 mg, 2.89 mmol) was added. The reaction was warmed to 40° C. After 15 min, the reaction was cooled to room temperature and stirred for 18 h. The reaction was concentrated and the residue was purified by chromatography (on silica gel, dichloromethane/2-propanol/acetic acid=95/5/0.5) to give a product as an impure mixture in 406 mg. The $^1$H NMR spectrum of the product was consistent for the proposed structure.

Step 9

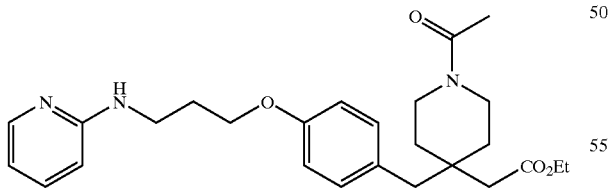

The product mixture of STEP 8 (482 mg), iron powder (100.5 mg, 1.8 mmol), triphenylphosphine (314 mg, 1.8 mmol), and acetic acid (8.5 ml) was heated at reflux for 30 min. The cooled reaction was filtered through a short column of Celite®, and washed with ethyl acetate. The filtrate was concentrated to give an oil. This product mixture was used without further purification. The $^1$H NMR spectrum of the product was consistent for the proposed structure.

Step 10

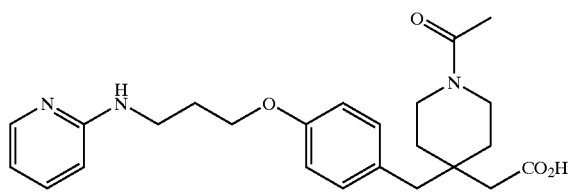

1-acetyl-4[[4-[3-(2-pyridinylamino)propoxy]phenyl]methyl]4-piperidineacetic Acid The product from STEP 9 was dissolved in 5 ml methanol and 5 ml 1N aqueous sodium hydroxide solution. The reaction was stirred at room temperature for 18 h, acidified with trifluoroacetic acid (0.35 ml), and concentrated. The residue was purified by reversed phase HPLC using water-acetonitrile gradient 10–50% in 30 min to yield 107 mg. $^1$H NMR (acetonitrile-d$_3$) δ1.38–1.66 (br, 4H); 2.09 (pentet, 2H); 2.11 (s, 3H); 2.22 (s, 2H); 2.74(s, 2H); 3.38 (b, 2H); 3.50 (t, 2H); 3.59 (b, 1H); 3.82(b, 1H); 4.02 (t, 2H); 6.78 (t, 1H); 6.82 (d, 2H); 6.97(d, 1H); 7.10 (d, 2H); 7.73 (d, 1H0; 7.82 (t, 1H). Anal. Calcd. for C$_{24}$H$_{31}$N$_3$O$_4$ plus CF$_3$CO$_2$H plus H$_2$O: C, 48.30; H, 5.09; N, 5.91. Found: C, 48.22; H, 4.82; N, 6.31.

EXAMPLE 18

(1-acetyl-3-{4-[3-(pyridin-2-ylamino)propoxy]benzyl}piperidin-3-yl)acetic Acid

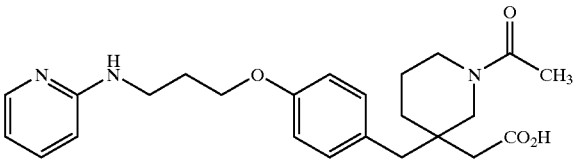

Step 1

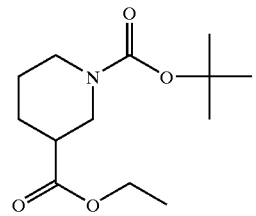

1-tert-butyl 3-ethyl piperidine-1,3-dicarboxylate

A solution of ethyl nipecotate (20.0 g, 127 mmol), di-tert-butyl dicarbonate (27.8 g, 127 mmol) in 60 ml THF was stirred at room temperature for 18 h. The solvent was evaporated, and residue was purified by chromatography (SiO$_2$, ethyl acetate/hexane=1/4) to give a viscous oil in 27.7 g (85%). The $^1$H NMR spectrum of the product was consistent for the proposed structure.

Step 2

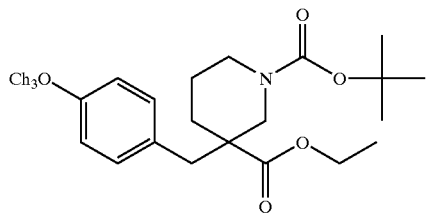

1-tert-butyl 3-ethyl 3-(4-methylbenzyl)piperidine-1,3-dicarboxylate

A solution of the product from STEP 1 (5.0 g, 19.5 mmol) in 20 ml THF was added to a solution of lithium diisopropylamine (11.7 ml, 23.4 mmol, 2M solution) in 25 ml THF dropwise at −20° C. The resulting mixture was stirred at 0° C. for 15 min and allowed to warm to room temperature. After 1 h, the reaction was cooled to −20° C. and treated, dropwise, with a solution of 4-methoxy-benzyl chloride (3.1 g, 19.5 mmol) in 20 ml THF. The resulting mixture was stirred at −10° C. for 1 h, and warmed to 35° C. After 1 h, the reaction was quenched with 25 ml saturated aqueous NH$_4$Cl solution. The product was extracted with ethyl acetate (2×100 ml). The aqueous layer was extracted with ethyl acetate. The combined layers were were washed with H$_2$O, brine, and then dried with Na$_2$SO$_4$, and concentrated. The residue was purified by chromatography (on silica gel, ethyl acetate/hexane=1/4) to yield a viscous oil in 5.2 g. The $^1$H NMR spectrum of the product was consistent for the proposed structure.

Step 3

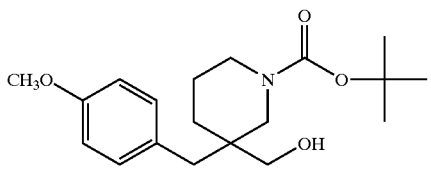

tert-Butyl 3-(hydroxymethyl)-3-(4-methylbenzyl)piperidine-1-carboxylate

A solution of diisobutylaluminum hydride (12.0 ml, 12.0 mmol, 1M in THF) was added dropwise to a solution of the product from STEP 2 (1.5 g, 6.0 mmol) in 15 ml THF at −20° C. The resulting mixture was stirred at −20° C. for 20 min and allowed to warm to room temperature. After 3 h, the reaction was diluted with ether (70 ml) and washed with 50 ml of aqueous 1M tartaric acid. The organic extracts were dried with MgSO$_4$, filtered and concentrated. The residue was purified by chromatography (SiO$_2$, ethyl acetate/hexane=1/3) to afford 0.58 g of a viscous. The $^1$H NMR spectrum of the product was consistent for the proposed structure.

Step 4

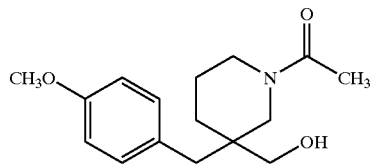

[1-acetyl-3-(4-methylbenzyl)piperidin-3-yl]methanol

Trifluoroacetic acid (12.5 ml) was added to a solution of the product from STEP 3 (0.48 g, 1.4 mmol) in 12.5 ml dichloromethane at 0° C. The reaction was allowed to warm to room temperature. After 2 h, the reaction was concentrated, and dried in vacuo. The residue was dissolved in 20 ml dichloromethane, then triethylamine (1.82 g, 18.0 mmol) and dimethylaminopyridine (30 mg) were added. Acetic anhydride (1.13 ml, 12.0 mmol) was added to the above mixture at 0° C. The reaction mixture was allowed to warm to room temperature. After 18 h, the reaction was diluted with 150 ml dichloromethane, washed with 10 ml H$_2$O, 5 ml brine, dried with MgSO$_4$, and concentrated. The residue was dissolved in 25 ml methanol. An aqueous saturated K$_2$CO$_3$ solution (15 ml) was added at 0° C. The reaction was allowed to warm to room temperature. After 1.5 h, glacial acetic acid was added to adjust PH value to 6.5. The reaction was concentrated and product was extracted with ethyl acetate. The organic extracts were washed with brine, dried with MgSO$_4$, and concentrated. The residue was purified by chromatography (SiO2, CH2Cl2/MeOH/NH$_4$OH=90/10/0.2) to afford 0.14 g of an viscous oil. The $^1$H NMR spectrum of the product was consistent for the proposed structure.

Step 5

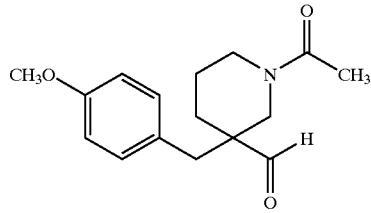

1-acetyl-3-(4-methylbenzyl)piperidine-3-carbaldehyde

N-methyl morpholine-N-oxide (0.19 g, 1.62 mmol) and powdered 4 angstrom molecular sieves (0.5 g) were added to a solution of the product from STEP 4 (0.3 g, 1.08 mmol) in 15 ml dichloromethane. Tetrapropyl-ammonium perruthenate (19 mg, 0.054 mmol) was added at 0° C., and the reaction was allowed to warm to room room temperature. After 1.5 h, the reaction was filtered through a short column of silica gel (2″) and washed with CH$_2$Cl$_2$/MeOH (9/1). The filtrate was concentrated, and the residue was purified by chromatography (SiO$_2$, CH$_2$Cl$_2$/MeOH/NH$_4$OH=95/5/0.1) to give 0.25 g of a viscous. The $^1$H NMR spectrum of the product was consistent for the proposed structure.

Step 6

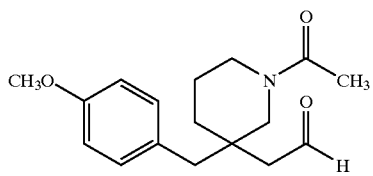

[1-acetyl-3-(4-methylbenzyl)piperidin-3-yl]
acetaldehyde

Under an atmosphere of $N_2$, lithium bis(trimethylsilyl) amide solution (10.6 ml, 10.6 mmol, 1.0M in THF) was added dropwise to a solution of methoxy methyltriphenyl phosphonium chloride (3.64 g, 10.6 mmol) in 15 ml THF at 0° C. After 15 min, this solution was added to a solution of the product of STEP 5 (1.95 g, 7.08 mmol) in 15 ml THF at 0° C. The reaction was stirred for 1 h and quenched with $H_2O$. The aqueous layer was extracted with dichloromethane. The combined organic layers were washed with $H_2O$, brine, dried with $Na_{0.2}SO_4$, filtered and concentrated. The residue was purified by chromatography ($SiO_2$, $CH_2Cl_2$/MeOH/$NH_4OH$=95/5/0.1) to yield an oil. It was dissolved in 40 ml THF and 40 ml 1.0 N aqueous HCl solution. The reaction was stirred at 25° C. for 2 h. Potassium carbonate powder was added to neutralize the reaction mixture. The solvent was evaporated and residue was extracted with ethyl acetate. The organic layer was washed with brine, dried with $MgSO_4$, and concentrated to give 1.6 g of product. The $^1H$ NMR spectrum of the product was consistent for the proposed structure.

Step 7

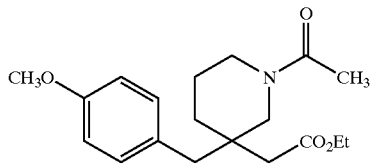

Ethyl [1-acetyl-3-(4-methylbenzyl)piperidin-3-yl]
acetate

Silver nitrate (1.87 g, 11.0 mmol) was dissolved in 3 ml $H_2O$. It was added to a solution of the product from STEP 6 (1.6 g, 5.5 mmol) in 25 ml ethanol. A solution prepared from dissolving NaOH (0.88 g, 22.0 mmol) in 4.0 ml $H_2O$ was added dropwise to the silver nitrate solution. The reaction was stirred at 25° C. for 2 h. The reaction was diluted with 15 ml $H_2O$. The ethanol was removed and the resulting residue was extracted with ethyl acetate (2×60 ml). The aqueous extracts were acidified with 1 N aqueous HCl solution to PH=5, and extracted with ethyl acetate (3×100 ml). The organic layer was washed with 15 ml brine, dried with MgSO4, filtered and concentrated to afford a 1.1 g of clean oil. The oil was dissolved in 30 ml ethanol and 15 ml 2M HCl/dioxane. The reaction was stirred at room temperature for 18 h and concentrated. The residue was purified by chromatography (on silica gel, $CH_2Cl_2$/MeOH/$NH_4OH$=95/5/0.1) to give 0.88 g of a gummy solid. The $^1H$ NMR spectrum of the product was consistent for the proposed structure.

Step 8

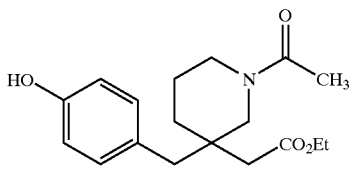

Ethyl [1-acetyl-3-(4-hydroxybenzyl)piperidin-3-yl]
acetate

A boron tribromide solution (3.85 ml, 3.85 mmol, 1.0 M in dichloromethane) was added to a solution of the product from STEP 7 (0.57 g, 1.71 mmol) in 1.8 ml dichloromethane. The reaction was stirred at room temperature for 5 h, and quenched with 0.393 ml ethanol. The mixture was diluted with ethyl acetate and dichloromethane and then washed with saturated aqueous $Na_2CO_3$ solution, dried with $MgSO_4$, filtered and concentrated. The residue was purified by chromatography ($SiO_2$, MeOH/$CH_2Cl_2$=5/95) to give 0.348 g of product. The $^1H$ NMR spectrum of the product was consistent for the proposed structure.

Step 9

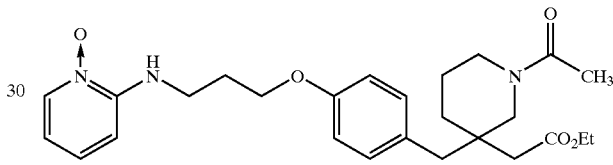

Ethyl [1-acetyl-3-(4-{3-[(1-oxidopyridin-2-yl)
amino]propoxy}benzyl)piperidin-3-yl]acetate Diethyl azodicarboxylate (267 mg, 1.53 mmol) was added to a solution of the product from STEP 8 (348 mg, 1.09 mmol) and triphenylphosphine (437 mg, 1.66 mmol) in 3.9 ml THF at 0° C. and stirred for 15 min. 2-(3-Hydroxypropylamino)pyridine N-oxide (418 mg, 2.48 mmol) was added. The reaction was warmed to 40° C. After 15 min, the reaction was cooled to room temperature and stirred for 18 h. The reaction was concentrated and the residue was purified by chromatography (on silica gel, dichloromethane/2-propanol/acetic acid=95/5/0.5) to give a product mixture in 406 mg. The $^1H$ NMR spectrum of the product was consistent for the proposed structure.

Step 10

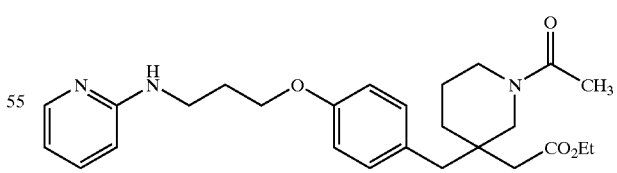

Ethyl (1-acetyl-3-{4-[3-(pyridin-2-ylamino)
propoxy]benzyl}piperidin-3-yl)acetate A mixture of the product from STEP 9 (335 mg), iron powder (74 mg, 1.3 mmol), triphenylphosphine (236 mg, 0.9 mmol), and acetic acid (6.3 ml) was heated at reflux for 30 min. The cooled reaction was filtered through a short column of Celite®, and washed with ethyl acetate. The filtrate was concentrated to give 108 mg of an colorless oil. This product mixture was used without further purification. The ¹H NMR spectrum of the product was consistent for the proposed structure.

Step 11

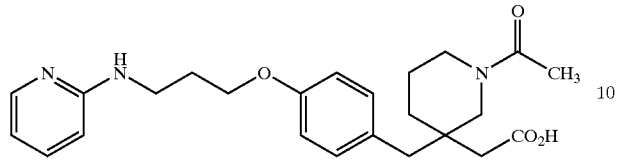

(1-acetyl-3-{4-[3-(pyridin-2-ylamino)propoxy]benzyl}piperidin-3-yl)acetic Acid

The product from STEP 10 (125 mg) was dissolved in 10 ml methanol and 10 ml 1N sodium hydroxide solution. The reaction was stirred at room temperature for 18 h, then acidified with trifluoroacetic acid (0.77 ml), and concentrated. The residue was purified on reverse phase HPLC using acetonitrile gradient 10–50% in 30 min to yield 90.7 mg. MS: (M+1)=426.2. ¹H NMR (CD₃CN) δ1.39–1.76 (cmplx bnd, 4H); 2.15, 2.07 (s, 3H); 2.12 (p, 2H); 2.14, 2.10 (d, 1IH); 2.17, 2.28 (d, 1H); 2.68, 2.75 (d, 1H); 2.73, 2.77 (d, 1H); 3.23, 3.14 (ddd, 1H); 3.11, 3.28 (d, 1H); 3.54 (t, 2H); 3.76, 3.68, (d, 1H); 3.61, 3.86 (dd, 1H); 4.08 (t, 2H); 6.82 (t, 1H); 6.85, 6.87 (d, 2H); 7.01 (d, 1H); 7.17, 7.13 (d, 2H); 7.73 (d, 1H); 7.86 (t, 1H). Note: many signals are doubled due to restricted rotation about amide bond. Two chemical shifts are listed for protons which have different shifts in the rotamers, with chemical shift of major rotamer listed first. Anal Calcd. for C₂₄H₃₁N₃O₄ plus 2.2 CF₃COOH: C, 49.77; H, 5.03; N, 6.13. Found: C, 49.47; H, 5.11; N, 6.49.

EXAMPLE 19

4-{3-bromo-5-fluoro-4-[3-(pyridin-2-ylamino)propoxy]phenyl}-3,3-dimethylbutanoic Acid

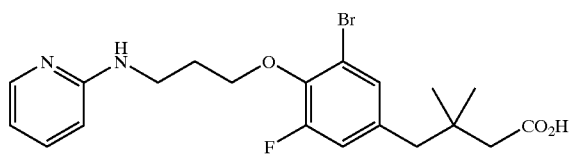

Step 1

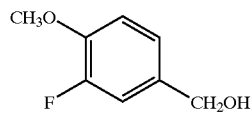

(3-fluoro-4-methylphenyl)methanol 3-fluoro-p-anisaldehyde (12.5 g, 81.1 mmol) was dissolved in 100 ml THF. Under N₂ a solution of diisobutylalumium hydride (100 ml, 1M in THF) was added at 0° C. over 30 min. The reaction was stirred for 30 min and quenched with 250 ml 1N HCl solution. The resulting mixture was stirred for 15 min and filtered through a short column of Celite®. The product was extracted with ethyl acetate. The aqueous layer was extracted with ethyl acetate. The combined organic layer was dried with MgSO₄, and concentrated to give a viscous oil in 11.6 g. This product was used without further purification. NMR spectra of the product were consistent for the proposed structure.

Step 2

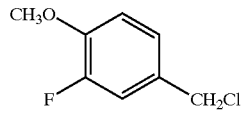

4-(chloromethyl)-2-fluoro-1-methylbenzene

Thionyl chloride (0.892 g, 7.5 mmol) was added to a solution of the product of STEP 1 (1.0 g, 6.4 mmol) in 10 ml ether dropwise at 0° C. After 30 min, the reaction was quenched with crushed ice carefully, and diluted with H₂O. The product was extracted with ether. The organic layer was washed with saturated NaHCO₃ solution, brine, dried with Na₂SO₄, and concentrated. The residue was purified by chromatography (on silica gel, ethyl acetate/hexane=1/9) to give a colorless liquid in 10.5 g. NMR spectra of the product were consistent for the proposed structure.

Step 3

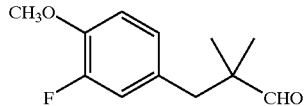

3-(3-fluoro-4-methylphenyl)-2,2-dimethylpropanal

Under argon, a mixture of sodium hydroxide (2.8 g, 70 mmol) and tetrabutylammonium iodide (0.6 g, 1.6 mmol) in 8 ml benzene and 2.8 ml H₂O was heated at 70° C. to form a homogeneous mixture. A mixture of the product of STEP 2 (10.5 g, 60.1 mmol) and isobutylaldehyde (5.76 g, 80 mmol) in 20 ml benzene was added to the above solution dropwise. The resulting mixture was heated at 70–75° C. for 6 h and cooled to room temperature. The product was extracted with ethyl acetate and washed with H₂O. The aqueous layer was extracted with ethyl acetate. The combined organic layer was washed with brine, dried with MgSO₄, and concentrated. The residue was purified by chromatography (on silica gel, ethyl acetate/hexane=5/95) to yield a colorless oil in 7.3 g. NMR spectra of the product were consistent for the proposed structure.

Step 4

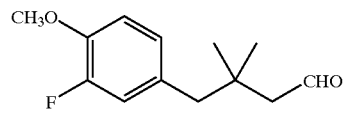

4-(3-fluoro-4-methylphenyl)-3,3-dimethylbutanal

A solution of lithium bis(trimethylsilyl)amide (55 ml, 55 mmol, 1M in THF) was added to a mixture methoxy methyl triphenyl phosphonium chloride (18.9 g, 55 mmol) in 65 ml THF dropwise at 0° C. and stirred for 15 min. It was added to a mixture of the product of STEP 3 (7.3 g, 34.7 mmol) in 35 ml THF dropwise at 0° C. After 5 min, the reaction was quenched with H₂O. The product was extracted with ethyl acetate. The aqueous layer was extracted with ethyl acetate. The combined organic layer was washed with H₂O, brine, dried with Na₀.₂SO₄, and concentrated. The residue was purified by chromatography (on silica gel, ethyl acetate/hexane=5/95) to give a colorless liquid in 6.3 g. This product was dissolved in 100 ml THF and 100 ml 2N HCl solution and heated at reflux for 30 min. The reaction was concentrated. The product was extracted with ethyl acetate and washed H₂O. The aqueous layer was extracted with ethyl acetate. The combined organic layer was washed with brine, dried with Na₂SO₄, and concentrated. The residue was purified by chromatography (on silica gel, ethyl acetate/hexane=15/85) to yield a colorless oil in 3.8 g. NMR spectra of the product were consistent for the proposed structure.

Step 5

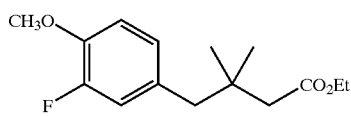

Ethyl 4-(3-fluoro-4-methylphenyl)-3,3-dimethylbutanoate

A solution of silver nitrate (5.76 g, 33.9 mmol) in 20 ml H₂O was added to a solution of the product of STEP 4 (3.8 g, 16.9 mmol) in 80 ml ethanol. A solution of Sodium hydroxide (2.71 g, 67.7 mmol) in 10 ml H₂O was added dropwise at room temperature. After 2 h, the reaction was filtered through a short column of Celite®. The filtrate was diluted with H₂O and extracted with ether (3×30 ml). The aqueous layer was acidified with concentrated HCl and extracted with chloroform. Chloroform layer was dried with MgSO₄ and concentrated. The residue was dissolved in 50 ml ethanol and 25 ml 4N HCl/dioxane solution. It was stirred at room temperature for 60 h and then concentrated to afford a colorless oil in 4.14 g. NMR spectra of the product were consistent for the proposed structure.

Step 6

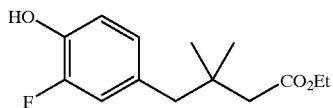

Ethyl 4-(3-fluoro-4-hydroxyphenyl)-3,3-dimethylbutanoate

The product of STEP 5 (0.75 g, 2.8 mmol) was dissolved in 10 ml dichloromethane. Under N₂ boron tribromide solution (5.6 ml, 5.6 mmol, 1M in dichloromethane) was added to above solution dropwise at 0° C. The reaction solution was allowed to warm to room temperature. After 30 min, the reaction was carefully quenched with ethanol. The product was extracted with ethyl acetate and washed with 1 N HCl. The organic layer was further washed with 5% NaHCO₃ solution, brine, dried with MgSO₄, and concentrated. The residue was purified by chromatography (on silica gel, ethyl acetate/hexane=1/4) to give a clean oil in 0.62 g. NMR spectra of the product were consistent for the proposed structure.

Step 7

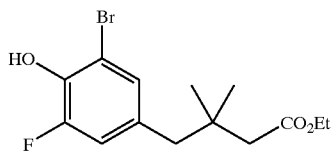

Ethyl 4-(3-bromo-5-fluoro-4-hydroxyphenyl)-3,3-dimethylbutanoate

Bromine solution (12.4 ml, 12.4 mmol, 1.0 M in CCl₄) was added a solution of the product of STEP 6 (1.58 g, 6.2 mmol) in 30 ml CCl₄ at 0° C. over 5 min. The reaction was stirred at room temperature for 30 min, and quenched with saturated NaHCO₃ solution. The product was extracted with ethyl acetate. The aqueous layer was extracted with ethyl acetate. The combined organic layer was washed brine, dried with Na₂SO₄, and concentrated. The residue was purified by chromatography (on silica gel, ethyl acetate/ hexane=1/9) to give a colorless oil in 0.73 g. NMR spectra of the product were consistent for the proposed structure.

Step 8

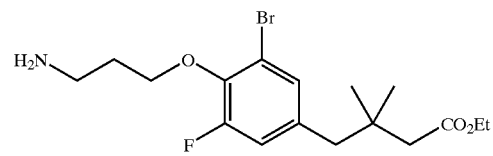

Ethyl 4-[4-(3-aminopropoxy)-3-bromo-5-fluorophenyl]-3,3-dimethylbutanoate

A solution of diethyl azodicarboxylate (0.488 g, 2.8 mmol) in 3 ml THF was added to a solution of the product of STEP 7 (0.72 g, 2.16 mmol) and triphenylphosphine (0.734 g, 2.8 mmol) in 13 ml THF at room temperature and stirred for 15 min. Tert-butyl N-(3-hydroxypropyl) carbamate (0.491 g, 2.8 mmol) was added. The reaction was stirred at room temperature for 18 h. THF was evaporated and the residue was purified by chromatography (on silica gel, ethyl acetate/hexane=1/4) to yield a golden oil in 0.87 g. This product was dissolved in 10 ml ethanol and 10 ml 4N HCl/dioxane and stirred at room temperature for 1 h. Solvents were evaporated to afford a light golden oil in 0.734 g. NMR spectra of the product were consistent for the proposed structure.

Step 9

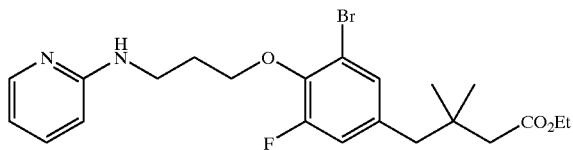

Ethyl 4-{3-bromo-5-fluoro-4-[3-(pyridin-2-ylamino)propoxy]phenyl}-3,3-dimethylbutanoate A mixture of the product of STEP 8 (0.725 g, 1.24 mmol), 4-methylmorpholine (1.01 g, 10 mmol), and 2-fluoropyridine (10 ml) was heated at 115° C. for 18 h under N₂. The cooled reaction was concentrated. The residue Step 10

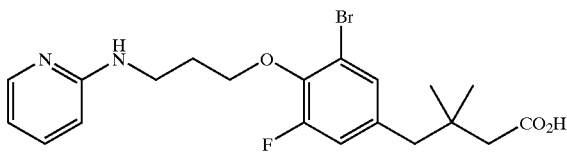

4-{3-bromo-5-fluoro-4-[3-(pyridin-2-ylamino)propoxy]phenyl}-3,3-dimethylbutanoic Acid The product of STEP 9 (0.254 g, 0.54 mmol) was dissolved in 10 ml methanol and 10 ml 1 N sodium hydroxide solution. The reaction was stirred at room temperature for 18 h, and acidified with trifluoroacetic acid (5 ml). Solvents were evaporated and residue was purified on HPLC using acetonitrile gradient 10–50% in 30 min to yield 0.213 g. NMR spectra of the product were consistent for the proposed structure. FAB-MS:(M+2)=441.3. H MNR (CDCl$_3$) δ1.05 (s, 6H), 2.20 (p, 2H), 2.22 (s, 2H), 2.63 (s, 2H), 2.68 (q, 2H), 4.20 (t, 2H), 6.74 (t, 1H), 6.93 (dd, 1H), 6.97 (s, 1H), 7.15 (s, 1H), 7.83 (m, 2H), 9.66 (br, 1H); Anal Calcd. for C$_{20}$H$_{24}$N$_2$O$_3$FBr plus 1.75 CF$_3$COOH: C, 44.18; H, 4.06; N, 4.38. Found: 44.05; H, 4.16; N, 4.25.

EXAMPLE 20

4-{3-fluoro-4-[3-(pyridin-2-ylamino)propoxy]phenyl}-3,3-dimethylbutanoic Acid

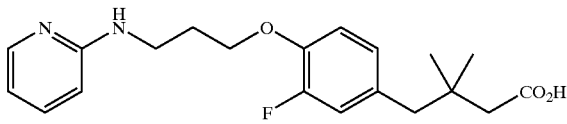

Step 1

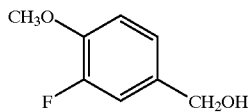

(3-fluoro-4-methylphenyl)methanol 3-fluoro-p-anisaldehyde (12.5 g, 81.1 mmol) was dissolved in 100 ml THF. Under N$_2$ a solution of diisobutylalumium hydride (100 ml, 1M in THF) was added at 0° C. over 30 min. The reaction was stirred for 30 min and quenched with 250 ml 1 N HCl solution. The mixture was stirred for 15 min and filtered through a short column of Celite®. The aqueous layer was extracted with ethyl acetate. The combined organic layer was dried with MgSO$_4$, and concentrated to give an oil in 11.6 g. This product was used without further purification. NMR spectra of the product were consistent for the proposed structure.

Step 2

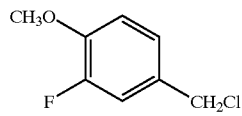

4-(chloromethyl)-2-fluoro-1-methylbenzene

Thionyl chloride (0.892 g, 7.5 mmol) was added to a solution of the product of STEP 1 (1.0 g, 6.4 mmol) dropwise at 0° C. After 30 min, the reaction was quenched with crushed ice carefully, and diluted with H$_2$O. The product was extracted with ether. The organic layer washed with saturated NaHCO$_3$, brine and dried with Na$_{0.2}$SO$_4$. Ether was evaporated and the residue was purified by chromatography (on silica gel, ethyl acetate/hexane=1/9) to give a clear liquid in 10.5 g. NMR spectra of the product were consistent for the proposed structure.

Step 3

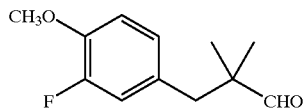

3-(3-fluoro-4-methylphenyl)-2,2-dimethylpropanal

Under argon, a mixture of sodium hydroxide (2.8 g, 70 mmol) and tetrabutylammonium iodide (0.6 g, 1.6 mmol) in 8 ml benzene and 2.8 ml H$_2$O was heated at 70° C. to form a homogeneous mixture. A mixture of the product of STEP 2 (10.5 g, 60.1 mmol) and isobutylaldehyde (5.76 g, 80 mmol) in 20 ml benzene was added to the above solution dropwise. The resulting reaction mixture was heated at 70–75° C. for 6 h. The product was extracted with ethyl acetate and washed with H$_2$O. The aqueous layer was extracted with ethyl acetate. The combined organic layer was washed with brine, dried with MgSO$_4$, and concentrated. The residue was purified by chromatography (on silica gel, ethyl acetate/hexane=5/95) to yield a colorless oil in 7.3 g (58%). NMR spectra of the product were consistent for the proposed structure.

Step 4

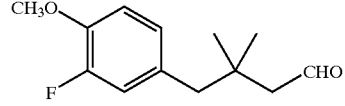

4-(3-fluoro-4-methylphenyl)-3,3-dimethylbutanal

Lithium bis(trimethylsilyl)amide solution (55 ml, 55 mmol, 1M in THF) was added to a mixture methoxy methyl triphenyl phosphonium chloride (18.9 g, 55 mmol) in 65 ml THF dropwise at 0° C. and stirred for 15 min and it was added to a mixture of the product of STEP 3 (7.3 g, 34.7 mmol ) in 35 ml THF dropwise at 0° C. After 5 min, the reaction was quenched with H$_2$O. The product was extracted with ethyl acetate. The aqueous layer was extracted with ethyl acetate. The combined organic layer was washed with H$_2$O, brine, dried with Na$_{0.2}$SO$_4$, and concentrated. The residue was purified by chromatography (on silica gel, ethyl acetate/hexane=5/95) to give a yellow liquid in 6.3 g. It was dissolved in 100 ml THF and 100 ml 2N HCl. The reaction was heated at reflux for 30 min and cooled to room temperature. THF was evaporated. The product was extracted with ethyl acetate and washed H₂O. The aqueous layer was extracted with ethyl acetate. The combined organic layer was washed with brine, dried with Na₂SO₄, and concentrated. The residue was purified by chromatography (on silica gel, ethyl acetate/hexane=15/85) to yield a colorless oil in 3.8 g. NMR spectra of the product were consistent for the proposed structure.

Step 5

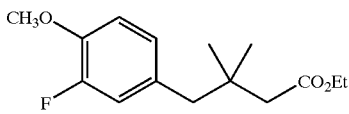

A solution of Silver Nitrate (5.76 g, 33.9 mmol) in 20 ml H₂O was added to a solution of the product of STEP 4 (3.8 g, 16.9 mmol) in 80 ml ethanol. A solution of Sodium hydroxide (2.71 g, 67.7 mmol) in 10 ml H₂O was added dropwise at room temperature. After 2 h, the reaction was filtered through a pad of Celite®. The residue was diluted with H₂O and extracted with ether (3×30 ml). The aqueous layer was acidified with concentrated HCl and extracted with chloroform. The organic layer was dried with MgSO₄ and concentrated. The residue was dissolved in 50 ml ethanol and 25 ml 4N HCl in dioxane. It was stirred at room temperature for 60 h. Ethanol and dioxane were evaporated to afford a clean product as a colorless oil in 4.14 g. NMR spectra of the product were consistent for the proposed structure.

Step 6

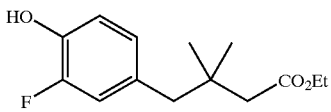

Ethyl 4-(3-fluoro-4-hydroxyphenyl)-3,3-dimethylbutanoate

The product of STEP 5 (0.75 g, 2.8 mmol) was dissolved in 10 ml methylene chloride. Under N₂ boron tribromide solution (5.6 ml, 5.6 mmol, 1M in methylene chloride) was added to above solution at 0° C. dropwise. The resulting reaction solution was allowed to warm to room temperature. After 30 min, the reaction was carefully quenched with ethanol. The product was extracted with ethyl acetate and washed with 1N HCl. The organic layer was washed with 5% NaHCO₃ solution, brine, dried with MgSO₄. and concentrated. The residue was purified by chromatography (on silica gel, ethyl acetate/hexane=1/4) to give an oil in 0.62 g. NMR spectra of the product were consistent for the proposed structure.

Step 7

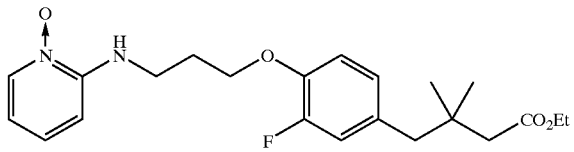

Ethyl 4-(3-fluoro-4-{3-[(1-oxidopyridin-2-yl)amino]propoxy}phenyl)-3,3-dimethylbutanoate A solution of diethyl azodicarboxylate (0.522 g, 3.0 mmol) in 6 ml THF was added to a solution of the product of STEP 6 (0.60 g, 2.36 mmol) and triphenylphosphine (0.786 g, 3.0 mmol) in 24 ml THF at room temperature and stirred for 15 min. 2-(3-Hydroxypropylamino)pyridine N-oxide (0.504 g, 3.0 mmol) was added. The reaction was stirred at room temperature for 18 h. THF was evaporated and the residue purified by chromatography (on silica gel, ethyl acetate/hexane=1/4) to yield a pale brown oil in 0.64 g. NMR spectra of the product were consistent for the proposed structure.

Step 8

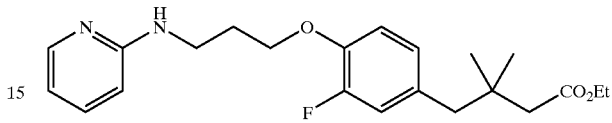

Ethyl 4-{3-fluoro-4-[3-(pyridin-2-ylamino)propoxy]phenyl}-3,3-dimethylbutanoate

A mixture of the product of STEP 7 (640 mg, 1.6 mmol), 10% Pd/C (400 mg, 0.36 mmol), cyclohexene (4.0 ml, 39.5 mmol), and 2-propanol (20 ml) was heated at reflux for 6 h. The reaction was allowed to cool to room temperature. An additional 10% Pd/C (250 mg, 0.23 mmol) and cyclohexene (2.0 ml, 19.8 mmol) were added. After 18 h of refluxing, the reaction was cooled to room temperature, filtered through a short column of Celite®, and washed with 100 ml 2-propanol. The filtrate was concentrated to give 380 mg oil. The NMR spectra were consistent for the proposed structure.

Step 9

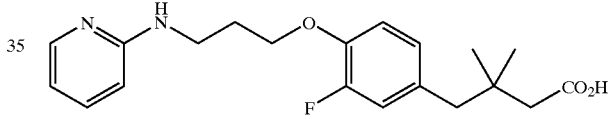

4-{3-fluoro-4-[3-(pyridin-2-ylamino)propoxy]phenyl}-3,3-dimethylbutanoic Acid

The product of STEP 8 (370 mg, 0.95 mmol) was dissolved in 20 ml methanol and 20 ml 1N sodium hydroxide solution. The reaction was stirred at room temperature for 16 h, and acidified with trifluoroacetic acid (3 ml). Solvents were evaporated and residue was purified on HPLC using acetonitrile gradient 10–50% in 30 min to yield 300 mg. FAB-MS: (MH+)=361. H NMR(CDCl₃) δ1.03 (s, 6H), 2.20 (s, 2H), 2.22 (p, 2H), 2.62 (s, 2IH), 3.58 (q, 2H), 4.14 (t, 2H), 6.72 (t, 1H), 6.86–6.98 (m, 4H), 7.70 (m, 2H); Anal. Calcd. for C₂₀H₂₅N₂O₃F plus 1.4 CF₃COOH: C, 52.66; H, 5.12; N, 5.39. Found: C, 52.56; H, 5.23; N, 5.09.

EXAMPLE 21

3-methyl-3-pyridin-3-yl-4-{4-[3-(pyridin-2-ylamino)propoxy]phenyl}butanoic Acid

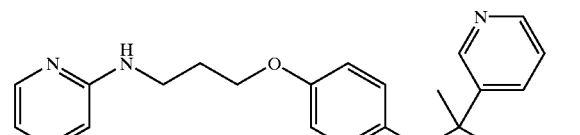

Step 1

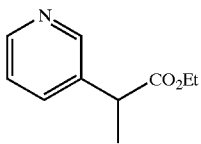

Ethyl 2-pyridin-3-ylpropanoate

A solution of Lithium bis(trimethylsilyl)amide (95 ml, 95 mmol, 1.0 M in THF) was added to a solution of ethyl-3-pyridyl acetate (15.0 g, 90.8 mmol) in 75 ml THF dropwise at −70° C. After 1 h, a solution of methyl iodide (14.2 g, 100 mmol) in 25 ml THF was added. The reaction was allowed to warm to room temperature, and poured into 5% $Na_2SO_3$ solution (400 ml). The product was extracted with ethyl acetate. The organic layer was washed with $H_2O$, brine, dried with $MgSO_4$, and concentrated. The residue was purified by chromatography (on silica gel, ethyl acetate/hexane=1/1) to give a brown liquid in 14.9 g. NMR spectra of the product were consistent for the proposed structure.

Step 2

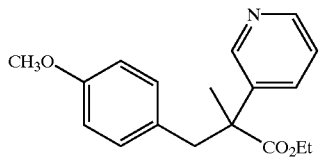

Ethyl 2-methyl-3-(4-methylphenyl)-2-pyridin-3-ylpropanoate

A solution of the product of STEP 1 (7.5 g, 42.1 mmol) was dissolved in 50 ml THF and a solution of lithium bis(trimethylsilyl)amide (45 ml, 45 mmol, 1.0 M in THF) was added dropwise at −70° C. The reaction was stirred at −70° C. for 1 h and a solution of 4-methoxybenzyl chloride (7.8 g, 50 mmol) in 25 ml THF was added. The reaction was allowed to warm to room temperature and quenched with 5%$Na_2SO_3$ solution (200 ml). The product was extracted with ethyl acetate (3×100 ml). The organic layer was washed with $H_2O$, brine, dried with $MgSO_4$, and concentrated. The residue was purified by chromatography (on silica gel, ethyl acetate/hexane=1/1) to give a brown liquid in 11.7 g. NMR spectra of the product were consistent for the proposed structure.

Step 3

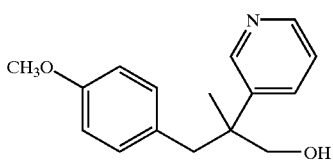

2-methyl-3-(4-methylphenyl)-2-pyridin-3-ylpropan-1-ol

A solution of diisobutylaluminum hydride 120 ml. 120 mmol, 1.0M in THF) was added to a solution of the product of STEP 2 (11.6 g, 38.7 mmol) in 100 ml THF at 0° C. over 20 min. After 1 h, the reaction was diluted with 25 ml ethyl acetate and quenched with 75 ml $H_2O$. The resulting mixture was filtered through a short column of Celite®, and washed with ethyl acetate. Filtrate was extracted with ethyl acetate (3×100 ml). The combined organic layer was washed with brine, dried with $MgSO_4$, and concentrated. The residue was purified by chromatography (on silica gel, ethyl acetate) to give a pale brown liquid in 4.1 g. NMR spectra of the product were consistent for the proposed structure.

Step 4

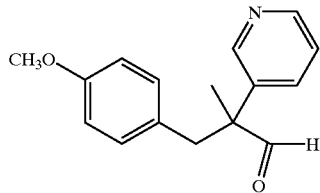

2-methyl-3-(4-methylphenyl)-2-pyridin-3-ylpropanal

A mixture of the product of STEP 3 (4.1 g, 16 mmol), N-methyl morpholine-N-oxide (2.9 g, 25 mmol), dry molecular sieves (8 g) and methylene chloride (35 ml) was stirred at room temperature for 15 min. Tetrapropylammoniumperruthenate (281 mg, 0.8 mmol) was added. The reaction was monitored by TLC, an additional N-methyl morpholine-N-oxide (0.73 g, 6.3 mmol), dry molecular sieves (2 g), and tetrapropylammoniumperruthenate (70.3 mg, 0.2 mmol) were added. After 2.5 h, the reaction mixture was filtered through a short column of Celite®. The filtrate was concentrated. The residue was purified by chromatography (on silica gel, ethyl acetate/hexane=4/1) to give a pale brown liquid in 1.66 g. NMR spectra of the product were consistent for the proposed structure.

Step 5

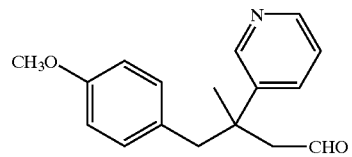

3-methyl-4-(4-methylphenyl)-3-pyridin-3-ylbutanal

Under $N_2$ Lithium bis(trimethylsilyl)amide solution (10.5 ml, 10.5 mmol, 1.0M in THF) was added to a mixture of methoxy methyltriphenyl phosphonium chloride (3.43 g, 10 mmol) in 25 ml THF dropwise at 0° C. After 15 min, it was added to a solution of the product of STEP 4 (1.65 g, 6.5 mmol) in 15 ml THF at 0° C. The reaction was stirred for 1 h and quenched with brine. The product was extracted with ethyl acetate. The organic layer was concentrated. The residue was dissolved in 50 ml THF and 50 ml 2N HCl solution. The reaction was stirred at room temperature for 18 h, and THF was evaporated. The residue was dilute with ethyl acetate and basified with 1N NaOH solution. The product was extracted thoroughly with ethyl acetate. The organic layer was washed with brine, and dried with $MgSO_4$, and concentrated. The residue was purified by chromatography (on silica gel, ethyl acetate/hexane=3/1) to yield a brown oil in 1.37 g. NMR spectra of the product were consistent for the proposed structure.

Step 6

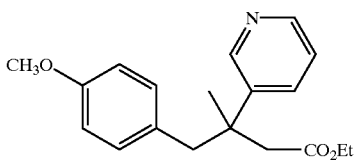

Ethyl 3-methyl-4-(4-methylphenyl)-3-pyridin-3-ylbutanoate

A solution of Silver Nitrate (1.73 g, 10.2 mmol) in 5 ml $H_2O$ was added to a solution of the product of STEP 5 (1.37 g, 5.1 mmol) in 40 ml ethanol. A solution of Sodium hydroxide (0.816 m g, 20.4 mmol) in 5 ml $H_2O$ was added dropwise at room temperature. After 2 h, the reaction was filtered through a short column of Celite®. The residue was diluted with $H_2O$, acidified with 1N HCl, and concentrated to give 0.7 g yellow solid. This yellow solid was dissolved in 15 ml ethanol and 15 ml 4N HCl in dioxane. The reaction was stirred at room temperature for 18 h. Ethanol and dioxane were evaporated. The residue was diluted with ethyl acetate and washed with 10% $K_2CO_3$ solution. The aqueous layer was extracted with ethyl acetate. The combined organic layer was washed brine, dried with $MgSO_4$, and concentrated to afford a pale brown oil in 0/584 g. NMR spectra of the product were consistent for the proposed structure.

Step 7

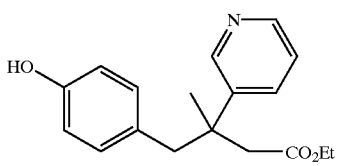

Ethyl 4-(4-hydroxyphenyl)-3-methyl-3-pyridin-3-ylbutanoate

The product of STEP 6 (0.58 g, 1.85 mmol) was dissolved in 10 ml methylene chloride. Under $N_2$, boron tribromide solution (3.5 ml, 3.5 mmol, 1M in methylene chloride) was added to the above solution dropwise at 0° C. The reaction was allowed to warm to room temperature. After 30 min, the reaction was carefully quenched with 10 ml ethanol. The resulting mixture was stirred for 10 min. The product was extracted with ethyl acetate and washed with 10% $K_2CO_3$ solution. The aqueous layer was extracted with ethyl acetate. The combined organic layer was washed brine, dried with $MgSO_4$, and concentrated. The residue was purified by chromatography (on silica gel, ethyl acetate/hexane=2/8) to give a pale brown oil in 0.197 g. NMR spectra of the product were consistent for the proposed structure.

Step 8

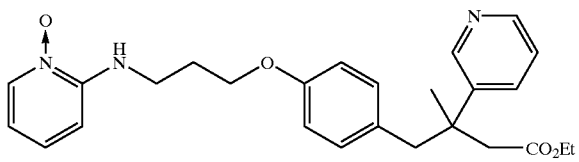

Ethyl 3-methyl-4-(4-{3-[(1-oxidopyridin-2-yl)amino]propoxy}phenyl)-3-pyridin-3-ylbutanoate A solution of diethyl azodicarboxylate (157 mg, 0.9 mmol) in 2 ml THF was added to a solution of the product of STEP 7 (197 mg, 0.66 mmol) and triphenylphosphine (236 mg, 0.9 mmol) in 5 ml THF at room temperature and stirred for 15 min. 2-(3-Hydroxypropylamino)pyridine N-oxide (168 mg, 0.9 mmol) was added. The reaction was stirred at room temperature for 18 h. THF was evaporated and the residue was purified by chromatography (on silica gel, $CH_2Cl_2/CH_3OH/NH_4OH$-98.5/1/0.5) to afford a clean product in 154 mg. NMR spectra of the product were consistent for the proposed structure.

Step 9

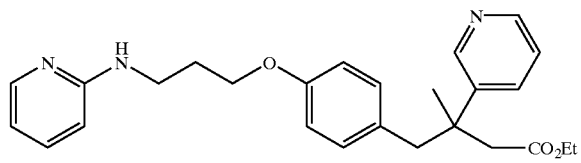

Ethyl 3-methyl-3-pyridin-3-yl-4-{4-[3-(pyridin-2-ylamino)propoxy]phenyl}-butanoate A mixture of the product of STEP 8 (150 mg, 0.33 mmol), iron powder (28 mg, 0.5 mmol), triphenylphosphine (87 mg, 0.33 mmol), and acetic acid (4.0 ml) was heated at reflux for 15 min. The cooled reaction was filtered through a short column of Celite®, and washed with ethyl acetate. The filtrate was concentrated. The residue was purified by chromatography (on silica gel, $CH_2Cl_2/CH_3OH/NH_4OH$-97.5/2/0.5) to afford a colorless oil in 148 mg. The NMR spectra were consistent for the proposed structure.

Step 10

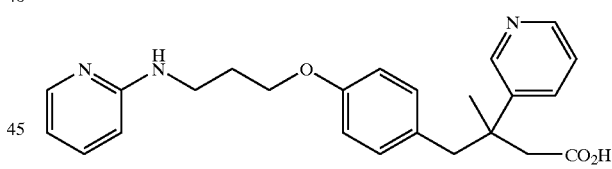

3-methyl-3-pyridin-3-yl-4-{4-[3-(pyridin-2-ylamino)propoxy]phenyl}butanoic Acid

The product of STEP 9 (148 mg, 0.35 mmol) was dissolved in 5 ml methanol and 5 ml 1N sodium hydroxide solution. The reaction was stirred at room temperature for 18 h, acidified with 2 ml trifluoroacetic acid, and concentrated. The residue was purified on HPLC using acetonitrile gradient 10–50% in 30 min to yield 90.6 mg. FAB-MS:(MH+)= 406.5. H NMR (DMSO-$d_6$) δ1.43 (s, 3H), 2.03 (p, 2H), 2.61 (d, 1H), 2.92 (d,1H), 2.96 (d, 1H), 3.07 (d, 1H), 3.48 (t, 2H), 4.01 (t, 2H), 6.76 (s, 4H), 6.85 (t,1H), 7.06 (d, 1H), 7.88 (m, 2H), 7.93 (d, 1H), 8.40 (d, 1H), 8.72 (d,1H), 8.76 (s, 1H), 8.90 (br, 1H); Anal Calcd. for $C_{24}H_{27}N_3O_3$ plus 2.75 $CF_3COOH$: C, 48.67; H, 4.26; N, 5.77. Found: 48.56; H, 4.29; N, 6.05.

EXAMPLE 22

4-{3-methoxy-4-[3-(pyridin-2-ylamino)propoxy]phenyl}-3,3-dimethylbutanoic Acid

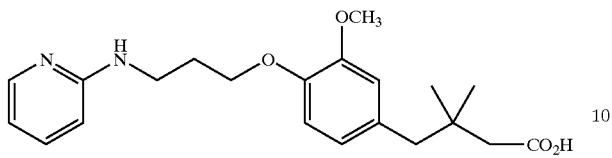

Step 1

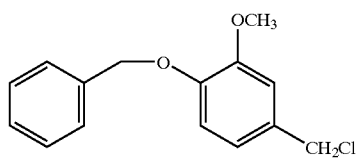

1-(benzyloxy)-4-(chloromethyl)-2-methoxybenzene

Thionyl chloride (5.95 g, 50.0 mmol) was added to a mixture of 4-benzyloxy-3-methoxybenzylalcohol (10.0 g, 40.9 mmol) in 50 ml ether at room temperature. The reaction turned into a clear solution and was monitored by TLC. The reaction was quenched with $H_2O$. The product was extracted with ether. The aqueous layer was extracted with ether. The combined organic layer washed with 5% $NaHCO_3$, brine and dried with $Na_2SO_4$. Ether was evaporated and the residue was purified by chromatography (on silica gel, ethyl acetate/hexane=2/8) to give a white solid 8.10 g. NMR spectra of the product were consistent for the proposed structure.

Step 2

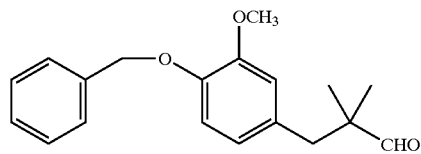

3-[4-(benzyloxy)-3-methoxyphenyl]-2,2-dimethylpropanal

Under argon, a mixture of sodium hydroxide (1.43 g, 35.85 mmol) and tetrabutylammonium iodide (0.30 g, 0.82 mmol) in 8 ml benzene and 2.8 ml $H_2O$ was heated at 70° C. to form a homogeneous mixture. A mixture of the product of Step 1 (8.05 g, 30.64 mmol) and isobutraaldehyde (2.95 g, 40.85 mmol) in 20 ml benzene was added to the above solution dropwise. The resulting reaction mixture was heated at 70–75° C. for 6 h. The product was extracted with ethyl acetate and washed with $H_2O$. The aqueous layer was extracted with ethyl acetate. The combined organic layer was washed with brine, dried with $MgSO_4$, and concentrated. The residue was purified by chromatography (on silica gel, ethyl acetate/hexane=1/9) to yield a colorless oil in 8.32 g. NMR spectra of the product were consistent for the proposed structure.

Step 3

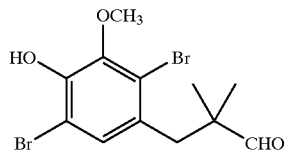

3-(2,5-dibromo-4-hydroxy-3-methoxyphenyl)-2,2-dimethylpropanal

The product of STEP 2 (6.0 g, 20.1 mmol) was dissolved in 25 ml chloroform. Bromine (7.2 g, 45 mmol) in 25 ml chloroform was added to above solution at 0° C. The reaction was allowed to warm to room temperature and poured into 10% $NaHSO_3$. The product was extracted with ethyl acetate. The organic layer was dried with $MgSO_4$ and concentrated. The residue was purified by chromatography (on silica gel, ethyl acetate/hexane=1/4) to give a viscous oil in 2.64 g. NMR spectra of the product were consistent for the proposed structure.

Step 4

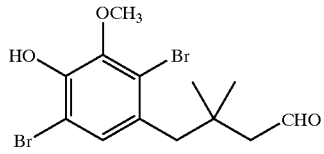

4-(2,5-dibromo-4-hydroxy-3-methoxyphenyl)-3,3-dimethylbutanal

Lithium bis(trimethylsilyl)amide solution (20 ml, 20 mmol, 1M in THF) was added to a mixture methoxy methyl triphenyl phosphonium chloride (6.9 g, 20 mmol) in 25 ml THF dropwise at 0° C. and stirred for 15 min and it was added to a mixture of the product of STEP 3 (2.6 g, 7.1 mmol) in 15 ml THF dropwise at 0° C. After 5 min, the reaction was quenched with $H_2O$. The product was extracted with ethyl acetate. The aqueous layer was extracted with ethyl acetate. The combined organic layer was washed with $H_2O$, brine, dried with $Na_{0.2}SO_4$, and concentrated. The residue was purified by chromatography (on silica gel, ethyl acetate/hexane=1/3) to give a brown oil in 1.14 g. It was dissolved in 20 ml THF and 20 ml 2N HCl. The reaction was stirred at room temperature for 30 min. THF was evaporated. The product was extracted with ethyl acetate and washed $H_2O$. The aqueous layer was extracted with ethyl acetate. The combined organic layer was washed with brine, dried with $Na_2SO_4$, and concentrated. The residue was purified by chromatography (on silica gel, ethyl acetate/hexane=1/3) to yield a viscous oil in 0.783 g. NMR spectra of the product were consistent for the proposed structure.

Step 5

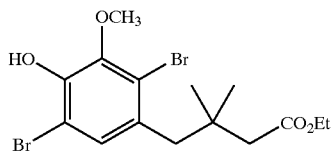

Ethyl 4-(2,5-dibromo-4-hydroxy-3-methoxyphenyl)-3,3-dimethylbutanoate

A solution of Silver Nitrate (0.722 g, 4.25 mmol) in 2.0 ml $H_2O$ was added to a solution of the product of STEP 4 (0.775 g, 2.04 mmol) in 20 ml ethanol. A solution of sodium hydroxide (2.71 g, 67.7 mmol) in 3.0 ml H₂O was added dropwise at room temperature. After 6 h, the reaction was filtered through a short column of Celite® and washed with H₂O. The filtrate was extracted with ether (3×30 ml). The aqueous layer was acidified with concentrated HCl and extracted with chloroform. The organic layer was dried with MgSO₄, concentrated and dried in vacuo. The residue (0.75 g) was dissolved in 15 ml ethanol and 15 ml 4N HCl in dioxane. The reaction was stirred at room temperature for 18 h and concentrated. The residue was purified by chromatography (on silica gel, ethyl acetate/hexane=3/7) to afford a pale brown oil in 0.536 g. NMR spectra of the product were consistent for the proposed structure.

Step 6

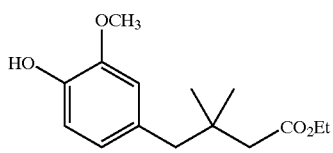

Ethyl 4-(4-hydroxy-3-methoxyphenyl)-3,3-dimethylbutanoate

A mixture of the product of STEP 5 (0.525 g, 1.3 mmol), 20% Pd/C, triethylamine (0.39 g, 3.9 mmol) in ethanol was subjected to hydrogenation conditions at 40 psi and room temperature for 1 h. The reaction was filtered through a short column of Celite® and concentrated. The residue was purified by chromatography (on silica gel, ethyl acetate/hexane= 1/3) to afford 0.19 g colorless oil. NMR spectra of the product were consistent for the proposed structure.

Step 7

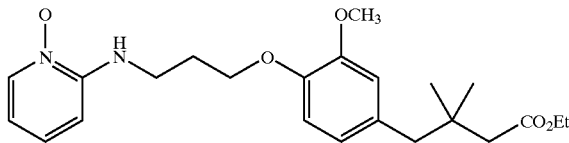

Ethyl 4-(3-methoxy-4-{3-[(1-oxidopyridin-2-yl)amino]propoxy}phenyl)-3,3-dimethylbutanoate A solution of diethyl azodicarboxylate (174 mg, 1.0 mmol) in 3 ml THF was added to a solution of the product of STEP 6 (18 mg, 0.676 mmol) and triphenylphosphine (262 mg, 1.0 mmol) in 7 ml THF at room temperature and stirred for 15 min. 2-(3-Hydroxypropylamino)pyridine N-oxide (168 mg, 1.0 mmol) was added. The reaction was stirred at room temperature for 18 h. THF was evaporated and the residue purified by chromatography (on silica gel, C₂HC₂I/CH₃OH/NH₄OH=97.5/2/0.5) to afford a pale brown oil in 81.5 mg). NMR spectra of the product were consistent for the proposed structure.

Step 8

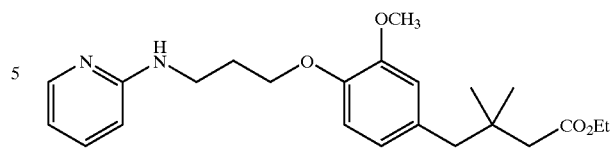

Ethyl 4-{3-methoxy-4-[3-(pyridin-2-ylamino)propoxy]phenyl}-3,3-dimethylbutanoate A mixture of the product of STEP 7 (81.5 mg, 0.2mmol), 10% Pd/C (50 mg, 0.05 mmol), cyclohexene (0.5 ml, 4.9 mmol), and 2-propanol (5 ml) was heated at reflux for 3 h. The reaction was cooled to room temperature, filtered through a short column of Celite®, and washed with 2-propanol. The filtrate was concentrated to give 67.5 mg pale brown oil. The NMR spectra were consistent for the proposed structure.

Step 9

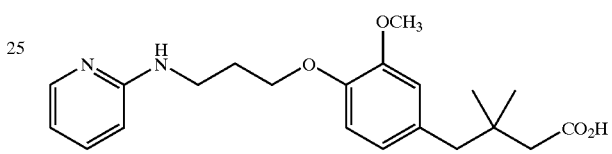

4-{3-methoxy-4-[3-(pyridin-2-ylamino)propoxy]phenyl}-3,3-dimethylbutanoic Acid

The product of STEP 8 (67.5 mg, 0.17 mmol) was dissolved in 5 ml methanol and 5 ml 1N sodium hydroxide solution. The reaction was stirred at room temperature for 16 h, and acidified with trifluoroacetic acid (1.0 ml). Solvents were evaporated and residue was purified on HPLC using acetonitrile gradient 10–50% in 30 min to yield 31.5 mg. FAB-MS: (MH+)=373. H NMR(CDCl₃) δ1.03 (s, 6H), 2.21 (p, 2H), 2.22 (s, 2H), 2.61 (s, 2H), 3.60 (q, 2H), 3.84 (s, 2H), 4.13 (t, 2H), 6.65–6.82 (m, 4H), 6.96 (d, 1H), 7.68–7.80 (m, 2H); Anal Calcd. for $C_{21}H_{28}N_2O_4$ plus 1.5 CF₃COOH: C, 52.17; H, 5.56; N, 5.07. Found: C, 52.44; H, 5.62; N, 4.88.

EXAMPLE 23

4-{3-chloro-4-[3-(pyridin-2-ylamino)propoxy]phenyl}-3,3-dimethylbutanoic Acid

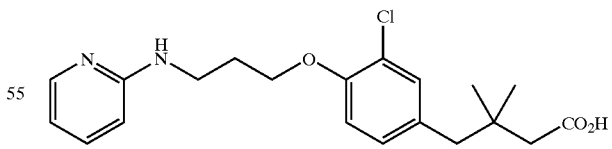

The title compound was prepared according to the procedure described for the synthesis of EXAMPLE 22. FAB-MS:(MH+)=377. H NMR (CDCl₃) δ1.03 (s, 6H), 2.21 (s, 2H), 2.24 (p, 2H), 2.61 (s, 2H), 3.63 (q, 2H), 4.14 (t, 2H), 6.71 (t, 1H), 6.86 (d, 1H), 7.00 (d, 1H), 7.05 (dd, 1H), 7.22 (d, 1H), 7.78 (t, 1H), 7.79 (d, 1H), 9.89 (br, 1H); Anal Calcd. for $C_{20}H_{25}N_2O_3Cl$ plus 2.0 CF₃COOH and 0.5 H₂O: C, 46.95; H, 4.60; N, 4.56. Found: C, 47.15; H, 4.65; N, 4.71.

EXAMPLE 24

3-Methyl-3-{4-[3-(pyridin-2-ylamino)-propoxy]-benzyl}-pent-4-enoic Acid

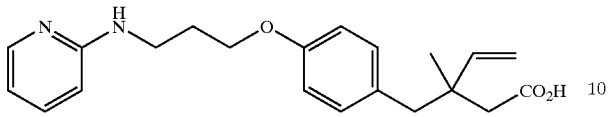

Step 1

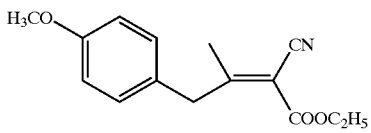

2-Cyano-4-(4-methoxy-phenyl)-3-methyl-but-2-enoic Acid Ethyl Ester

In a flask equipped with a Dean-stark trap was prepared a solution of 1-(4-Methoxy-phenyl)-propan-2-one (40 g), ethyl cyanoacetate (27.56 g), ammonium acetate (9.40 g), acetic acid (14.64 g) and toluene (150 ml) at room temperature. The solution was heated to reflux overnight. The solution was cooled to room temperature, washed with water and brine, and concentrated. The crude product was purified on a silica gel column, eluting with 10% ethyl acetate/hexane to afford colorless oil (40.76 g). The $^1$H NMR was consistent with the proposed structure.

Step 2

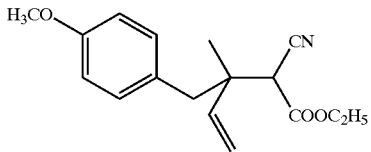

2-Cyano-3-(4-methoxy-benzyl)-3-methyl-pent-4-enoic Acid Ethyl Ester

To a solution of 1 M vinyl magnesium bromide/tetrahydrofuran (38.6 ml), copper iodine (0.08 g), and tetrahydrofuran (50 ml) was added the solution of product produced in STEP 1 (10.0 g) and ethyl ether (20 ml). The resulting solution was stirred at room temperature overnight. The solution was poured into 5% hydrochloric acid/water (100 ml). The organic layer was separated and the aqueous portion was extracted well with ethyl ether and the combined organic extract was washed with water, brine and dried over MgSO$_4$. The crude product was purified on a silica gel column, eluting with 10% ethyl acetate/hexane to afford light yellow oil (6.3 g). The $^1$H NMR was consistent with the proposed structure.

Step 3

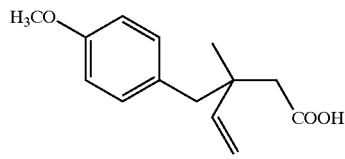

3-(4-Methoxy-benzyl)-3-methyl-pent-4-enoic Acid

A mixture of the product prepared in STEP 2 (5.8 g), ethylene glycol (15 mg) and KOH (5.6 g) was heated at 150 degrees for two days under nitrogen. The solution was cooled to room temperature and poured into 1% hydrochloric acid/water (200 ml). The aqueous portion was extracted well with ethyl acetate and the combined organic extract was washed with water, brine and dried over MgSO$_4$. Solvent was removed to give the crude product that was used without further purification. The $^1$H NMR was consistent with the proposed structure.

Step 4

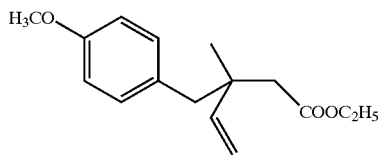

3-(4-Methoxy-benzyl)-3-methyl-pent-4-enoic Acid Ethyl Ester

A solution of product prepared in STEP 3 (5.6 g), saturated hydrochloric acid/ethanol (70 ml) was stirred at room temperature overnight. Solvent was removed. The crude product was purified on a silica gel column, eluting with 0.5% ethyl acetate/hexane to afford colorless oil (3.3 g). The $^1$H NMR was consistent with the proposed structure.

Step 5

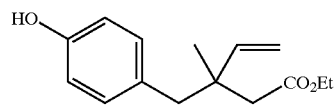

3-(4-Hydroxy-benzyl)-3-methyl-pent-4-enoic Acid Ethyl Ester

A solution of the product of STEP 4 (0.79 g) and dichloromethane (15 ml) was cooled to 0° C. A 1 M solution of boron tribromide in dichloromethane (6.00 ml) was added slowly. The solution was stirred at room temperature for 1 hour. Ethanol (5 ml) was added to quench the reaction. Solvent was removed. Residue was extracted with 1% of hydrochloric acid aqueous solution and ethyl acetate. The organic extract was washed with saturated sodium bicarbonate/water, and then dried over MgSO$_4$. Solvent was removed. The crude product was purified on a silica gel column, eluting with 20% ethyl acetate/hexane to afford colorless oil (0.32 g). The $^1$H NMR was consistent with the proposed structure.

Step 6

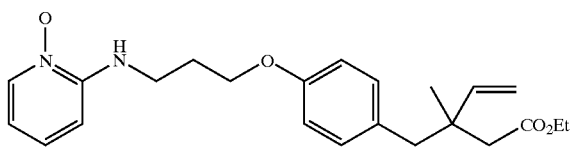

3-{4-[3-(1-Hydroxy-pyridin-2-ylamino)-propoxy]-benzyl}-3-methyl-pent-4-enoic Acid Ethyl Ester To a solution of the product of STEP 5 (0.62 g), triphenylphosphine (0.87 g) and tetrahydrofuran (12.5 ml) was added diethyl azodicarboxylate (0.54 ml). The solution was stirred for 5 minutes. 3-Propanol-pyridine-2-ylamine-1-oxide (0.56 g) was added. The resulting solution was stirred overnight. Solvent was removed. The crude product was purified on a silica gel column, eluting with dichloromethane/methanol/ammonium hydroxide (97.5:2:0.5) to afford a yellow oil (0.32 g). The $^1$H NMR was consistent with the proposed structure.

Step 7

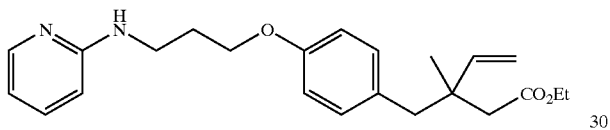

3-Methyl-3-{4-[3-(pyridin-2-ylamino)-propoxy]-benzyl}-pent-4-enoic Acid Ethyl Ester A solution of the product of STEP 6 (0.32 g), ion powder (0.07 g), triphenylphosphine (0.21 g), and acetic acid (8 ml) was heated to reflux for 15 minutes. The solution was cooled, filtrated through a celite bed, and washed with ethyl acetate. The filtrate was concentrated. The crude product was purified on a silica gel column, eluting with dichloromethane/methanol/ammonium hydroxide (97.5:2:0.5) to afford colorless oil (0.26 g). The $^1$H NMR was consistent with the proposed structure.

Step 8

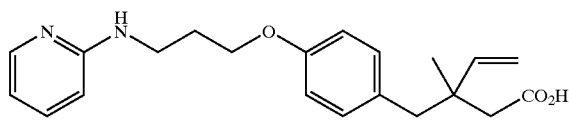

3-Methyl-3-{4-[3-(pyridin-2-ylamino)-propoxy]-benzyl}-pent-4-enoic Acid

A solution of the product of STEP 7 (0.26 g), 1 N sodium hydroxide in water (2 ml), and methanol (4 ml) was stirred overnight. Solvent was removed. The crude product was purified on a reverse phase HPLC using acetonitrile/water (0.5% TFA) gradient to give colorless oil (0.150 g). Anal. MS (APCI): m/z=355 (MH$^+$), $^1$H NMR (500 MHz, CD$_3$OD): δ1.09 (3H, s), 2.16 (2H, m), 2.25 (2H, q), 2.70 (2H, s), 3.59 (2H, t), 4.08 (2H, t), 4.85 (1H, d), 4.98 (1H, d), 5.92 (1H, dd), 6.81 (2H, d), 6.84 (1H, t), 7.07 (3H, m), 7.79 (1H, d), 7.86 (1H. t). Calcd. for C$_{21}$H$_{26}$N$_2$O$_3$+1.1 TFA: C, 58.07; H, 5.69; N, 5.84, Found: C, 57.87; H, 5.77; N, 5.70.

EXAMPLE 25

4-{2-bromo-4-[3-(pyridin-2-ylamino)propoxy]phenyl}-3,3-dimethylbutanoic Acid

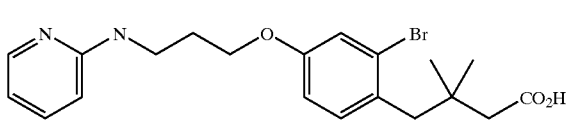

Step 1

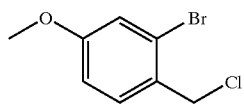

2-bromo-1-(chloromethyl)-4-methoxybenzene 2-bromo-1-(chloromethyl)-4-methoxybenzene was prepared following the method described by Skorcz,J. A.; Robertson,J. E.; J.Med.Chem.; 8; 1965; 255–257.

Step 2

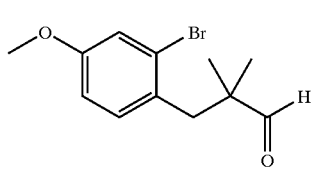

3-(2-bromo-4-methoxyphenyl)-2,2-dimethylpropanal

A mixture of NaOH (4.9 g), and (Bu)$_4$NI (1 g) in benzene (14 mL) and water (4.9 mL) was heated at 70° C. under argon to obtain a homogeneous mixture. To this mixture was added dropwise a mixture of isobutylaldehyde (10.1 g, 140 mmoles), and the product of Step 1 (25 g, 106 mmoles) in benzene (38 mL). After the addition, the resulting mixture was stirred at 70° C. for 6 h under argon. It was cooled, diluted with water, and extracted with EtOAc (3×150 mL). The combined organic extracts were washed with water, dried (Na$_2$SO$_4$) and concentrated to dryness. This residue was purified by silica gel flash chromatography using 5% EtOAc in hexane. The appropriate fractions (monitored by TLC) were combined and concentrated to dryness to give the desired product (14.9 g, ~50%). NMR spectrum of the product was consistent for the proposed structure.

Step 3

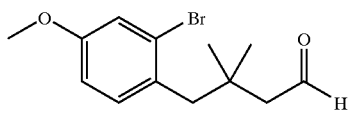

4-(2-bromo-4-methoxyphenyl)-3,3-dimethylbutanal

Lithium bis(trimethylsilyl)amide solution (88 mL, 88 mmoles, 1.0M in THF) was added to a mixture of methoxymethyltriphenyl phosphonium chloride (30.2 g, 88 mmoles) in 200 ml of THF dropwise at 0° C. After 15 min, it was added to a solution of 3-(2-bromo-4-methoxyphenyl)-2,2-dimethylpropanal (14 g, 51.7 mmoles) in 100 mL of THF at 0° C. The reaction was stirred for 5 minutes and quenched with H$_2$O. The product was extracted with ethyl acetate (3×200 mL). The combined organic layer was washed with brine, dried (Na$_2$SO$_4$) and concentrated. The residue was purified by flash chromatography (5% ethyl acetate in hexane) to yield an impure oil ~12 g. It was dissolved in 150 mL THF and 150 mL of a 2.0 N HCl solution. The reaction was stirred at room temperature for 30 minutes. The reaction mixture was extracted with ethyl acetate (3×200 mL). The organic layer was washed with brine, dried (Na$_2$SO$_4$), and concentrated to give 11 g of product. NMR spectrum of the product was consistent for the proposed structure.

Step 4

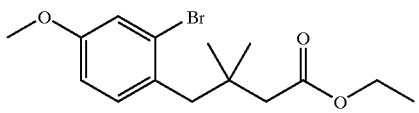

Ethyl 4-(2-bromo-4-methoxyphenyl)-3,3-dimethylbutanoate

Silver nitrate (21 g, 124 mmoles) was dissolved in 35 mL H$_2$O and added to a solution of 4-(2-bromo-4-methoxyphenyl)-3,3-dimethylbutanal (11 g, 38.6 mmoles) in 250 mL ethanol. A solution of NaOH (10 g, 250 mmoles) in 35 mL of H$_2$O was added dropwise, then the reaction was stirred at room temperature for 2 hours. The reaction was passed through a short pad of Celite. Then, the ethanol was evaporated and the residue was partioned between water and ethyl acetate. The aqueous layer was extracted with ethyl acetate (2×200 mL). The organic layers were discarded. The water layer was acidified with 2 N HCl solution to pH=2, and extracted with ethyl acetate (3×200 mL). The organic extracts were washed with brine, dried (Na$_2$SO$_4$), and concentrated to afford an oil. The oil was dissolved in 60 mL of 4N HCl in dioxane and 120 mL of absolute ethanol overnight at 25° C. The reaction was evaporated to dryness then taken up in ethyl acetate and extracted with a saturated solution of aqueous sodium bicarbonate, brine, dried (Na$_2$SO$_4$), and evaporated to give 9.1 g (71%) of the desired compound. NMR spectrum of the product was consistent for the proposed structure.

Step 5

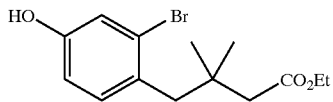

Ethyl 4-(2-bromo-4-hydroxyphenyl)-3,3-dimethylbutanoate

Ethyl 4-(2-bromo-4-methoxyphenyl)-3,3-dimethylbutanoate (4.5 g, 13.7 mmoles) was dissolved in methylene chloride (60 mL) and was cooled to 0° C. and 1M boron tribromide in methylene chloride (27.0 mL) was added. The mixture was stirred at 0° C. for one hour under nitrogen atmosphere. The reaction mixture was quenched with ethanol (60.0 mL) and was warmed to room temperature and was stirred at room temperature for 1 hour. The solvents were removed under reduced pressure and residue was dissolved in ethyl acetate and was washed with a saturated solution of sodium bicarbonate and water, dried (Na$_2$SO$_4$) and concentrated to yield 4.0 g (93%) of desired product. NMR spectrum of the product was consistent for the proposed structure.

Step 6

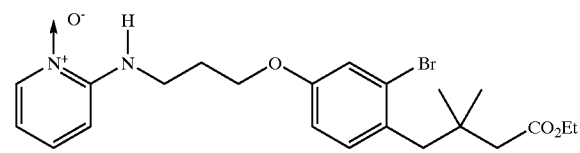

This compound was prepared following the procedure described in Example 5, Step 7, and replacing the product of Example 5, Step 6 with ethyl 4-(2-bromo-4-hydroxyphenyl)-3,3-dimethylbutanoate, this Example, Step 6. NMR spectrum of the product was consistent for the proposed structure.

Step 7

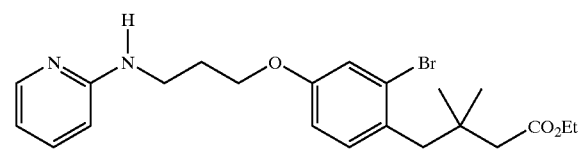

Ethyl 4-{2-bromo-4-[3-(pyridin-2-ylamino)propoxy]phenyl}-3,3-dimethylbutanoate

A mixture of the product of Step 7 (1.0 g, 2.15 mmoles), triphenylphosphine (500 mg, 2 mmoles), iron powder (200 mg), in glacial acetic acid (10 ml) was heated to reflux and was allowed to reflux for 30 minutes, under nitrogen atmosphere. The mixture was cooled to room temperature and was filtered thorough Celite and the filtrate was concentrated in vacuo. The residue was purified by flash chromatography (CH$_2$Cl$_2$/CH$_3$OH/NH$_4$OH:96/3/1) to give 790 mg of desired compound. NMR spectrum was consistent for the proposed structure.

Step 8

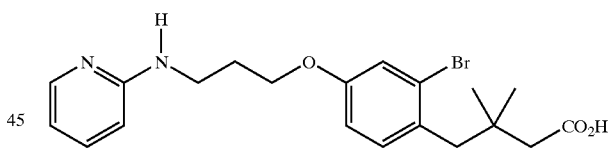

4-{2-bromo-4-[3-(pyridin-2-ylamino)propoxy]phenyl}-3,3-dimethylbutanoic Acid Trifluoroacetate Ethyl 4-{2-bromo-4-[3-(pyridin-2-ylamino)propoxy]phenyl}-3,3-dimethylbutanoate (225 mg) was dissolved in a mixture of 2.0 mL methanol and 2.0 mL of THF and 2.0 mL of 1N NaOH solution was added. The reaction mixture was stirred at ambient temperature for 5 hours. The volatile solvents were removed and the remaining aqueous solution was acidified with 2.0 mL of 1N HCl and was concentrated to the give crude product. The crude product was purified by HPLC using acetonitrile:water gradient to yield 125 mg of the title compound as a TFA salt. $^1$H NMR (DMSO) δ12.1 (br s, 1H), 8.75 (brs, 1H), 7.92–7.82 (m, 2H), 7.38(d, J=9 Hz, 1H), 7.18–7.15 (m, 1H) 7.02 (d, J=9 Hz, 1H), 6.95–6.91 (m, 1H), 6.84–6.80 (m, 1H), 4.09 (t, 2H), 3.51–3.47 (m, 2H), 2.76 (s, 2H), 2.16 (s, 2H), 2.1–2.0 (m, 2H), 0.98 (s, 6H). Anal. Calcd. for C$_{20}$H$_{25}$N$_2$O$_3$Br plus 1.40 CF$_3$CO$_2$H: C,47.14; H,4.58; N,4.82. Found: C,47.19; H,4.54; N,4.63.

EXAMPLE 26

4-{2-cyano-4-[3-(pyridin-2-ylamino)propoxy]phenyl}-3,3-dimethylbutanoic Acid

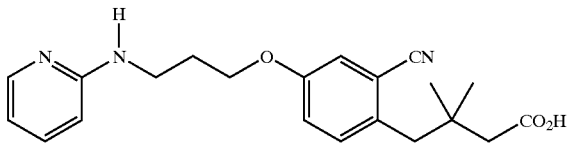

Step 1

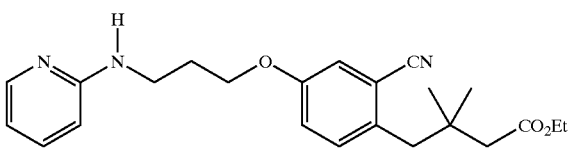

Ethyl 4-{2-cyano-4-[3-(pyridin-2-ylamino)propoxy]phenyl}-3,3-dimethylbutanoate

Ethyl 4-{2-bromo-4-[3-(pyridin-2-ylamino)propoxy]phenyl}-3,3-dimethylbutanoate (500 mg) was dissolved in DMF (10 mL) and water (1.0 mL) and was treated with tris(dibenzylideneacetone)dipalladium(0) (51 mg) and bis(diphenylphosphino)ferrocene (75 mg). The reaction mixture was heated to 120° C. for 20 hours under nitrogen atmosphere. The mixture was cooled to room temperature and was filtered through Celite under vacuum. The filtrate was concentrated. The residue was dissolved in ethyl acetate and was washed with a saturated solution of ammonium chloride, dried ($Na_2SO_4$) and concentrated. The crude product was purified by flash chromatography (EA/Hexane: 40/60) to give 390 mg (88.6%) of the desired compound as an oily gum. NMR spectrum was consistent for the proposed structure.

Step 2

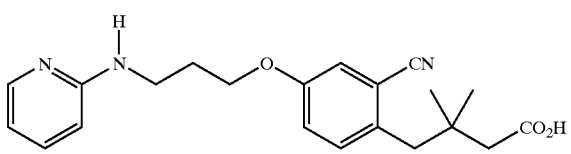

4-{2-cyano-4-[3-(pyridin-2-ylamino)propoxy]phenyl}-3,3-dimethylbutanoic Acid Trifluoroacetate Ethyl 4-{2-cyano-4-[3-(pyridin-2-ylamino)propoxy]phenyl}-3,3-dimethylbutanoate (175 mg) was dissolved in a mixture of 2.0 mL methanol and 2.0 mL of THF and 2.0 mL of 1N NaOH solution was added. The reaction mixture was stirred at ambient temperature for 5 hours. The volatile solvents were removed and the remaining aqueous solution was acidified with 2.0 mL of 1N HCl and was concentrated to give the crude product. The crude product was purified by HPLC using acetonitrile:water gradient to yield 120 mg of the title compound as a TFA salt. $^1$H NMR (DMSO) δ12.1 (br s, 1H), 8.7 (br s, 1H), 7.92–7.80 (m, 2H), 7.4–7.34 (m, 2H), 7.26–7.2 (m, 1H), 7.02 (d, J=9 Hz, 1H), 6.85–6.8 (m, 1H), 4.13 (m, 2H), 3.53–3.47 (m, 2H), 2.8 (s, 2H), 2.15 (s, 2H), 2.11–2.01 (m, 2H), 0.98 (s, 6H); Anal. Calcd. for $C_{21}H_{25}N_3O_3$ and 1.60 $CF_3CO_2H$, plus 0.5 $H_2O$: C,51.84; H,5.06; N,7.43. Found: C,52.11; H,5.36.; N,6.93; Mass Spectrum: (MH+)=368.

EXAMPLE 27

4-{2-ethynyl-4-[3-(pyridin-2-ylamino)propoxy]phenyl}-3,3-dimethylbutanoic Acid

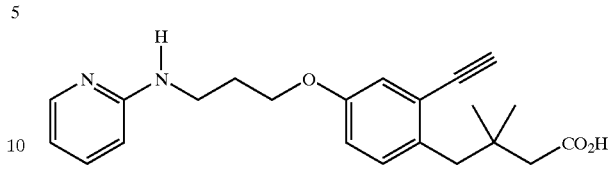

Step 1

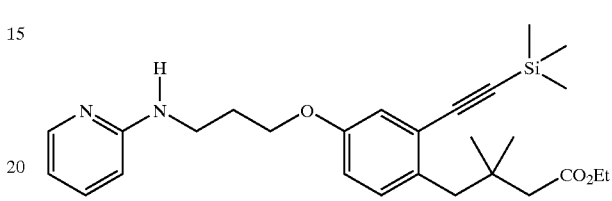

Ethyl 3,3-dimethyl-4-{4-[3-(pyridin-2-ylamino)propoxy]-2-[(trimethylsilyl)ethynyl]phenyl}butanoate Ethyl 4-{2-bromo-4-[3-(pyridin-2-ylamino)propoxy]phenyl}-3,3-dimethylbutanoate (300 mg) was dissolved in $Et_3N$ (3 ml) followed by the addition of trimethylsiylacetylene (144 μL), CuI (24 mg), triphenylphosphine (50 mg), and $Pd(Ph_3P)_2Cl_2$ (23 mg). The reaction mixture was heated to 120° C. in a sealed tube for 20 hours under nitrogen atmosphere. The mixture was cooled to room temperature and was filtered through celite under vacuum. The filtrate was concentrated. The residue was dissolved in ethyl acetate and was washed with a saturated solution of ammonium chloride, dried ($Na_2SO_4$) and concentrated. The crude product was purified by flash chromatography on silica gel (EA/Hexane: 40/60) to give ~200 mg of desired compound as oily gum. NMR spectrum was consistent for the proposed structure.

Step 2

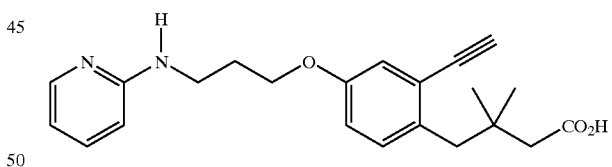

4-{2-ethynyl-4-[3-(pyridin-2-ylamino)propoxy]phenyl}-3,3-dimethylbutanoic Acid Trifluoroacetate Ethyl 3,3-dimethyl-4-{4-[3-(pyridin-2-ylamino)propoxy]-2-[(trimethylsilyl)ethynyl]phenyl}butanoate (175 mg) was dissolved in a mixture of 2.0 mL methanol and 2.0 mL of THF and 2.0 mL of 1N NaOH solution was added. The reaction mixture was stirred at ambient temperature for 5 hours. The volatile solvents were removed and the remaining aqueous solution was acidified with 2.0 mL of 1N HCl and was concentrated to give the crude product. The crude product was purified by HPLC using acetonitrile:water gradient to yield 130 mg of the title compound as a TFA salt. $^1$H NMR (DMSO) δ12.1 (br s, 1H), 8.65 (br s, 1H), 7.92–7.80 (m, 2H), 7.2–7.15 (m, 1H), 7.02–6.9 (m, 3H), 6.81 (t, 1H), 4.1–4.03 (m, 2H), 3.53–3.47 (m, 3H), 2.78 (s, 2H), 2.12 (s, 2H), 2.11–2.01 (m, 2H), 0.98 (s, 6H); Anal. Calcd. for $C_{22}H_{26}N_2O_3$ and 1.4 $CF_3CO_2H$ plus 1 $H_2O$: C,54.75; H,5.45; N,5.15. Found: C,54.51; H,5.21.; N,4.99; Mass Spectrum: (MH+)=367.

EXAMPLE 28

3,3-Dimethyl-4-{2-(phenylethynyl)-4-[3-(pyridin-2-ylamino)propoxy]phenyl}butanoic Acid

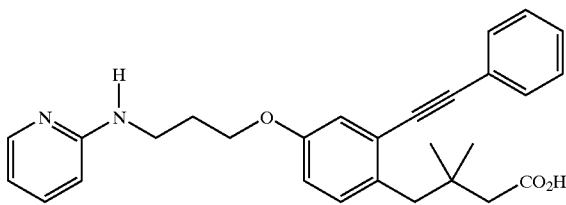

Step 1

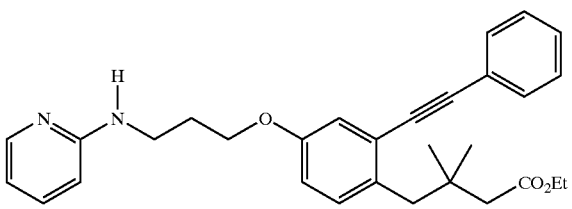

Ethyl 3,3-dimethyl-4-{2-(phenylethynyl)-4-[3-(pyridin-2-ylamino)propoxy]phenyl}butanoate Ethyl 4-{2-bromo-4-[3-(pyridin-2-ylamino)propoxy] phenyl}-3,3-dimethylbutanoate (500 mg) was dissolved in $Et_3N$ (5 ml) followed by the addition of phenylylacetylene (250 μL), CuI (11 mg), triphenylphosphine (85 mg), and $Pd(Ph_3P)_2Cl_2$ (42 mg). The reaction mixture was heated to 80° C. under a nitrogen atmosphere for 24 hours. Further phenylacetylene (125 μL) and triethylamine (5 mL) were added and heating was continued for a further 24 h. The mixture was cooled to room temperature, diluted with ethyl acetate (50 mL) and filtered through a pad of celite. The solvent was evaporated and the residue was chromatographed on silica gel eluting with hexane/ethyl acetate (3:2). This gave the product (516 mg) as an oil. The NMR spectrum was consistent for the proposed structure.
Step 2

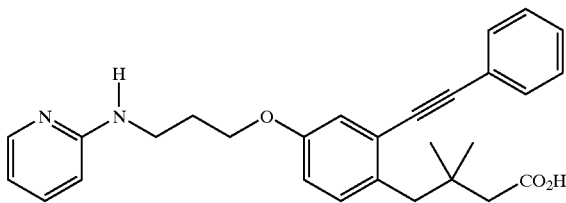

3,3-Dimethyl-4-{2-(phenylethynyl)-4-[3-(pyridin-2-ylamino)propoxy]phenyl}butanoic Acid Trifluoroacetate Ethyl 3,3-dimethyl-4-{2-(phenylethynyl)-4-[3-(pyridin-2-ylamino)propoxy]phenyl}butanoate (250 mg) was dissolved in a mixture of ethanol (5 mL) and 1N NaOH solution (2 mL). The reaction mixture was stirred at ambient temperature for 4 days. The solution was adjusted to pH 7 by addition of 2N HCl and was concentrated to give the crude product. The crude product was purified by HPLC using acetonitrile:water gradient to yield 175 mg of the title compound as a TFA salt. $^1$H NMR (DMSO) δ12.05 (br s, 1H), 8.70 (br s, 1H), 7.83–7.93 (m, 2H), 7.52–7.58 (m, 2H), 7.41–7.49 (m, 3H), 7.23 (d, 1H), 7.09 (d, 1H), 7.03 (d,1H), 6.95 (dd, 1H), 6.84 (t,1H), 4.11 (t, 2H), 3.45–3.52 (m, 2H), 2.85 (s, 2H), 2.19 (s, 2H), 2.01–2.11 (m, 2H), 1.00 (s, 6H); Anal. Calcd. for $C_{28}H_{30}N_2O_3$ and 1.4 $CF_3CO_2H$: C,61.82; H,5.30; N,4.70. Found: C,61.81; H,5.49.; N,4.61; Mass Spectrum: (MH+)=443.

The activity of the compounds of the present invention was tested in the following assays. Compounds of the present invention antagonize the $α_vβ_3$ integrin with an $IC_{50}$ of 0.1 nM to 100 μM in the 293-cell assay. Similarly these compounds also antagonized the $α_vβ_5$ integrin with an $IC_{50}$ of <50 μM in the cell adhesion assay.

Vitronectin Adhesion Assay
Materials

Human vitronectin receptors $α_vβ_3$ and $α_vβ_5$ were purified from human placenta as previously described [Pytela et al., *Methods in Enzymology*, 144:475–489 (1987)]. Human vitronectin was purified from fresh frozen plasma as previously described [Yatohgo et al., *Cell Structure and Function*, 13:281–292 (1988)]. Biotinylated human vitronectin was prepared by coupling NHS-biotin from Pierce Chemical Company (Rockford, Ill.) to purified vitronectin as previously described [Charo et al., *J. Biol. Chem.*, 266(3): 1415–1421 (1991)]. Assay buffer, OPD substrate tablets, and RIA grade BSA were obtained from Sigma (St. Louis, Mo.). Anti-biotin antibody was obtained from Sigma (St. Louis, Mo.). Nalge Nunc-Immuno microtiter plates were obtained from Nalge Company (Rochester, N.Y.).

Methods

Solid Phase Receptor Assays

This assay was essentially the same as previously reported [Niiya et al., *Blood*, 70:475–483 (1987)]. The purified human vitronectin receptors $α_vβ_3$ and $α_vβ_5$ were diluted from stock solutions to 1.0 μg/mL in Tris-buffered saline containing 1.0 mM $Ca^{++}$, $Mg^{++}$, and $Mn^{++}$, pH 7.4 (TBS$^{+++}$). The diluted receptors were immediately transferred to Nalge Ninc-Immuno microtiter plates at 100 μL/well (100 ng receptor/well). The plates were sealed and incubated overnight at 4° C. to allow the receptors to bind to the wells. All remaining steps were at room temperature. The assay plates were emptied and 200 μL of 1% RIA grade BSA in TBS$^{+++}$ (TBS$^{+++}$/BSA) were added to block exposed plastic surfaces. Following a 2 hour incubation, the assay plates were washed with TBS$^{+++}$ using a 96 well plate washer. Logarithmic serial dilution of the test compound and controls were made starting at a stock concentration of 2 mM and using 2 nM biotinylated vitronectin in TBS$^{+++}$/BSA as the diluent. This premixing of labeled ligand with test (or control) ligand, and subsequent transfer of 50 μL aliquots to the assay plate was carried out with a CETUS Propette robot; the final concentration of the labeled ligand was 1 nM and the highest concentration of test compound was 1.0× $10^{-4}$ M. The competition occurred for two hours after which all wells were washed with a plate washer as before. Affinity purified horseradish peroxidase labeled goat anti-biotin antibody was diluted 1:2000 in TBS$^{+++}$/BSA and 125 μL was added to each well. After 45 minutes, the plates were washed and incubated with OPD/$H_2O_2$ substrate in 100 mM/L Citrate buffer, pH 5.0. The plate was read with a microtiter plate reader at a wavelength of 450 nm and when the maximum-binding control wells reached an absorbance of about 1.0, the final $A_{450}$ were recorded for analysis. The data were analyzed using a macro written for use with the EXCEL spreadsheet program. The mean, standard deviation, and %CV were determined for duplicate concentrations. The mean $A_{450}$ values were normalized to the mean of four maximum-binding controls (no competitor added)(B-MAX). The normalized values were subjected to a four parameter curve fit algorithm [Rodbard et al., *Int. Atomic Energy Agency, Vienna,* pp 469 (1977)], plotted on a semi-log scale, and the computed concentration corresponding to inhibition of 50% of the maximum binding of biotinylated vitronectin ($IC_{50}$) and corresponding $R^2$ was reported for those compounds exhibiting greater than 50% inhibition at the highest concentration tested; otherwise the $IC_{50}$ is reported as being greater than the highest concentration tested. β-[[2-[[5-[(aminoiminomethyl)amino]-1-oxopentyl]amino]-1-oxoethyl]amino]-3-pyridinepropanoic acid [U.S. Pat. No. 5,602,155 Example 1] which is a potent $α_vβ_3$ antagonist ($IC_{50}$ in the range 3–10 nM) was included on each plate as a positive control.

Purified IIb/IIIa Receptor Assay

Materials

Human fibrinogen receptor (IIb/IIIa) was purified from outdated platelets. (Pytela, R., Pierschbacher, M. D., Argraves, S., Suzuki, S., and Rouslahti, E. "Arginine-Glycine-Aspartic acid adhesion receptors", *Methods in Enzymology* 144(1987):475–489.) Human vitronectin was purified from fresh frozen plasma as described in Yatohgo, T., Izumi, M., Kashiwagi, H., and Hayashi, M., "Novel purification of vitronectin from human plasma by heparin affinity chromatography," *Cell Structure and Function* 13(1988):281–292. Biotinylated human vitronectin was prepared by coupling NHS-biotin from Pierce Chemical Company (Rockford, Ill.) to purified vitronectin as previously described. (Charo, I. F., Nannizzi, L., Phillips, D. R., Hsu, M. A., Scarborough, R. M., "Inhibition of fibrinogen binding to GP IIb/IIIa by a GP IIIa peptide", *J. Biol. Chem.* 266(3) (1991): 1415–1421.) Assay buffer, OPD substrate tablets, and RIA grade BSA were obtained from Sigma (St. Louis, Mo.). Anti-biotin antibody was obtained from Sigma (St. Louis, Mo.). Nalge Ninc-Immuno microtiter plates were obtained from (Rochester, N.Y.). ADP reagent was obtained from Sigma (St. Louis, Mo.).

Methods

Solid Phase Receptor Assays

This assay is essentially the same reported in Niiya, K., Hodson, E., Bader, R., Byers-Ward, V. Koziol, J. A., Plow, E. F. and Ruggeri, Z. M., "Increased surface expression of the membrane glycoprotein IIb/IIIa complex induced by platelet activation: Relationships to the binding of fibrinogen and platelet aggregation", *Blood* 70(1987):475–483. The purified human fibrinogen receptor (IIb/IIIa) was diluted from stock solutions to 1.0 μg/mL in Tris-buffered saline containing 1.0 mM $Ca^{++}$, $Mg^{++}$, and $Mn^{++}$, pH 7.4 ($TBS^{+++}$). The diluted receptor was immediately transferred to Nalge Ninc-Immuno microtiter plates at 100 μL/well (100 ng receptor/well). The plates were sealed and incubated overnight at 4° C. to allow the receptors to bind to the wells. All remaining steps were at room temperature. The assay plates were emptied and 200 μL of 1% RIA grade BSA in $TBS^{+++}$ ($TBS^{+++}$/BSA) were added to block exposed plastic surfaces. Following a 2 hour incubation, the assay plates were washed with $TBS^{+++}$ using a 96 well plate washer. Logarithmic serial dilution of the test compound and controls were made starting at a stock concentration of 2 mM and using 2 nM biotinylated vitronectin in $TBS^{+++}$/BSA as the diluent. This premixing of labeled ligand with test (or control) ligand, and subsequent transfer of 50 μL aliquots to the assay plate was carried out with a CETUS Propette robot; the final concentration of the labeled ligand was 1 nM and the highest concentration of test compound was 1.0× $10^{-4}$ M. The competition occurred for two hours after which all wells were washed with a plate washer as before. Affinity purified horseradish peroxidase labeled goat anti-biotin antibody was diluted 1:2000 in $TBS^{+++}$/BSA and 125 μL were added to each well. After 45 minutes, the plates were washed and incubated with $ODD/H_2O_2$ substrate in 100 mM/L citrate buffer, pH 5.0. The plate was read with a microtiter plate reader at a wavelength of 450 nm and when the maximum-binding control wells reached an absorbance of about 1.0, the final $A_{450}$ were recorded for analysis. The data were analyzed using a macro written for use with the EXCELJ spreadsheet program. The mean, standard deviation, and %CV were determined for duplicate concentrations. The mean $A_{450}$ values were normalized to the mean of four maximum-binding controls (no competitor added) (B-MAX). The normalized values were subjected to a four parameter curve fit algorithm, [Robard et al., *Int. Atomic Energy Agency, Vienna,* pp 469 (1977)], plotted on a semi-log scale, and the computed concentration corresponding to inhibition of 50% of the maximum binding of biotinylated vitronectin ($IC_{50}$) and corresponding $R^2$ was reported for those compounds exhibiting greater than 50% inhibition at the highest concentration tested; otherwise the $IC_{50}$ is reported as being greater than the highest concentration tested. β-[[2-[[5-[(aminoiminomethyl)amino]-1-oxopentyl]amino]-1-oxoethyl]amino]-3-pyridinepropanoic acid, bistrifluoroacetate salt [U.S. Pat. No. 5,602,155 Example 1] which is a potent IIb/IIIa antagonist ($IC_{50}$ in the range 8–18 nM) was included on each plate as a positive control.

Human Platelet Rich Plasma Assays

Healthy aspirin free donors were selected from a pool of volunteers. The harvesting of platelet rich plasma and subsequent ADP induced platelet aggregation assays were performed as described in Zucker, M. B., "Platelet Aggregation Measured by the Photometric Method", *Methods in Enzymology* 169(1989):117–133. Standard venipuncture techniques using a butterfly allowed the withdrawal of 45 mL of whole blood into a 60 mL syringe containing 5 mL of 3.8% trisodium citrate. Following thorough mixing in the syringe, the anti-coagulated whole blood was transferred to a 50 mL conical polyethylene tube. The blood was centrifuged at room temperature for 12 minutes at 200×g to sediment non-platelet cells. Platelet rich plasma was removed to a polyethylene tube and stored at room temperature until used. Platelet poor plasma was obtained from a second centrifugation of the remaining blood at 2000×g for 15 minutes. Platelet counts are typically 300,000 to 500,000 per microliter. Platelet rich plasma (0.45 mL) was aliquoted into siliconized cuvettes and stirred (1100 rpm) at 37° C. for 1 minute prior to adding 50 uL of pre-diluted test compound. After 1 minute of mixing, aggregation was initiated by the addition of 50 uL of 200 uM ADP. Aggregation was recorded for 3 minutes in a Payton dual channel aggregometer (Payton Scientific, Buffalo, N.Y.). The percent inhibition of maximal response (saline control) for a series of test compound dilutions was used to determine a dose response curve. All compounds were tested in duplicate and the concentration of half-maximal inhibition ($IC_{50}$) was calculated graphically from the dose response curve for those compounds which exhibited 50% or greater inhibition at the highest concentration tested; otherwise, the IC$_{50}$ is reported as being greater than the highest concentration tested.

Cell Assays for Potency and Selectivity

While the $\beta_3$ subunit of $\alpha_v\beta_3$ is only known to complex with $\alpha_v$ or $\alpha_{IIb}$, the $\alpha_v$ subunit complexes with multiple $\beta$ subunits. The three $\alpha_v$ integrins most homologous with $\alpha_v\beta_3$ are $\alpha_v\beta_1$, $\alpha_v\beta_5$ and $\alpha_v\beta_6$, with 43%, 56% and 47% amino acid identity in the $\beta$ subunits, respectively. To evaluate the selectivity of compounds between the integrins $\alpha_v\beta_3$ and $\alpha_v\beta_6$, cell-based assays were established using the 293 human embryonic kidney cell line. 293 cells express $\alpha_v\beta_1$, but little to no detectable $\alpha_v\beta_3$ or $\alpha_v\beta_6$. cDNAs for $\beta_3$ and $\beta_6$ were transfected separately into 293 cells to generate 293-$\beta$3 and 293-$\beta$6 cells, respectively. High surface expression of $\alpha_v\beta_3$ and $\alpha_v\beta_6$ was confirmed by flow cytometry. Conditions were established for each cell line in which cell adhesion to immobilized human vitronectin was mediated by the appropriate integrin, as determined by a panel of integrin-specific, neutralizing monoclonal antibodies. Briefly, cells were incubated with inhibitor in the presence of 200 uM Mn$^{2+}$, allowed to adhere to immobilized vitronectin, washed, and adherent cells are detected endogenous alkaline phosphatase and para-nitrophenyl phosphate. An 8-point dose-response curve using either 10-fold or 3-fold dilutions of compound was evaluated by fitting a four-parameter logistic, nonlinear model (using SAS). To evaluate compound potency for membrane-bound $\alpha_v\beta_6$ an additional cell-based adhesion assay was established using the HT-29 human colon carcinoma cell line. High surface expression of $\alpha_v\beta_6$ on HT-29 cells was confirmed by flow cytometry. Conditions were established in which cell adhesion to immobilized human latency associated peptide (LAP) was mediated by the $\alpha_v\beta_6$, as determined by a panel of integrin-specific, neutralizing monoclonal antibodies. Briefly, cells were incubated with inhibitor in the presence of 200 uM Mn$^{2+}$, allowed to adhere to immobilized LAP, washed, and adherent cells are detected by quantifying endogenous alkaline phosphatase using para-nitrophenyl phosphate. An 8point dose-response curve using either 10-fold or 3-fold dilutions of compound was evaluated by fitting a four-parameter logistic, nonlinear model (using SAS). The compounds evaluated were relatively ineffective at inhibition of $\alpha_v\beta_6$-mediated cell adhesion. The selective antagonism of the $\alpha_v\beta_3$ integrin is viewed as desirable in this class of compounds, as $\alpha_v\beta_6$ may also play a role in normal physiological processes of tissue repair and cellular turnover that routinely occur in the skin and pulmonary tissues.

What is claimed is:
1. A compound of the Formula:

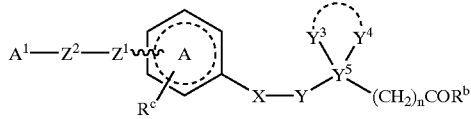

and pharmaceutically acceptable salts, diastereomers, enantiomers, tautomers, and racemates thereof;

wherein:

is a phenyl ring optionally substituted with one or more substituents selected from the group consisting of alkyl, haloalkyl, aryl, heteroaryl, halogen, alkoxyalkyl, aminoalkyl, hydroxy, nitro, alkoxy, hydroxyalkyl, thioalkyl, amino, alkylamino, arylamino, alkylsulfonamido, acyl, acylamino, alkylsulfone, sulfonamide, allyl, alkenyl, methylenedioxy, ethylenedioxy, alkynyl, carboxamide, cyano, and —(CH$_2$)$_m$—COR;

m is 0 to 2;

R is selected from the group consisting of hydroxy, alkoxy, alkyl and amino;

A$^1$ is a pyridine ring optionally substituted by one or more R$^k$ selected from the group consisting of hydroxy, alkyl, alkoxy, alkoxyalkyl, thioalkyl, haloalkyl, cyano, amino, alkylamino, halogen, acylamino, sulfonamide and —COR;

Z$^1$ is O;

Z$^1$ is attached to ring A at the meta- or para- position relative to X;

Z$^2$ is a 1–5 carbon linker containing 0–3 N atoms; wherein the carbon and nitrogen atoms of Z$^1$–Z$^2$ are optionally substituted with a substituent selected from the group consisting of alkyl, alkoxy, thioalkyl, alkylsulfone, aryl, alkoxyalkyl, alkylamino, heteroaryl, hydroxy, alkenyl, alkynyl, carboxyalkyl, halogen, haloalky and acylamino;

n is 1 or 2;

R$^c$ is selected from the group consisting of H; alkyl; halogen, hydroxy, nitro, alkoxy, amino, haloalkyl, aryl, heteroaryl, alkoxyalkyl, aminoalkyl, hydroxyalkyl, thioalkyl, alkylamino, arylamino, alkylsulfonylamino, acyl, acylamino, sulfonyl, sulfonamide, allyl, alkenyl, methylenedioxy, ethylenedioxy, alkynyl, alkynylalkyl, carboxy, alkoxycarbonyl, carboxamido, cyano, and —(CH$_2$)$_m$COR;

with respect to X and Y:
X is selected from the group consisting of —CHR$^c$— and CHO wherein R$^c$ is selected from the group consisting of H, lower alkyl, alkoxy, cycloalkyl, alkoxyalkyl, hydroxy, alkynyl, alkenyl, haloalkyl, thioalkyl, aralkyl and aryl; wherein R$^c$ can optionally form a lactone with the carboxylic acid function of the chain; and Y is selected from the group consisting of (CH$_2$)$_p$, —CR$^g$—, CO and SO$_2$, wherein R$^g$ is selected from the group consisting of H, alkyl, haloalkyl, alkoxyalkyl, alkynyl, aryl, heteroaryl, aralkyl, hydroxy, alkoxy, and carboxyalkyl; wherein p is 0 or 1; or
the group X—Y optionally contains a moiety selected from the group consisting of acyl, alkyl, sulfonyl, amino, ether, thioether, carboxamido, sulfonamido and alkenyl;

with respect to Y$^3$, Y$^4$, and Y$^5$:
Y$^5$ is C; and Y$^3$ and Y$^4$ are independently selected from the group consisting of alkyl, haloalkyl, hydroxy, alkoxy, cyano, halogen, aralkyl, heteroaralkyl, alkoxyalkyl, hydroxyalkyl, aryloxyalkyl, alkylsulfone, alkene or alkyne; wherein the alkyl group optionally contains 0–4 heteroatoms selected from the group consisting of N, O, and S and $SO_2$; or $Y^5$ is C; and when $Y^3$ is aryl or heteroaryl, $Y^4$ is selected from the group consisting of aryl, heteroaryl, alkene, alkyne, alkoxy, hydroxy, cyano, alkoxyalkyl and alkylsulfone; or $Y^5$ is C; and $Y^3$ taken together with $Y^4$ forms a 3–8 membered monocyclic or a 7–11 membered bicyclic ring, containing 2–3 double bonds, containing 0–4 heteroatoms or functional groups selected from O, $NR^g$, S, CO or $SO_2$, optionally substituted with one or more substituent selected from the group consisting of alkyl, haloalkyl, halogen, haloalkyl, alkoxy, alkyne, cyano, alkylsulfone, sulfonamide, carboalkoxy and carboxyalkyl; or $Y^3$, $Y^4$ and $Y^5$ is a sulfone group;

$R^b$ is $X^2—R^h$ wherein $X^2$ is selected from the group consisting of O, S and $NR^j$:

$R^h$ and $R^j$ are independently selected from the group consisting of H, alkyl, aryl, aralkyl, acyl and alkoxyalkyl.

2. A compound according to claim 1 and pharmaceutically acceptable salts, diastereomers, enantiomers, tautomers, and racemates thereof;
wherein:
$A^1$ is

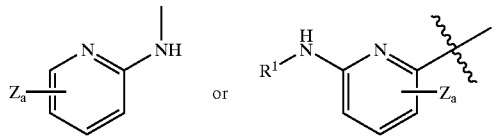

$Z_a$ is selected from the group consisting of H, alkyl, alkoxy, hydroxy, amine, alkylamine, dialkylamine, carboxyl, alkoxycarbonyl, hydroxyalkyl, halogen and haloalkyl; and $R^1$ is selected from the group consisting of H, alkyl, alkoxyalkyl, acyl, haloalkyl and alkoxycarbonyl.

3. A compound according to claim 1, and pharmaceutically acceptable salts, diastereomers, enantiomers, tautomers, and racemates thereof; wherein:

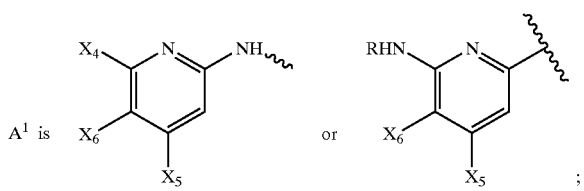

$X_4$ and $X_5$ are selected from the group consisting of H, alkyl, branched alkyl, alkylamino, alkoxyalkylamino, haloalkyl, thioalkyl, halogen, amino, alkoxy, aryloxy, alkoxyalkyl, hydroxy, cyano and acylamino groups; and $X_6$ is selected from the group consisting of H, alkyl, hydroxy, halogen, alkoxy and haloalkyl.

4. A compound according to claim 1 and pharmaceutically acceptable salts, isomers, tautomers, and racemates thereof; wherein:
n=1;
A is a phenyl ring substituted with $R^c$;

Y is $(CH_2)_p$; wherein p=0;
$Y^5$ is C.

5. A compound according to claim 1 and pharmaceutically acceptable salts, diastereomers, enantiomers, tautomers, and racemates thereof;
wherein:
n=1;
A is a phenyl ring substituted with $R^c$;
Y is $(CH_2)_p$; wherein p=0;
$Y^5$ is C; and
$Y^3$ taken with $Y^4$ forms a moncylclic or bicyclic ring B.

6. A compound according to claim 5, and pharmaceutically acceptable salts, diastereomers, enantiomers, tautomers, and racemates thereof;
wherein:
the ring B is selected from the group consisting of

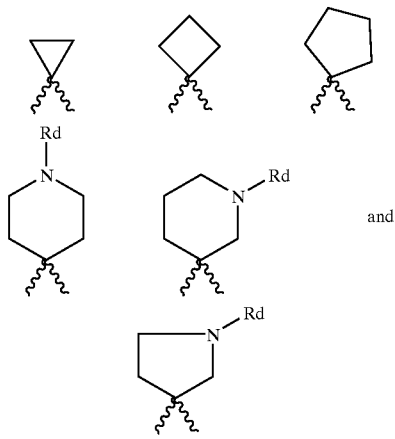

wherein Rd is selected from the group consisting of hydrogen, alkyl, acyl, alkoxyalkyl, haloalkyl, alkylsulfone, aryl, heteroaryl, aralkyl and heteroaralkyl.

7. A compound according to claim 1 and pharmaceutically acceptable salts, diastereomers, enantiomers, tautomers, and racemates thereof;
wherein:
n=1;
A is a phenyl ring substituted with $R^c$;
Y is $(CH_2)_p$; wherein p=0; and
$Y^5$ taken together with $Y^3$ and $Y^4$ forms a sulfone group.

8. A compound according to claim 1 and pharmaceutically acceptable salts, diastereomers, enantiomers, tautomers, and racemates thereof selected from the group consisting of:
1-[2-oxo-2-[4-[3-(2 pyridinylamino)propoxy]phenyl]ethyl] cyclopentaneacetic acid;
1-[2-[4-[3-(2-pyridinylamino)propoxy]phenyl]ethyl] cyclopentaneacetic acid;
1-[2-oxo-2-[4-[2-(2-pyridinylamino)ethoxy]phenyl]ethyl] cyclopentaneacetic acid;
4-{4-[2-(6-aminopyridin-2-yl)ethoxy]phenyl}-3,3-dimethylbutanoic acid; 3,3-dimethyl-4-{4-[3-(pyridin-2-ylamino)propoxy]phenyl}butanoic acid;
1-[[4-[3-(2-pyridinylaminopropoxy]phenyl]methyl] cyclopropaneacetic acid;
[[[4-[3-(2-pyridinylamino)propoxy]phenyl]methyl] sulfonyl]acetic acid; 1-[[4-[3-(2-pyridinylamino) propoxy]phenyl]methyl]cyclobutaneacetic acid;
1-[[4-[3-(2-pyridinylamino)propoxy]phenyl]methyl] cyclopentane-acetic acid;

[[[4-[2-[6-(methylamino)-2-pyridinyl]ethoxy]phenyl] methyl]sulfonyl]acetic acid;

3-benzyl-3-methyl-4-{4-[3-(pyridin-2-ylamino)propoxy] phenyl}-butanoic acid;

4-{3-bromo-4-[3-(pyridin-2-ylamino)propoxy]phenyl}-3,3-dimethylbutanoic acid;

4-{3-cyano-4-[3-(pyridin-2-ylamino)propoxy]phenyl}-3,3-dimethylbutanoic acid;

4-{3-ethynyl-4-[3-(pyridin-2-ylamino)propoxy]phenyl}-3,3-dimethylbutanoic acid;

5-(3-carboxy-2,2-dimethylpropyl)-2-[3-(pyridin-2-ylamino)propoxy]benzoic acid;

1-acetyl-4[[4-[3-(2-pyridinylamino)propoxy]phenyl]methyl]-4-piperidineacetic acid;

(1-acetyl-3-{4-[3-(pyridin-2-ylamino)propoxy]benzyl}piperidin-3-yl)acetic acid;

4-{3-bromo-5-fluoro-4-[3-(pyridin-2-ylamino)propoxy]phenyl}-3,3-dimethylbutanoic acid;

4-{3-fluoro-4-[3-(pyridin-2-ylamino)propoxy]phenyl}-3,3-dimethylbutanoic acid;

4-{3-methoxy-4-[3-(pyridin-2-ylamino)propoxy]phenyl}-3,3-dimethylbutanoic acid;

4-{3-chloro-4-[3-(pyridin-2-ylamino)propoxy]phenyl}-3,3-dimethylbutanoic acid;

3-Methyl-3-{4-[3-(pyridin-2-ylamino)-propoxy]-benzyl}-pent-4-enoic acid;

4-{2-bromo-4-[3-(pyridin-2-ylamino)propoxy]phenyl}-3,3-dimethylbutanoic acid;

4-{2-cyano-4-[3-(pyridin-2-ylamino)propoxy]phenyl}-3,3-dimethylbutanoic acid;

4-{2-ethynyl-4-[3-(pyridin-2-ylamino)propoxy]phenyl}-3,3-dimethylbutanoic acid; and 3,3-Dimethyl-4-{2-(phenylethynyl)-4-[3-(pyridin-2-ylamino)propoxy]phenyl}butanoic acid.

9. A pharmaceutical composition comprising a therapeutically effective amount of a compound of claims 1, 2, 3, 4, 5, 6, 7 or 8 and a pharmaceutically acceptable carrier.

10. A method for treating conditions mediated by the $\alpha_V\beta_3$ integrin in a mammal in need of such treatment comprising administering an effective $\alpha_V\beta_3$ inhibiting amount of a compound of claims 1, 2, 3, 4, 5, 6, 7 or 8.

11. A method according to claim 10 wherein the condition treated is selected from the group consisting of tumor metastasis, tumor growth, solid tumor growth, angiogenesis, osteoporosis, humoral hypercalemia of malignancy, smooth muscle cell migration, restenosis, atherosclerosis, macular degeneration, retinopathy, and arthritis.

12. A method for treating conditions mediated by the $\alpha_V\beta_5$ integrin in a mammal in need of such treatment comprising administering an effective $\alpha_V\beta_5$ inhibiting amount of a compound of claims 1, 2, 3, 4, 5, 6, 7 or 8.

13. A method according to claim 12 wherein the condition treated is selected from the group consisting of tumor metastasis, tumor growth, solid tumor growth, angiogenesis, osteoporosis, humoral hypercalcemia of malignancy, smooth muscle cell migration, restenosis, atherosclerosis, macular degeneration, retinopathy, and arthritis.

14. A method of treating neoplasia in a patient in need thereof comprising administering a therapeutically effective amount of a compound of claims 1, 2, 3, 4, 5, 6, 7 or 8 in combination with a chemotherapeutic agent.

15. A compound of claims 1, 2, 3, 4, 5, 6, 7 or 8 that selectively antagonizes $\alpha_V\beta_3$ and the $\alpha_V\beta_5$ integrins, over the $\alpha_V\beta_6$ integrin.

* * * * *